United States Patent [19]

Fujii, deceased et al.

[11] Patent Number: 5,204,326

[45] Date of Patent: * Apr. 20, 1993

[54] POLYPEPTIDE DERIVATIVES AND CALCIUM METABOLISM IMPROVING AGENT

[75] Inventors: Setsuro Fujii, deceased, late of Kyoto; by Keiko Fujii, successor, Kyoto; by Shinichiro Fujii, successor, Uji; by Kaoruko Takada, successor, Ehime; Yoshihito Yamamoto; Fumio Shimizu, both of Otsu; Masatoshi Inai, Tokushima; Naosumi Kinoshita, Otsu; Shizuo Nakamura, Naruto; Mitsuru Hirohashi; Takashi Sakamoto, both of Otsu; Kazuhiko Tsutsumi, Tokushima; Tetsuhiko Shirasaka, Otsu, all of Japan

[73] Assignees: Otsuka Pharmaceutical Co., Ltd., Tokyo; Otsuka Pharmaceutical Factory, Inc., Tokushima, both of Japan

[*] Notice: The portion of the term of this patent subsequent to Nov. 10, 2009 has been disclaimed.

[21] Appl. No.: 493,359

[22] Filed: Mar. 14, 1990

[30] Foreign Application Priority Data

Mar. 16, 1989 [JP] Japan .................. 1-065446
Jul. 12, 1989 [JP] Japan .................. 1-180908
Aug. 3, 1989 [JP] Japan .................. 1-201869

[51] Int. Cl.$^5$ .............. A61K 37/02; C07K 5/12; C07K 7/36
[52] U.S. Cl. .................. 514/11; 530/307; 530/317
[58] Field of Search .................. 514/11; 530/307, 317

[56] References Cited

U.S. PATENT DOCUMENTS

| | | | |
|---|---|---|---|
| 4,086,221 | 4/1978 | Sakakibara et al. | 530/307 |
| 4,528,132 | 7/1985 | Orlowski et al. | 530/307 |
| 4,597,900 | 7/1986 | Orlowski et al. | 530/307 |
| 4,604,236 | 8/1986 | Orlowski et al. | 530/307 |
| 4,605,515 | 8/1986 | Orlowski et al. | 530/307 |
| 4,639,511 | 1/1987 | Orlowski et al. | 530/307 |
| 4,703,106 | 10/1987 | Hirose et al. | 530/307 |
| 4,758,550 | 7/1988 | Cardinaux et al. | 514/12 |

FOREIGN PATENT DOCUMENTS 0330241  8/1989  European Pat. Off. .

Primary Examiner—Merrell C. Cashion, Jr.
Assistant Examiner—S. G. Marshall
Attorney, Agent, or Firm—Finnegan, Henderson, Farabow, Garrett & Dunner

[57] ABSTRACT

Novel polypeptide derivatives, acid-addition salts thereof and complexes thereof, having the activities for inhibiting bone calcium absorption, for lowering the blood level of calcium, as analgesics, for inhibiting secretion of the gastric juice.

Pharmaceutical composition can be prepared by formulating, at least one of the novel polypeptide derivatives, acid-addition salts thereof and complexes thereof, together with a proteolytic enzyme inhibitors and/or pharmaceutically acceptable acids.

The pharmaceutical composition are quite effective as agents for curing hypercalcemia, for curing Peget's disease, for curing osteoporosis, analgetic agent, antiulcerative agent and the like.

17 Claims, No Drawings

POLYPEPTIDE DERIVATIVES AND CALCIUM METABOLISM IMPROVING AGENT

FIELD OF THE INVENTION

The present invention relates to calcium metabolism improving agents. More particularly, the invention relates to novel polypeptide derivatives, acid-addition salts thereof and complexes thereof, having the activities for inhibiting bone calcium absorption (activity for inhibiting calcium isolation from the bone), the activity for lowering the blood level of calcium, the activity as an analgesic, and the activity for inhibiting secretion of the gastric juice. Also the invention relates to calcium metabolism improving agents containing, as the active ingredients, at least one of the novel polypeptide derivatives, acid-addition salts thereof and complexes thereof, together with a proteolytic enzyme inhibitors and/or pharmaceutically acceptable acids.

PRIOR ART

Calcitonins have widely been known chemically as polypeptide derivatives, which have the activity for lowering the blood level of calcium. The calcitonins may be obtained by extraction from the thyroid glands of human beings and other mammals, birds, and the branchiogenic organs of fishes and amphibious animals. Various types of calcitonins occur in nature, and they have different constitutive amino acids dependent on the difference of species as the sources. These calcitonins, being obtained from various natural sources, are polypeptides which consist of 32 constitutive amino acids, and such polypeptides have common chemical structures in that the first and the seventh amino acids are both L-cysteines and the mercapto groups in said L-cysteines form disulfide bonding and, furthermore, it is common in that the terminal carboxyl group exists in each of said polypeptides forms as a prolinamide.

However, the disulfide bonding occurring in each of these natural calcitonins is presumably quite unstable in a solution, therefore, when such calcitonins are used as agents for curing various symptoms caused by an extraordinary high blood level of calcium such as hypercalcemia, and for curing Paget's disease, osteoporosis and the like, then there may occur a lowering of the physiological activities of calcitonins and the appearance antigenecity caused by the by-produced substances formed therefrom.

Calcitonins are, generally, decomposed in the digestive tract because they are peptide compounds, and they are hardly absorbed from the digestive organs because they are high-molecular weight compounds. For these reasons, calcitonins can only be administered, as to pharmaceutical preparations, in the form of injection preparations such as intramuscular injection preparations and intravenous injection preparations. However, by using such injection preparations, it is difficult to conduct medical treatments out-side of hospital by using said injection preparations. Thus, a patient who has to have medical treatment by using calcitonins is required to go to a hospital (as an out-patient) at every administration of the injection, and thus such problems cause the restriction of use of calcitonins as pharmaceutical preparations.

In recent years, there have been reported a number of synthetic calcitonins having the chemical structures similar to those of the above-mentioned natural calcitonins. Among these synthetic calcitonins, there are involved polypeptides having the amino acid sequence based on that in the natural salmon calcitonins in which the above-mentioned disulfide bonding is replaced with a lower alkylene bonding by deactivating the first cysteine in the amino acid sequence, and at the same time by replacing the seventh cystein in the amino acid sequence with an α-amino acid having the specific lower alkylene group, and the carboxyl group of the side-chain in said α-amino acid is subjected to ring-closure with the amino group of the second serine in the amino acid sequence so as to form the above-mentioned alkylene bonding. [Cf. Japanese Patent Kokai (Laid-open) No. 51-128993 (1976) (Corresponding to U.S. Pat. No. 4,086,221) and Japanese Patent Kokai (Laid-open) No. 61-112099 (1986)] However, it has been reported that the above-mentioned disulfide bonding which in these natural calcitonins is essential for the manifestation of their physiological activities, so that the stability of said synthetic polypeptides having no such disulfide bonding may be improved to some extent as compared with the stability of the corresponding natural type calcitonins, but such synthetic polypeptides have the tendency for lowering their physiological activities as compared with the fundamental physiological activities shown by the corresponding natural type calcitonins.

SUMMARY OF THE INVENTION

An object of the present invention is to provide novel synthetic polypeptides, i.e., novel calcitonin derivatives which do not have the above-mentioned disulfide bonding so as to avoid the instability thereof, furthermore, by improving the fundamental physiological activities of the corresponding natural calcitonins, i.e., the activity for lowering the blood level of calcium, the activity as analgesic, as well as the activity for inhibiting the secretion of the gastric juice, so that these synthetic calcitonins are quite effective as agents for curing hypercalcemia, Paget's disease, osteoporosis, analgetic agents, anti-ulcerative agents and the like.

Another object of the present invention is to provide process for preparing said synthetic polypeptides.

A further object of the present invention is to provide a pharmacological composition containing, as the active ingredient, at least one of the synthetic polypeptide derivatives represented by the general formulae (1) and (2) mentioned below, together with a proteolytic enzyme inhibitor and/or pharmaceutically acceptable acids.

The present inventors have made an extensive study to achieve the above-mentioned objectives of a present invention, and as the result they have successfully synthesized the novel polypeptide derivatives having the specific chemical structural formulas represented by the general formula (1) and (2), and further they have found that such novel polypeptide derivatives possess excellent properties to meet the requirements as medicines as mentioned in the above described objects, so that the present invention has been completed.

DETAILED EXPLANATION OF THE INVENTION

The present invention relates to polypeptide derivatives, acid-addition salts thereof and complexes thereof represented by the general formula (1),

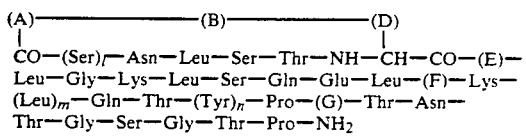

$$(A)\text{——————}(B)\text{—————}(D) \quad (1)$$
$$|\qquad\qquad\qquad\qquad\qquad |$$
$$CO-(Ser)_l-Asn-Leu-Ser-Thr-NH-CH-CO-(E)-$$
Leu—Gly—Lys—Leu—Ser—Gln—Glu—Leu—(F)—Lys—
(Leu)$_m$—Gln—Thr—(Tyr)$_n$—Pro—(G)—Thr—Asn—
Thr—Gly—Ser—Gly—Thr—Pro—NH$_2$ wherein (A) is a lower alkylene group; (B) is —NH-CO—, —S— or an oxyphenylene group; (D) is a lower alkylene group; (E) is a valine residue, a glycine residue or an isoleucine residue; (F) is a histidine residue, an asparagine residue, a glycine residue, an alanine residue, a serine residue, a leucine residue or a glutamine residue; and (G) is an arginine residue or a glutamine residue, respectively; each of l, m and n is 0 or 1; provided that, when l is 0 and (A) is a methylene group, then (D) is a methylene group or an ethylene group, or by the general formula (2),

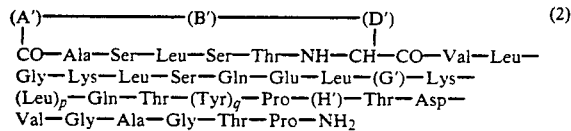

$$(A')\text{——————}(B')\text{—————}(D') \quad (2)$$
$$|\qquad\qquad\qquad\qquad\qquad |$$
$$CO-Ala-Ser-Leu-Ser-Thr-NH-CH-CO-Val-Leu-$$
Gly—Lys—Leu—Ser—Gln—Glu—Leu—(G')—Lys—
(Leu)$_p$—Gln—Thr—(Tyr)$_q$—Pro—(H')—Thr—Asp—
Val—Gly—Ala—Gly—Thr—Pro—NH$_2$ wherein (A') is a lower alkylene group; (B') is a group of —NHCO—; (D') is a lower alkylene group, (G') is a histidine residue, an aspartic acid residue or a glycine residue; and (H') is an arginine residue or a glutamine residue, respectively; each of p and q is 0 or 1.

In the present specification, amino acids, peptides, protecting groups, active groups and the like are illustrated by their abbreviations and their symbols which are indicated under the provisions of IUPAC (International Union of Pure and Applied Chemistry) and of IBU (International Union of Bio-chemistry) or by symbols being used commonly in the art. In connection with describing the optical isomers of amino acids, generally L-form (levo-form) of the isomers will be mentioned unless otherwise specified. Examples of such abbreviations and symbols are shown as follows:

| | | |
|---|---|---|
| Ala: alanine | β-Ala: β-alanine | Arg: arginine |
| Asp: aspartic acid | Asn: asparagine | Cys: cysteine |
| Gln: glutamine | Glu: glutamic acid | Gly: glycine |
| His: histidine | Ile: isoleucine | Leu: leucine |
| Lys: lysine | Pro: proline | Thr: threonine |
| Ser: serine | Val: valine | Tyr: tyrosine |
| Bzl: benzyl group | Bu$^t$: tert-butyl group | |
| Boc: tert-butoxycarbonyl group OBzl: benzyloxy group | | |
| OSu: N-oxysuccinimide group ONp: p-nitrophenyloxy group | | |
| Z: benzyloxycarbonyl group | | |
| Cl-Z: o-chlorobenzyloxycarbonyl group | | |
| Tos: p-toluenesulfonyl group OEt: ethyloxy group | | |
| DCC: N,N'-dicyclohexylcarbodiimide | | |
| TFA: trifluoroacetic acid DMF: dimethylformamide | | |
| WSC: N-ethyl-N'-dimethylaminopropyl-carbodiimide | | |
| THF: tetrahydrofuran HOBT: 1-hydroxybenzotriazole | | |
| HOSu: N-hydroxysuccinimide | | |
| HONB: N-hydroxy-5-norbornene-2,3-dicarboximide | | |
| Acp: ε-aminocaproic acid Abu: γ-aminobutyric acid | | |
| Cpc: S-(3-carboxypropyl)cysteine | | |
| Cec: S-(2-carboxyethyl)cysteine OcHex: cyclohexyloxy group | | |
| Cl$_2$-Bzl: 2,6-dichlorobenzyl group | | |

In addition to the above, in the present specification, each of the groups being defined by the symbols of (A), (B) and (D) in the general formula (1), and by the symbols (A'), (B') and (D') in the general formula (2) and other groups are exemplified specifically as follows:

As to the lower alkylene group, a straight chain or branched chain alkylene group having 1 to 6 carbon atoms, such as methylene, ethylene, trimethylene, 1-methylethylene, tetramethylene, 2-trimethylene, pentamethylene and hexamethylene groups may be exemplified.

As to the oxyphenylene group, any one of oxy-o-phenylene, oxy-m-phenylene and oxy-p-phenylene groups may be exemplified.

As to the preferred examples represented by the formula

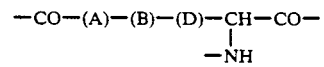

$$-CO-(A)-(B)-(D)-CH-CO-$$
$$|$$
$$-NH$$

in the above-mentioned general formula (1) and the formula

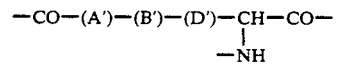

$$-CO-(A')-(B')-(D')-CH-CO-$$
$$|$$
$$-NH$$

in the above-mentioned general formula (2), there may be exemplified by the following group of the formulas:

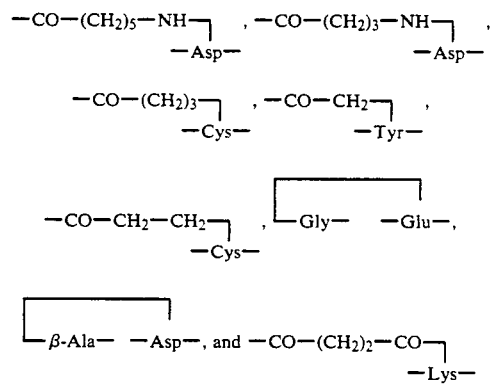

and the like.

The polypeptide derivatives, acid-addition salts thereof and complexes thereof represented by the above-mentioned general formula (1) according to the present invention possess excellent activities for lowering the blood level of calcium, activities as analgesic, activities for inhibiting the secretion of the gastric juice and other pharmacological activities over those shown by natural calcitonins on the basis of the specific chemical structures in each of these general formulas. In addition to the above, the stabilities of these polypeptide derivatives are considerably improved and even though under conditions of storing them in the state of solutions, the above-mentioned various pharmacological activities are not decreased. In addition to the above, the polypeptide derivatives according to the present invention have excellent long acting properties and absorbability, as well as fewer side-effects such as antigenicity, blood-sugar increasing activity, loss of body weight, inhibitory effects in intestinal movements, and decreasing food intake effect and the like, also they have low toxicity. Therefore, the polypeptide derivatives according to the present invention are quite effective as agents for curing various symptoms, for example bone Paget's disease, osteoporosis and the like, and analgetics as well as anti-ulcerative agents, thus in view of these features, the polypeptide derivatives, acid-addition salts thereof and complexes thereof according to the present invention are quite suitable compounds as the above-mentioned drugs.

Next, processes for preparing the polypeptide derivatives represented by general formulas (1) and (2) according to the present invention are explained in detail as follows.

The polypeptide derivatives represented by the above-mentioned general formulas (1) and (2) according to the present invention can be prepared basically by conventional methods for synthesizing polypeptides, for example, by a so-called "stepwise method", thus by condensing amino acids with the terminal amino acid stepwise according to the above-mentioned chemical structure in the amino acid sequence so as to prolong the amino bondings (peptide bondings) in sequence, or by first dividing the above-mentioned chemical structures of polypeptides into several fragments, then these divided fragments are synthesized and then by condensing the fragments. Thus, at first, a polypeptide chain corresponding to the above-mentioned chemical structure is prepared, then the free functional groups in the specific N-terminal amino acid being formed during the preparation of said polypeptide are combined with the side-chain functional group of the seventh amino acid or related compound thereof so as to make the desired polypeptide derivative by the ring-closure.

Among the related compounds of the seventh amino acid, some of them include novel compounds, and these related compounds can be prepared from a suitable protected amino acid and a halogenated compound corresponding thereto as the starting materials, by the methods as mentioned below. Thus, the hydroxyl group of Z-Tyr—$OCH_3$ or the mercapto group of HCl.H-Cys—$OCH_3$ is reacted with a halogenated lower alkyl carboxylic acid of which the carboxyl group is protected, in the presence of a basic compound in a suitable solvent. As to the basic compound used in this reaction, triethylamine; a metal hydride such as sodium hydride, potassium hydride, lithium hydride or the like; an inorganic basic compound such as potassium carbonate, sodium carbonate, potassium hydrogen carbonate, sodium hydroxide, potassium hydroxide or the like can be used; and as to the solvent, a halogenated hydrocarbon such as dichloromethane, carbon tetrachloride, chloroform, tetrachloroethane or the like; an ether such as dioxane, THF (tetrahydrofuran), dimethoxy ethane or the like; a ketone such as acetone, methyl ethyl ketone or the like; acetonitrile, ethyl acetate, DMF (dimethylformamide), dimethylacetamide, dimethyl sulfoxide or the like can be used. Each of these solvents is used preferably in an anhydrous state. The carboxyl group protecting group in the halogenated lower alkyl carboxylic acid which is to be reacted with the above-mentioned amino acid may be any group capable of forming a common ester, and as to the ester to be formed from such group, an alkyl ester (methyl, ethyl, propyl, butyl, tert-butyl or the like) or Bzl ester can be typically exemplified. As to the ratio of amounts of the starting materials used in the above reaction, there is not any specific restriction, and generally an equimolar quantity to 5 times the molar quantity, preferably an equimolar quantity to 1.5 times the molar quantity of the above-mentioned carboxylic acid may be used to the amino acid. The above reaction may be carried out generally at about 0° to 100° C., preferably at about room temperature to 60° C., and the reaction is completed generally in about 30 minutes to 120 hours.

As to methods to be employed for synthesizing the peptides as mentioned above, these are concretely described, for example, in "The Peptides" Vol. 1, (1979), pp. 66-100, Chapter 2, by Johan H. Jones, The Formation of Peptide Bonds, (Edited by Erhard Gross and Johannes Meienhofer, published from Academic Press, Inc., New York, N.Y., U.S.A.); and in "PEPTIDE-GOHSEI-NO-KISO-TO-JIKKEN" (Fundamentals and Experiments in the Synthesis of Peptides), by Izumiya, et al., published from Maruzen Publishing Co., Ltd., Tokyo, Japan. For example, azide method, acid chloride method, acid anhydride method, mixed acid anhydride method, DCC (N,N'-dicyclohexylcarbodiimide) method, activated ester methods (such as p-nitrophenyl ester method, N-hydroxysuccinimide method, cyanomethyl ester method, etc.), Woodward-K reagent method, carboxyl diimidazol method, oxidation-reduction method, DCC/additive (such as HONB, HOBT and HOSu) method and the like can be exemplified. In carrying out the above-mentioned methods, either solid phase synthesis method or liquid phase synthesis method can be employed. In the case, when the solid phase synthsis method is carried out, at the first step, a C-terminal amino acid (an amino acid in which the terminal amino group is protected) is coupled to an insoluble carrier through the carboxyl group thereof. As to the insoluble carrier, there is not any specific restriction thereto, and it can be selected from any material having a coupling ability to a reactive carboxyl group, for example, a halogenomethyl resin or the like, phenol resin, tert-alkyloxycarbonylhydrazide resin, benzhydrylamine resin, and the like can be used. Next, after the removal of amino-protecting group, then in accordance with the amino acid sequence represented by the above-mentioned general formulas (1) and (2), each one of the amino group protected-amino acids is coupled sequentially with another amino group protected-amino acid by condensing the reactive amino group with the reactive carboxyl group through condensation reactions (peptide bonding formation reaction and acid-amide bonding formation reaction, hereinafter referred to simply as "condensation"), so as to synthesize the polypeptide by means of a stepwise method and to extend the chain length thereof suitably within the 32nd to 8th positions in the whole amino acid sequence and, then the thus obtained polypeptide is coupled to another polypeptide which corresponds to the remaining portion of the polypeptide of the present invention, which is synthesized separately by a method such as a liquid phase synthesis method, and thus the prepared polypeptide represented by the general formula (1) or (2) is obtained by removing the insoluble carrier to yield the desired corresponding polypeptide. The desired ring-formation reaction of polypeptide according to the present invention is carried out by an acid amide formation reaction method similar to that employed in the above-mentioned condensation reaction.

In carrying out the above-mentioned various methods, the amino acids, for example Arg, Tyr, Glu, Thr, Asp, Lys, His, Ser and the like, having the side-chain functional group may preferably be protected by means of protecting their side-chain functional groups by using conventional protecting groups, then said protecting groups can be removed after the completion of the above-mentioned reactions. The functional groups relating to the above-mentioned reactions are usually activated. Each of these reactions is known in the art and the reagents being used therein may be selected suitably from known reagents.

For example, as to groups for protecting the amino group, there may be exemplified benzyloxycarbonyl, tert-butoxycarbonyl, tert-amyloxycarbonyl, isobornyloxycarbonyl, p-methoxybenzyloxycarbonyl, 2-chlorobenzyloxycarbonyl, adamantyloxycarbonyl, trifluoroacetyl, phthalyl, formyl, o-nitrophenylsulfenyl, diphenylphosphinothioyl and 9-fluorenylmethoxycarbonyl groups and the like.

As to groups for protecting the carboxyl group, any groups capable of forming, for example, alkyl esters (chain- or cyclic-alkyl esters, such as methyl, ethyl, propyl, butyl, tert-butyl and cyclohexyl esters, and the like), Bzl ester, p-nitrobenzyl ester, p-methoxybenzyl ester, p-chlorobenzyl ester, benzhydryl ester, benzyloxycarbonylhydrazide, tert-butyloxycarbonylhydrazide and tritylhydrazide and the like can be exemplified.

As to groups for protecting the guanidino group of Arg, there may be exemplified p-toluenesulfonyl, nitro, benzyloxycarbonyl and amyloxycarbonyl groups and the like.

The hydroxyl groups of Ser and Thr can be protected by means of esterification or etherification method, but they may not necessarily be protected. As to groups suitable for esterifying the hydroxyl groups, there may be exemplified lower alkanoyl groups such as acetyl group and the like, aroyl groups such as benzoyl group and the like, and groups derived from carbonic acid such as benzyloxycarbonyl, ethyloxycarbonyl groups and the like. Further, as to groups suitable for etherifying the hydroxyl groups, there may be exemplified benzyl, tetrahydropyranyl, tert-butyl groups and the like.

As to groups for protecting the hydroxyl group of Tyr, there may be exemplified benzyl, 2,6-dichlorobenzyl, benzyloxycarbonyl, acetyl, and p-toluenesulfonyl groups and the like.

As to groups for protecting the side-chain amino group of Lys, there may be exemplified benzyloxycarbonyl, 2-chlorobenzyloxycarbonyl, 2,6-dichlorobenzyloxycarbonyl, Boc and p-toluenesulfonyl groups and the like.

As to groups for protecting the imino group of His, there may be exemplified p-toluenesulfonyl and Bzl groups and the like.

The protection of the carboxyl groups of Asp and Glu may be carried out by esterifying with an alcohol for example benzyl alcohol, methanol, ethanol, tert-butyl alcohol, and cyclohexyl alcohol and the like.

As to the activated carboxyl groups, there may be exemplified the corresponding acid chloride, acid anhydride or mixed acid anhydride, azide, activated ester (esters of pentachlorophenol, p-nitrophenol, N-hydroxysuccinimide, 1-hydroxybenzotriazole and N-hydroxy-5-norbornene-2,3-dicarboxyimide and the like).

In the above-mentioned method, the condensation of the reactive amino group with the reactive carboxyl group can be carried out in the presence of a basic compound, in a suitable solvent. As to the suitable basic compound, an organic basic compound such as triethylamine, trimethylamine, N,N-diisopropylethylamine, pyridine, dimethylaniline, N-methylmorpholine, 1,5-diazabicyclo[4,3,0]-5-nonene [DBN], 1,5-diazabicyclo[5,4,0]-5-undecene [DBU], 1,4-diazabicyclo[2,2,2]octane [DABCO] and the like; an inorganic basic compound such as potassium carbonate, sodium carbonate, potassium hydrogen carbonate, sodium hydrogen carbonate and the like can be used. As to the solvent, any solvent which is known as a suitable solvent for this type of condensation reaction, for example anhydrous or water-containing DMF, dimethyl sulfoxide (DMSO), pyridine, chloroform, dioxane, dichloromethane, THF, ethyl acetate, N-methylpyrrolidone and hexamethylphosphoric triamide (HMPA) and the like and mixed solvents thereof can be used. As to the ratio of amounts of the starting materials used in this reaction, there is not any specific restriction thereto, and generally, an equimolar to 5 times the molar quantity, preferably an equimolar to 1.5 times the molar quantity of one starting material to another starting materials may be used. The reaction temperature may be within usual temperature range being employed in this type of condensation reaction, and generally it is selected suitably from the range of about $-40°$ C. to about $60°$ C., preferably, from about $-20°$ C. to about $40°$ C. The reaction may generally be carried out within about several minutes to 120 hours.

Among the above-mentioned condensation reactions, mixed acid anhydride method is carried out in a suitable solvent, in the presence of a basic compound, by using an alkyl halocarboxylic acid for example methyl chloroformate, methyl bromoformate, ethyl chloroformate, ethyl bromoformate, isobutyl chloroformate and the like. As to the basic compound, an organic basic compound such as triethylamine, trimethylamine, N,N'-diisopropylethylamine, pyridine, dimethylaniline, N-methylmorpholine, DBN, DBU and DABCO and the like, an inorganic basic compound such as potassium carbonate, sodium carbonate, potassium hydrogen carbonate, and sodium hydrogen carbonate can be used. Further, as to the solvent, any solvent which may be used for such mixed acid anhydride method, for example a halogenated hydrocarbon such as methylene chloride, chloroform, dichloroethane and the like, an aromatic hydrocarbon such as benzene, toluene, xylene and the like, an ether such as diethyl ether, THF, dimethoxyethane and the like, an ester such as methyl acetate, ethyl acetate and the like, an aprotic polar solvent such as DMF, DMSO, HMPA and the like may be used. The reaction is carried out, generally under conditions of about $-20°$ to $100°$ C., preferably at about $-20°$ to $50°$ C., and is completed, generally within several minutes to about 10 hours, preferably in about several minutes to about 2 hours.

In explaining the above-mentioned azide method in detail, this method of reaction is carried out at first, by activating the carboxyl group of the amino acid with an alcohol such as methyl alcohol, ethyl alcohol, benzyl alcohol or the like, then thus obtained activated carboxyl group is reacted with hydrazine hydrate in a suitable solvent to obtain the desired azide compound. As to the solvent, dioxane, DMF, DMSO, HMPA, an alcohol or a mixed solvent thereof can be used. The amount of hydrazine hydrate is generally about 5 to 20 times the molar quantity, preferably 5 to 10 times the molar quantity thereof to the activated carboxyl group. The reaction is generally carried out at temperature below $50°$ C., preferably at $-20$ to $30°$ C., so as to obtain a compound (hydrazine derivative) in which the carboxyl group portion is substituted with hydrazine. Further, a compound in which the carboxyl group portion is substituted with azide can be prepared by reacting the above-mentioned hydrazine derivative with a nitrous acid compound in the presence of an acid in a suitable solvent. As to acid used in this reaction, hydrochloric acid can be used typically, and as to the nitrous acid compound, sodium nitrite, isoamyl nitrite, nitrosyl chloride or the like can be used. Said nitrous acid compound may be used in an amount generally about an equimolar to 2 times the molar quantity, preferably about an equimolar to 1.5 times the molar quantity to the hydrazine compound. The reaction is generally carried out at about $-20°$ to $0°$ C., preferably at about $-20°$ to $-10°$ C., and is completed in about several minutes to 30 minutes.

The above-mentioned various condensation reactions may be carried out in the presence of a suitable condensing agent, for example a carbodiimide reagent such as DCC, WSC, WSC.HCl or the like; N,N'-carbonyldiimidazole, tetraethylpyrophosphine or the like. Said condensing agent is used in an amount of an equimolar to about 4 times the molar quantity to the starting material. The above-mentioned reaction using said condensing agent is carried out in a suitable solvent for example a halogenated hydrocarbon such as dichloromethane, chloroform, carbon tetrachloride, tetrachloroethane or the like; an ether such as dioxane, THF, dimethoxyethane or the like; a ketone such as acetone, methyl ethyl ketone or the like; acetonitrile, ethyl acetate, DMF, dimethylacetamide, DMSO or the like, preferably an anhydrous solvent thereof, and at reaction temperature of about, generally $-10°$ to $60°$ C., preferably about $0°$ C. to room temperature, and in about several ten minutes to 120 hours.

In the above-mentioned various reaction steps and in the final reaction step, when the protecting group is removed necessarily, said removal reactions can be carried out by method similar to those employed in usual reactions for removal of protecting groups. As to the method for removal of the protecting groups, hydrogenation by using a catalyst such as palladium-carbon, palladium black or the like; reducing method by using sodium metal as the reducing agent in a liquid ammonia; removal reaction under a basic condition by using piperidine or the like; and acidolysis by using a strong acid such as trifluoroacetic acid, hydrochloric acid, hydrogen methanesulfonic acid, hydrobromic acid or the like can be exemplified.

In carrying out of the hydrogenation by using the above-mentioned catalyst, the reaction can be conducted under conditions of 1 atmospheric hydrogen pressure, at about $0°$ to $40°$ C., and the amount of the catalyst may be used generally within the range of about 100 mg to 1 g, and the reaction can be completed in about 1 hour to several days. The above-mentioned acidolysis can be carried out in the presence of a solvent, and generally at about $-40°$ to $60°$ C., preferably at about $-20°$ to $20°$ C., for about several minutes to several hours. The amount of the acid used in the acidolysis may be generally a large excess quantity to the starting material. In carrying out of the acidolysis when the only protecting group of the amino group is removed, trifluoroacetic acid or hydrochloric acid is preferably used as the acid. Furthermore, in carrying out of the reduction by use of sodium metal in an aqueous ammonia, the reduction is carried out by using sodium metal in an amount that the reaction mixture keeps permanent blue in color for about 30 seconds to 10 minutes, and generally at about $-40°$ to $-70°$ C.

In the present invention, chain structural polypeptide derivatives are prepared by the above-mentioned condensation reactions, as well as follows by said preparation step for obtaining such polypeptides, or on the way of said step, it is important to employ the specific cyclization reaction process step in accordance with similar condensation reaction, thus ring closing reaction of the free functional group of N-terminal amino acid formed in the preparation step of the above-mentioned polypeptides, with the side-chain functional group of the 7th amino acid or its related compound.

As to one of the preferable examples of preparation of the polypeptide derivatives according to the present invention is that, for example as illustrated in Example 1 below-mentioned, at the first a protected polypeptide

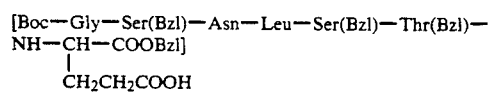

is corresponding to 1st to 7th amino acid sequence counted from the N-terminal is prepared, then this product is converted into an activated ester by adding TFA-ONp in dried pyridine, next it is subjected to removal of Boc group by using TFA, then thus obtained protected peptide

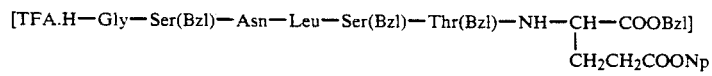

is dissolved in DMF, and the solution thus obtained is added dropwise into a large amount of dried pyridine at $50°$ C., under vigorous stirring condition for several hours, further the mixture is stirred for additional several hours to obtain the desired cyclized protected peptide, next a peptide of the 8th to 10th position in the amino acid sequence is condensed by means of fragment condensation to obtain the protected decapeptide.

On the other hand, a protected peptide of the 11th to 32nd amino acid in the amino acid sequence is synthesized by the stepwise method or a fragment condensation method, then this is coupled to the previously prepared protected decapeptide, and then is subjected to removal reaction of the protecting group.

The thus obtained polypeptides prepared by various methods as mentioned above can be separated and purified by methods usually employed in separation of peptides, for example, solvent extraction method, distribution method, column chromatography method and the like. The desired polypeptide derivatives represented by the general formula (1) and the general formula (2) according to the present invention can be thus obtained.

The polypeptide derivatives thus obtained according to the present invention are generally in the form of free bases or salts thereof, and also have biological activities similar to those shown by the corresponding original natural polypeptides, and thus they are useful as various pharmaceutical preparations. Thus, they are converted into pharmaceutical acceptable acid-addition salts or complexes thereof by means of conventional methods. The examples of said acids for preparing the above-mentioned acid-addition salts include inorganic acids such as hydrochloric acid, hydrobromic acid, sulfuric acid, phosphoric acid and the like; organicacids such as formic acid, acetic acid, propionic acid, glycolic acid, lactic acid, pyruvic acid, oxalic acid, succinic acid, malic acid, tartaric acid, citric acid, benzoic acid, salicylic acid, a lower alkanesulfonic acid, benzenesulfonic acid, toluenesulfonic acid and the like. The above-mentioned complexes can be prepared by adding a certain types of inorganic or organic substance which gives long-acting property to the polypeptides. The examples of such inorganic substances to be used for the formation of such complexes include inorganic compounds which are derived from metals such as calcium, magnesium, cobalt, zinc and the like, particularly, phosphates, pyrophosphates, polyphosphates of these metals which are salts thereof having slight solubility, and hydroxide thereof; and other inorganic compounds such as polyphosphates of alkali metals. Further, the examples of said organic materials include non-antigenic gelatin, CMC (carboxymethyl cellulose), phosphoric acid esters or sulfonic acid esters of alginic acid, dextran, polyalcohol phytic acid, polyglutamic acid, protamine and the like.

It is important for the calcium metabolism improving agents of the present invention in that at least one of the polypeptide derivatives represented by the general formulas (1) and (2), acid-addition salts thereof and complexes thereof is used together with a proteolytic enzyme inhibitor and/or pharmaceutically acceptable acid. As to these proteolytic enzyme inhibitors to be used, the examples including, trypsin inhibitors [Cf. Life Science, Vol. 31, pp. 2837, (1982); Biochemical Pharmacology, Vol. 36, pp. 1035, (1987); IGAKU-NO-AYUMI (Progress of the Medicine), Vol. 138, pp. 59, (1986)], chymotrypsin inhibitors [Japanese Patent Kokai (Laid-open) No. 58-225080 (1983); The Journal of Biochemistry, Vol. 95, pp. 319, (1984); Biochemistry, Vol 2, pp. 252, (1963); Biochemistry, Vol. 2, pp. 252, (1963); Journal of the American Chemical Society, Vol. 93, pp. 2351, (1971); Journal of Pharmacy and Pharmacology, Vol. 32, pp. 182, (1980); and The Journal of Antibiotics, Vol. 23, pp. 425, (1970). As to the specific examples of the above-mentioned proteolytic enzyme inhibitors, examples including Chymostatin, Leupeptin, Antipain, Soybean trypsin inhibitors (e.g., type I-S, such as SBTI, manufactured by Sigma & Co.), Aprotinin, N-α-p-tosyl-L-lysine chloromethyl ketone, Gabexate mesylate, Urinastatin, Nafamostat mesylate, FK-448 [a trademark for 4-(4-isopropylpiperazinocarbonyl)phenyl 1,2,3,4-tetrahydro-1-naphthatemethanesulfonate, manufacture by Kowa Corp.] and the like.

As to the pharmaceutically acceptable acids to be used together with the polypeptide derivative represented by the general formulas (1) and/or (2), the examples including usual organic acids, inorganic acids and salts thereof. Specifically, they are inorganic acids, such as hydrochloric acid, hydrobromic acid, sulfuric acid, phosphoric acid and the like; organic acids , such as formic acid, acetic acid, propionic acid, glycolic acid, lactic acid, pyruvic acid, oxalic acid, succinic acid, malic acid, tartaric acid, citric acid, benzoic aicd, salicylic acid, lower alkanesulfonic acids, benzensulfonic acid toluenesulfonic acid, ascorbic acid, acidic amino acid, fatty acids and the like and the salts thereof; for example, sodium lactate, potassium lactate, sodium citrate, potassium citrate, sodium tartarate, sodium salicylate, sodium ascorbate, and the like can be exemplified. Furthermore, as to the acidic amino acids, glutamic acid, pyroglutamic acid, aspartic acid and the like can be exemplified.

As to the unsaturated fatty acids, oleic acid, linoleic acid, linolenic acid, arachidonic acid and the like can be exemplified. Among those acids, generally organic acids, specifically solid form organic acids are preferable, particularly weak acids are more preferably used.

The ratio of amount of the above-mentioned proteolytic enzyme inhibitor and the pharmaceutically acceptable acids to the amount of polypeptide derivative represented by the general formula (1) or (2) is not specifically restricted, and can be selected from a wide range, generally, the proteolytic enzyme inhibitors may be used in the range of about 500 times to $1 \times 10^6$ times parts by weight (or moles), preferably about 1,500 times to $3 \times 10^5$ times parts by weight thereof to one part of the polypeptide derivative represented by the general formula (1) or (2). Similarly, the pharmaceutically acceptable acid may be used in the range of about 1,000 times to $1 \times 10^6$ times parts by weight (or moles), perferably about 5,000 times to $2 \times 10^5$ times parts by weight thereof to one part of the polypeptide derivative represented by the general formula (1) or (2).

The absorbability, particularly intra-intestinal absorbability of the polypeptide derivative represented by the general formula (1) or (2) can be considerably accelarated by using it together the proteolytic enzyme inhibitors and pharmaceutically acceptable acids, so that the activity for lowering the concentration of calcium in the blood can be further improved. The effect for accelaration of intraintestinal absorption performed by the polypeptide derivative represented by the general formula (1) and (2) can be clearly seen when any one or both the proteolytic enzyme inhibitors and pharmaceutically acceptable acids are used together with the polypeptide derivatives represented by the general formula (1) and/or (2), and the synergistic effects can be seen when three components, i.e., both of proteolytic enzyme inhibitor and pharmaceutically acceptable acid together with the polypeptide derivatives represented by the general formula (1) and/or (2) are used in combination therewith.

The calcium metabolism improving agents according to the present invention are prepared by formulating the polypeptide derivative represented by the general formula (1) and/or (2) together with at least one of the proteolytic enzyme inhibitors and pharmaceutically acceptable acids into a single and the same pharmaceutical preparation so as to contain these individual ingredients in the same preparation form, said pharmaceutical preparation may be administered, or by formulating each one of these ingredients individually to prepare a single pharmaceutical preparation, and administer each one of individual pharmaceutical preparations, containing singly each of the ingredients, together upon use. In each of the cases, the above-mentioned pharmaceutical preparations can be prepared by using usual diluents or excipients such as fillers, bulking agents, binders, wetting agents, disintegrating agents, surface active agents, lubricants and the like. As to the form of pharmaceutical preparations, any type of form may be selected from a wide range thereof dependent on the purpose of curing, and the examples of pharmaceutical compositions including tablets, pills, powders, liquids, suspensions, emulsions, granules, capsules, suppositories, nasal drops, oral mucosal absorption type preparations (e.g., troches, buccals, sublingual tablets, chewable tablets and drops and the like), eye lotions, ointments and the like.

For the purpose of shaping the pharmaceutical preparations in the form of tablets, carriers which are widely used in this field can be used, for example excipients such as lactose, sucrose, sodium chloride, glucose, urea, starch, calcium carbonate, kaolin, crystalline cellulose, silicic acid and the like; binding agents such as water, ethyl alcohol, propanol, simple syrup, glucose solutions, starch solutions, gelatin solutions, carboxymethyl cellulose, shelac, methyl cellulose, potassium phosphate, polyvinylpyrrolidone, and the like; disintegrators such as dried starch, sodium alginate, agar-agar powder, laminalia powder, sodium hydrogen carbonate, calcium carbonate, esters of polyoxyethylenesorbitan fatty acids, sodium laurylsulfate, monoglycerides of stearic acid, starch, lactose and the like; desintegration inhibitors such as sucrose, stearin, coconut butter, hydrogenated oils and the like; absorption accelerators such as quarternary ammonium bases, sodium laurylsulfate and the like; wetting agents such as glycerin, starch and the like; adsorbing agents such as starch, lactose, kaolin, bentonite, colloidal silicic acid and the like; and lubricants such as purified talc, stearic acid sats, boric acid powder, polyethylene glycols and the like. In case of preparing the tablets, they can be further coated with usual coating materials to make them as sugar coated tablets, gelatin film coated tablets, tablets coated with enteric coatings, tablets coated with films or double layered tablets and multi-layered tablets.

For the purpose of shaping the pharmaceutical preparations in the form of pills, carriers which are known and widely used in this field can also be used, for example, excipients such as glucose, lactose, starch, coconut butter, hydrogenated vegetable oils, kaolin, talc and the like; binding agents such as powdered gum arabi, powdered tragacanth gum, gelatin, ethnaol and the like; and desintegrators such as laminalia, agar-agar and the like are included.

For the purpose of shaping the pharmaceutical preparations in the form of suppositories, carriers which are known and widely used in this field can also be used, for example, polyethylene glycols, coconut butter, higher alcohols, esters of higher alcohols, gelatin, semisynthesized glycerides and the like are included.

For the purpose of shaping the pharmaceutical preparations in the form of capsule preparations, the active ingredients (polypeptide derivatives of the present invention and proteolytic enzyme inhibitors as well as pharmaceutically acceptable acids) are mixed with the above-mentioned carriers, and thus obtained mixture is filled in solid gelatin capsules or in soft capsules to prepare capsule preparations.

For the purpose of shaping the pharmaceutical preparations in the form of injection preparations, solutions, emulsions or suspensions of these active ingredients are sterilized and are preferably isotonic to blood, and in making them in these forms, diluents for example water, ethyl alcohol, Macrogol (polyethylene gglycols), polypropylene glycol, ethoxylated isostearyl alcohol, polyoxylated isostearyl alcohol, and polyoxyethylenesorbitan fatty acid esters, and the like can be used. In these cases, adequate amounts of sodium chloride, glucose or glycerin can be added to the desired preparations for the purpose of to make them isotonic to the blood, furthermore, usual dissolving agents, buffers, analgesic agents, and the like may be added. In addition to the above, coloring agents, preservatives, perfumes, seasoning agents, sweeting agents as well as other medicaments can also be added into the desired injection preparations.

For the purpose of shaping the pharmaceutical preparations in the form of pastes, creams and gels, diluents which are known and widely used in these fields can also be used, for example, white petrolatum, paraffin, glycerin, cellulose derivatives, polyethylene glycols, silicones, bentonite and the like are included.

For the purpose of shaping the pharmaceutical preparations in the form of nasal drop preparations and in the form of oral mucosal absorption type preparations, they can be prepared by using suitable binding agents, diluents, propellants and the like by means of usual methods to make them powder form, aerosol form and liquid form so as to apply these prepararions by nebulization and spraying administrations. In preparing the above-mentioned powder form products, it is preferable to use water absorbing materials such as cellulose, starch, polyacrylates and the like. In preparing the above-mentioned aerosol form products, it is preferable to use water, glycols, alcohols, non-ionic surface active agents and the like. In preparing the above-mentioned spray-propellant type form products, they can be made by using a liquified petroleum gas, carbon dioxide gas, fluorinated lower alkanes as the proppelants.

The amounts of the active ingredients to be contained in the calcium metabolism improving agents of the present invention are not specifically restricted and can be selected from a wide range and, generally the polypeptide derivative represented by the general formula (1) or (2) may be contained in the range of 1 $\mu$g to 1 mg in the pharmaceutical preparation, and proteolytic enzyme inhibitors and pharmaceutically acceptable acids may be contained in the range of 100 mg to 2 g in the pharmaceutical preparation.

Methods for administering the above-mentioned pharmaceutical preparations are not specifically restricted, and they can be selected dependent on each of their preparation forms, the age of the patient, distinction of sex and other conditions, degree of the symptoms and the like. For example, tablets, pills, liquids, suspensions, emulsions, granules and capsules are administered orally, injection preparations are administered intravenously singly or are mixed with injection transfusions such as glucose solutions and amino acids solutions, and if necessary the injection preparations are administered singly intramuscularly, intracutaneously, subcutaneously or intraperitoneally. The suppositories are administered into rectum. The nasal drops are administered in nasal cavity by inhalation and the like, further, oral mucosal absorption type preparations are administered to oral mucosa.

The dosage of the above-mentioned pharmaceutical preparations are suitably selected depending on the methods of usages, the age of the patient, distinction of sex and other conditions, degree of the symptoms, and usually they are administered so as to give in an amount of about 20 ng to 20$\mu$g per kg of the body weight per day of the polypeptide derivative represented by the general formula (1) or (2), and such pharmaceutical preparations can be administered separately in 1 to 4 times a day.

EFFECTS OF THE INVENTION

According to the present invention, there can be provided pharmaceutical preparations, containing calcitonin derivative (polypeptide derivative), and particularly there are provided calcium metabolism improving agents, containing novel calcitonin derivative, which possess excellent activities for inhibiting the absorption of bone calcium, for lowering the concentration of calcium in the blood, as well as possessing excellent activity as analgesic and activity for inhibiting the secretion of the gastric juice. These pharmacological activities can be performed with less side-effects. In addition to the above, the polypeptide derivatives of the present invention are stable even in the state of solutions, so that they possess good absorbability for intra-intestinal (small intestine and rectum) administration, and furthermore, the polypeptide derivatives have good absorbability to mucous membrane of nose and mucous membrane of mouth.

The polypeptide derivatives of the present invention have several excellent features, i.e., (1) high solubility in water, (2) good absorbability, (3) good long-acting property, (4) good stability, (5) strong pharmacological activities, (6) low toxicity, (7) low antigenecity and (8) low activity for inhibiting appetite, and thus the polypeptide derivatives of the present invention can be used in several pharmaceutical applications due to the above-mentioned excellent features.

Next, in order to explain the present invention in more detail, examples for preparing raw material compounds from which the polypeptide derivatives of the present invention are prepared, are explained as Reference Examples, and then examples for preparing the polypeptide derivatives of the present invention are explained as Examples.

Furthermore, Pharmacological Tests on the polypeptide derivatives of the present invention are mentioned.

In each example, the amino acid analysis was conducted by adding 6N hydrochloric acid (to which phenol was added) to a test compound, hydrolysing the test compound at 110° C. for 24 hours or 48 hours, subjecting the reaction mixture to vacuum drying and the resultant residue was subjected to analysis by an amino acid analyzer.

REFERENCE EXAMPLE 1

Preparation of Boc-Thr-(Bzl)-Glu-OBzl

To a solution of 2.83 g of H-Glu-OBzl dissolved in 40 ml of acetonitrile were added 3.3 ml of triethylamine and 5.00 g of Boc-Thr(Bzl)-OSu under ice-cooling. The mixture was stirred overnight at room temperature. The reaction mixture was concentrated under reduced pressure. The residue was dissolved in 50 ml of ethyl acetate and the resulting solution was washed with 30 ml of water twice. The ethyl acetate layer was dried with anhydrous magnesium sulfate. The solvent was removed by distillation to dry the ethyl acetate layer, whereby 5.50 g (yield: 87.2%) of the above objective compound was obtained as a powder form product.

REFERENCE EXAMPLE 2

Preparation of Boc-Ser(Bzl)-Thr(Bzl)-Glu-OBzl.H$_2$O 5.50 Grams of Boc-Thr(Bzl)-Glu-OBzl was dissolved in 15 ml of TFA with ice-cooling. The mixture was stirred for 30 minutes at room temperature. The reaction mixture was concentrated under reduced pressure. The residue was subjected to vacuum drying over sodium hydroxide.

The resulting product was dissolved in 50 ml of acetonitrile and then neutralized with triethylamine with ice-cooling. Thereto was added 4.20 g of Boc-Ser(Bzl)-OSu and the mixture was stirred overnight at room temperature. The reaction mixture was concentrated under reduced pressure. The residue was dissolved in 50 ml of ethyl acetate. The ethyl acetate layer was washed with 20 ml of 1N hydrochloric acid twice and then with 20 ml of water twice. The ethyl acetate layer was then concentrated under reduced pressure. The residue was washed with n-hexane to obtain 6.90 g (yield: 91.6%) of the above objective compound as a powder form product.

Elemental analysis (C$_{38}$H$_{47}$N$_3$O$_{10}$.H$_2$O):
Calculated (%): C 63.06, H 6.82, N 5.81;
Found (%): C 63.33, H 6.60, N 5.80
Amino acid analysis:
  Thr: 0.98 (1)
  Ser: 0.93 (1)
  Glu: 1.09 (1)

REFERENCE EXAMPLE 3

Preparation of Boc-Asn-Leu-OEt 5.00 Grams of H-Leu-OEt.HCl, 5.95 g of Boc-Asn-OH and 4.11 g of HOBT.H$_2$O were suspended in 100 ml of THF. To this suspension was added 4.70 ml of WSC with ice-cooling. The mixture was stirred for 7 hours at room temperature. To the reaction mixture were added 100 ml of ethyl acetate and 200 ml of water to effect extraction. The ethyl acetate layer was washed with 50 ml of a saturated aqueous sodium bicarbonate solution three times, 50 ml of a saturated aqueous sodium chloride solution once, 50 ml of 1N hydrochloric acid three times and 50 ml of a saturated aqueous sodium chloride solution once in this order, dried with anhydrous magnesium sulfate and concentrated under reduced pressure. The residue was solidified with isopropyl ether to obtain 7.00 g (yield: 72.9%) of the above objective compound. Melting point: 155°–157° C.

REFERENCE EXAMPLE 4

Preparation of Boc-Ser(Bzl)-Asn-Leu-OEt 6.90 Grams of Boc-Asn-Leu-OEt was dissolved in 25 ml of TFA with ice-cooling. The mixture was stirred for 30 minutes at room temperature. The reaction mixture was concentrated under reduced pressure. The residue was mixed with isopropyl ether and n-hexane. The resulting precipitate was separated by decantation and dried under reduced pressure over sodium hydroxide.

The resulting product was dissolved in 50 ml of THF. Thereto were added 5.18 ml of triethylamine and 7.30 g of Boc-Ser(Bzl)-OSu with ice-cooling. The mixture was stirred for 5 hours at room temperature. The reaction mixture was mixed with 100 ml of ethyl acetate and 50 ml of water to effect extraction. The ethyl acetate layer was washed with 50 ml of water three times and then concentrated under reduced pressure. The residue was mixed with isopropyl ether and the resulting precipitate was collected by filtration and dried to obtain 8.20 g (yield: 80.6%) of the above objective compound. Melting point: 149°–151° C.

REFERENCE EXAMPLE 5

Preparation of Boc-Gly-Ser(Bzl)-Asn-Leu-OEt 3.00 grams of Boc-Ser(Bzl)-Asn-Leu-OEt was dissolved in 10 ml of TFA with ice-cooling. The mixture was stirred for 30 minutes at room temperature. The reaction mixture was concentrated under reduced pressure. The residue was mixed with isopropyl ether, and the resulting precipitate was collected by filtration and dried under reduced pressure over sodium hydroxide.

The resulting product was dissolved in 50 ml of THF and then neutralized with triethylamine with ice-cooling. Thereto was added 1.50 g of Boc-Gly-OSu. The mixture was stirred overnight at room temperature. The reaction mixture was concentrated under reduced pressure. The residue was dissolved in 50 ml of ethyl acetate. The solution was washed with 20 ml of 1 N hydrochloric acid twice and with 20 ml of a saturated aqueous sodium chloride solution twice, dried with anhydrous magnesium sulfate and concentrated under reduced pressure. The residue was washed with isopropyl ether to obtain 2.90 g (yield: 87.7%) of the above objective compound. Melting point: 165°–167° C.

REFERENCE EXAMPLE 6

Preparation of Boc-Gly-Ser(Bzl)-Asn-Leu-NHNH$_2$ 2.80 Grams of Boc-Gly-Ser(Bzl)-Asn-Leu-OEt was dissolved in 30 ml of methanol. Thereto was added 2.25 ml of NH$_2$NH$_2$.H$_2$O. The mixture was allowed to stand for 2 days at room temperature. The resulting precipitate was collected by filtration and washed with methanol to obtain 2.16 g (yield: 79.0%) of the above objective compound. Melting point: 221°–224° C.

REFERENCE EXAMPLE 7

Preparation of Boc-Gly-Ser(Bzl)-Asn-Leu-Ser(Bzl)-Thr(Bzl)-Glu-OBzl 0.86 Gram of Boc-Ser(Bzl)-Thr(Bzl)-Glu-OBzl.H$_2$O was dissolved in 5 ml of TFA with ice-cooling. The solution was stirred for 30 minutes at room temperature. The reaction mixture was concentrated under reduced pressure. The residue was dried under reduced pressure over sodium hydroxide.

To a solution of 0.78 g of Boc-Gly-Ser(Bzl)-Asn-Leu-N$_3$H$_3$ dissolved in 10 ml of DMF were added, with stirring at −15° C., 0.73 ml of 4N hydrochloric acid/dioxane and 0.18 ml of isoamyl nitrite in this order to form an azide. Then, triethylamine was added to effect neutralization.

The above product obtained by TFA treatment was dissolved in 10 ml of DMF and neutralized with triethylamine with ice-cooling. Thereto was added the above azide compound, and the mixture was allowed to stand overnight at 4° C. The reaction mixture was concentrated under reduced pressure. The residue was mixed with water to solidify. The resulting precipitate was collected by filtration and recrystallized from methanol to obtain 1.10 g (yield: 79.4%) of the above objective compound. Melting point: 194°–196° C.

REFERENCE EXAMPLE 8

Preparation of ⌐Gly—Ser(Bzl)—Asn—Leu—Ser(Bzl)—
Thr(Bzl)—Glu—OBzl.½H$_2$O 1.00 Gram of Boc-Gly-Ser(Bzl)-Asn-Leu-Ser(Bzl)-Thr(Bzl)-Glu-OBzl was dissolved in 10 ml of dry pyridine. Thereto was added 1.00 g of TFA-ONp and the mixture was allowed to stand for 8 hours at 40° C. The reaction mixture was concentrated under reduced pressure. The residue was solidified with isopropyl ether. The resulting precipitate was collected by filtration, washed with isopropyl ether and dried. The product was dissolved in 8 ml of TFA with ice-cooling. The solution was stirred for 30 minutes at room temperature. The reaction mixture was concentrated under reduced pressure, and the residue was dried under reduced pressure over sodium hydroxide.

The above TFA-treated product was dissolved in 15 ml of DMF. The solution was dropped into 700 ml of dry pyridine in 30 minutes with stirring at room temperature. The mixture was stirred for 5 hours at 50° C. The reaction mixture was concentrated under reduced pressure. The residue was mixed with 50 ml of ethyl acetate. The mixture was washed with 30 ml of 1N hydrochloric acid three times and 30 ml of a saturated aqueous sodium chloride solution three times, dried with anhydrous magnesium sulfate and concentrated under reduced pressure to remove ethyl acetate. The residue was mixed with methanol-ethyl acetate, and the insolubles were removed by filtration and the filtrate was concentrated. The residue was mixed with isopropyl ether, and the resulting precipitate was collected by filtration and washed with isopropyl ether and a small amount of ethyl acetate to obtain 0.46 g (yield: 50.7%) of the above objective compound. Melting point: 203°–207° C.

REFERENCE EXAMPLE 9

Preparation of ⌐Gly—Ser(Bzl)—Asn—Leu—Ser(Bzl)—
Thr(Bzl)—Glu—NHNH$_2$ 3.30 Grams of ⌐Gly—Ser(Bzl)—Asn—Leu—Ser(Bzl)—
Thr(Bzl)—Glu—OBzl.½H$_2$O was dissolved in 100 ml of methanol. Thereto was added 2.00 ml NH$_2$NH$_2$.H$_2$O. The mixture was allowed to stand for 2 days at room temperature. The reaction mixture was concentrated under reduced pressure. The residue was washed with isopropyl ether and the insolubles were collected by filtration. The insolubles were then suspended in a methanol-ethyl acetate mixture. The suspension was concentrated under reduced pressure. The resulting insolubles were filtered and dried to obtain 1.98 g (yield: 65.2%) of the above objective compound. Melting point: 230°–233° C.

REFERENCE EXAMPLE 10

Preparation of Boc-Leu-Gly-OEt 9.10 Milliliters of WSC was gradually added to 100 ml of a solution of 12.47 g of Boc-Leu-OH.H$_2$O, 6.98 g of HCl.H-Gly-OEt and 6.76 g of HOBT dissolved in dichloromethane, with ice-cooling. The mixture was stirred for 42 hours at room temperature. The reaction mixture was mixed with 100 ml of 1N hydrochloric acid, and the resulting precipitate was removed by filtration. The filtrate was washed with 100 ml of 1N hydrochloric acid, two 100-ml portions of a saturated aqueous sodium bicarbonate solution and 100 ml of a saturated aqueous sodium chloride solution in this order, dried with anhydrous magnesium sulfate and concentrated under reduced pressure. To the residue was added petroleum ether to crystallize the residue. The resulting crystal was recrystallized from ethyl acetate-petroleum ether to obtain 8.68 g (yield: 56.6%) of the above objective compound. Melting point: 79.5°–82.5° C.

REFERENCE EXAMPLE 11

Preparation of Boc-Val-Leu-Gly-OEt 7.66 Grams of Boc-Leu-Gly-OEt was dissolved in 30 ml of TFA with ice-cooling. The solution was stirred for 30 minutes at room temperature. The reaction mixture was concentrated under reduced pressure. The residue was washed with petroleum ether and dried under reduced pressure over sodium hydroxide. The resulting product was dissolved in 60 ml of DMF and adjusted to a pH 6 with triethylamine with ice-cooling. Thereto were added 5.43 g of Boc-Val-OH, 3.38 g of HOBT and 4.79 ml of WSC, and the mixture was stirred for 20 hours at room temperature. 200 ml of water was added to the reaction mixture. The resulting mixture was extracted with two 70-ml portions of ethyl acetate. The two organic layers were combined, washed with 1N hydrochloric acid, a saturated aqueous sodium bicarbonate solution and a saturated aqueous sodium chloride solution each two times and then dried with anhydrous magnesium sulfate. The resulting solution was concentrated under reduced pressure to remove ethyl acetate. The residue was mixed with petroleum ether to crystallize the residue. The crystal obtained was recrystallized from diethyl ether-petroleum ether twice to obtain 8.03 g (yield: 79.2%) of the above objective compound. Melting point: 69°–73.5° C.

REFERENCE EXAMPLE 12

Preparation of Boc-Val-Leu-Gly-OH 7.3 Grams of Boc-Val-Leu-Gly-OEt was dissolved in 50 ml of ethanol. Thereto was added 20 ml of 1N aqueous sodium hydroxide solution with ice-cooling, and the mixture was stirred for 1 hour. The reaction mixture was adjusted to pH 7 with 1N hydrochloric acid and concentrated under reduced pressure. The residue was washed with diethyl ether. The aqueous layer was adjusted to pH 2 with 1N hydrochloric acid with ice-cooling and extracted with three 60-ml portions of ethyl acetate. The organic layers were combined, washed with a saturated aqueous sodium chloride solution and dried with anhydrous magnesium sulfate. The resulting solution was concentrated under reduced pressure to remove ethyl acetate. The residue was mixed with petroleum ether to crystallize the residue, whereby 5.33 g (yield: 78.4%) of the objective compound was obtained.
Melting point: 99°–118° C.
Amino acid analysis:
Val: 0.95 (1)
Leu: 0.95 (1)
Gly: 1.10 (1)

REFERENCE EXAMPLE 13

Preparation of Gly—Ser(Bzl)—Asn—Leu—Ser(Bzl)—Thr(Bzl)—Glu—Val—Leu—Gly—OH 2.20 grams of Boc-Val-Leu-Gly-OH was dissolved in 10 ml of TFA with ice-cooling. The solution was stirred for 30 minutes at room temperature. The reaction mixture was concentrated under reduced pressure. The residue was dried under reduced pressure over sodium hydroxide.

1.00 Milliliter of 4N hydrochloric acid/dioxane and 0.40 ml of isoamyl nitrite were added in this order to a solution of 1.90 g of

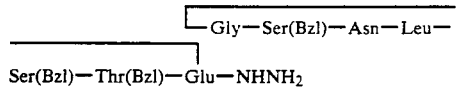

dissolved in 20 ml of DMF, with stirring at −15° C., to form an azide. Then, triethylamine was added to effect neutralization.

The above TFA-treated product was dissolved in 40 ml of DMF and then neutralized with triethylamine with ice-cooling. Thereto was added the above azide compound. The mixture was stirred overnight with ice-cooling. The reaction mixture was concentrated under reduced pressure. The residue was mixed with 0.5N hydrochloric acid. The resulting precipitate was collected by filtration and washed with water and hot methanol in this order to obtain 1.78 g (yield: 74.2%) of the above objective compound. Melting point: 244°–250° C.

REFERENCE EXAMPLE 14

Preparation of Boc-Ser(Bzl)-Gly-OH

To an aqueous solution containing 6.80 g of H-Gly-OH and 9.20 g of sodium hydrogen carbonate, under ice-cooling condition, was added 120 ml of THF solution containing 27.5 g of Boc-Ser(Bzl)-OSu, and the mixture was stirred at room temperature overnight.

The reaction mixture was subjected to concentration under reduced pressure, the residue thus obtained was washed with diethyl ether (50 ml, twice), then under ice-cooling condition the aqueous layer was adjusted to pH 2 by adding 1N-hydrochloric acid, and extracted with ethyl acetate (150 ml, three times), the organic layer was washed with 100 ml of saturated sodium chloride aqueous solution. The ethyl acetate layers were combined and dried over anhydrous magnesium sulfate, then concentrated under reduced pressure, the resulting oily residue was dried to yield 25.10 g (yield: 101.7%) of the above objective product as an oily substance.

REFERENCE EXAMPLE 15

Preparation of Boc-Ser(Bzl)-Gly-Thr(Bzl)-Pro-NH$_2$ 25.5 Grams of Boc-Thr(Bzl)-Pro-NH$_2$ [cf. Japanese Patent Kokai (Laid-open) No. 61-112099 (1986)] was dissolved by adding 50 ml of THF under ice-cooling condition, and the resulting solution was stirred at room temperature for 30 minutes. The reaction mixture was concentrated under reduced pressure, to the residue thus obtained was added diethyl ether, and the precipitate thus formed was collected by filtration and dried under reduced pressure over sodium hydroxide.

The above-mentioned formed product was dissolved in 150 ml of THF, and neutralized with triethylamine under ice-cooling condition, then 25.00 g of Boc-Ser(Bzl)-Gly-OH, 9.60 g of HOBT and 14.20 ml of WSC were added thereto and adjusted to pH 7, the whole mixture was stirred under ice-cooling condition for 2 hours, then at room temperature overnight.

The reaction mixture was concentrated under reduced pressure, the residue thus obtained was extracted with 500 ml of ethyl acetate. The ethyl acetate layer was washed with 1N-hydrochloric acid (200 ml×2 times), saturated sodium hydrogen carbonate aqueous solution (150 ml×5 times) and saturated sodium chloride aqueous solution (200 ml), respectively, then dried over anhydrous magnesium sulfate. Ethyl acetate was removed by evaporation under reduced pressure, then the residue obtained was solidified by adding diethyl ether-n-hexane to yield 30.60 g (yield: 75.9%) of the objective product. Melting point 56°–65° C.

Amino acid analysis:
Thr: 1.01 (1)
Ser: 0.96 (1)
Gly: 1.02 (1)
Pro: 1.01 (1)

REFERENCE EXAMPLE 16

Preparation of Boc-Thr(Bzl)-Gly-OH

By using 5.40 g of H-Gly-OH and 22.40 g of Boc-Thr(Bzl)-OSu, and the same procedure as in Reference Example 14 was repeated to obtain 19.60 g (yield: 97.3%) of the above-mentioned objective product.
Melting point: 63°–66° C.

REFERENCE EXAMPLE 17

Preparation of Boc-Thr(Bzl)-Gly-Ser(Bzl)-Gly-Thr(Bzl)-Pro-NH$_2$

By using 30.00 g of Boc-Ser(Bzl)-Gly-Thr(Bzl)-Pro-NH$_2$ and 19.60 g of Boc-Thr(Bzl)-Gly-OH, and the same procedure as in Reference Example 15 was repeated to obtain 32.36 g (yield: 77.7%) of the above-mentioned objective product.
Melting point: 83°–88° C.

REFERENCE EXAMPLE 18

Preparation of Boc-Asn-Thr(Bzl)-Gly-Ser(Bzl)-Gly-Thr(Bzl)-Pro-NH$_2$ 27.00 Grams of Boc-Thr(Bzl)-Gly-Ser(Bzl)-Gly-Thr(Bzl)-Pro-NH$_2$ was dissolved by adding 70 ml of TFA under ice-cooling condition, and the resulting solution was stirred at room temperature for 30 minutes. The reaction mixture was concentrated under reduced pressure, the residue thus obtained was added diethyl ether, and the precipitate thus formed was collected by filtration and dried under reduced pressure over sodium hydroxide.

The above-mentioned formed product was dissolved in 200 ml of THF, and neutralized with triethylamine under ice-cooling condition, then 10.74 g of Boc-Asn-ONp and 4.10 g of HOBT were added thereto and by keeping the pH 7–8, the mixture was stirred under ice-cooling condition for 1 hour, next at room temperature overnight, further 30 ml of DMF was added thereto and stirred overnight.

The reaction mixture was concentrated under reduced pressure, to the residue thus obtained was added 300 ml of cold water, and the mixture was subjected to decantation, next 300 ml of water was added thereto and the precipitate formed was collected by filtration and dried. The thus obtained crude product was re-precipitated from methanoldiethyl ether in three times to obtain 22.26 g (yield: 73.1%) of the objective product. Melting point: 161°–168° C.

Amino acid analysis:
Asp: 1.00 (1)
Thr: 1.94 (2)
Ser: 0.96 (1)
Gly: 2.06 (2)
Pro: 1.04 (1)

REFERENCE EXAMPLE 19

Preparation of Boc-Thr(Bzl)-Asn-Thr(Bzl)-Gly-Ser(Bzl)-Gly-Thr(Bzl)-Pro-NH$_2$

By using 21.00 g of Boc-Asn-Thr(Bzl)-Gly-Ser(Bzl)-Gly-Thr(Bzl)-Pro-NH$_2$ and 9.37 g of Boc-Thr(Bzl)-OSu, and the same procedure as in Reference Example 18 was repeated to obtain 23.4 g (yield: 93.6%) of the above-mentioned objective product. Melting point: 110–113° C.

REFERENCE EXAMPLE 20

Preparation of Boc-Arg(Tos)-Thr(Bzl)-Asn-Thr(Bzl)-Gly-Ser(Bzl)-Gly-Thr(Bzl)-Pro-NH$_2$ By using 8.35 g of Boc-Thr(Bzl)-Asn-Thr(Bzl)-Gly-Ser(Bzl)-Gly-Thr(Bzl)-Pro-NH$_2$ and 3.30 g of Boc-Arg(Tos)-OH, and the same procedure as in Reference 15 was repeated to obtain 7.60 g (yield: 70.5%) of the above-mentioned objective product. Melting point: 120°–132° C.

Aminoacid analysis:
Asp: 1.04 (1)
Thr: 3.00 (3)
Ser: 0.97 (1)
Gly: 2.00 (2)
Arg: 0.97 (1)
Pro: 1.03 (1)

REFERENCE EXAMPLE 21

Preparation of Boc-Tyr(Cl$_2$-Bzl)-Pro-OBzl

By using 5.00 g of Boc-Tyr(Cl$_2$Bzl)-OH and 2.89 g of H-Pro-OBzl.HCl, and the same procedure as in Reference Example 15 was repeated to obtain 6.84 g (yield: 95.6%) of the above-mentioned objective product.
Appearance: Oily substance.

REFERENCE EXAMPLE 22

Preparation of Boc-Thr(Bzl)-Tyr(Cl$_2$-Bzl)-Pro-OBzl

By using 6.84 g of Boc-Tyr(Cl$_2$-Bzl)-Pro-OBzl and 4.43 g of Boc-Thr(Bzl)-OSu, and the same procedure as in Reference Example 18 was repeated to obtain 5.54 g (yield: 62.1%) of the above-mentioned objective product.
Melting point: 119°–121° C.

REFERENCE EXAMPLE 23

Preparation of Boc-Thr(Bzl)-Tyr-(Cl$_2$-Bzl)-Pro-OH

By using 5.34 g of Boc-Thr(Bzl)-Tyr(Cl$_2$-Bzl)-Pro-OBzl, and the same procedure as in Reference Example 12 was repeated to obtain 2.03 g (yield: 42.7%) of the above-mentioned objective product. Melting point: 72°–85° C.

Amino acid analysis:
Thr: 0.93 (1)
Tyr: 1.02 (1)
Pro: 1.05 (1)

REFERENCE EXAMPLE 24

Preparation of
Boc-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 3.00 g of Boc-Arg(Tos)-Thr(Bzl)-Asn-Thr(Bzl)-Gly-Ser(Bzl)-Gly-Thr(Bzl)-Pro-NH$_2$ and 1.89 g of Boc-Thr(Bzl)-Tyr(Cl$_2$-Bzl)-Pro-OH, and the same procedure as in Reference Example 15 was repeated to obtain 3.30 g (yield: 78.2%) of the above-mentioned objective product.

Melting point: 166°–167° C.

REFERENCE EXAMPLE 25

Preparation of
Boc-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 3.20 g of Boc-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ and 666 mg of Boc-Gln-ONp, and the same procedure as in Reference Example 18 was repeated to obtain 3.25 g (yield: 95.8%) of the above-mentioned objective product.

Melting point: 148°–151° C.

REFERENCE EXAMPLE 26

Preparation of
Boc-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 1.00 g of Boc-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ and 305 mg of Boc-Lys(Cl-Z)-Leu-OH cf. Japanese Patent Kokai (Laid-open) No. 61-112099 (1986) and the same procedure as in Reference Example 15 was repeated to obtain 1.06 g (yield: 89.6%) of the above-mentioned objective product.

Melting point: 140°–143° C.

REFERENCE EXAMPLE 27

Preparation of
Boc-His(Tos)-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 900 mg of Boc-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$, 180 mg of Boc-His(Tos)-OH and 79 mg of HONB in place of HOBT, and the same procedure as in Reference Example 15 was repeated to obtain 950 mg (yield: 95.1%) of the above-mentioned objective product.

Melting point: 133°–137° C.

REFERENCE EXAMPLE 28

Preparation of Boc-Glu(OcHex)-Leu-OBzl

By using 13.2 g of Boc-Glu(OcHex)-OH and 15.7 g of H-Leu-OBzl Tos-OH, and the same procedure as in Reference Example 15 was repeated to obtain 23.19 g (yield: 108.8%) of the above-mentioned objective product.

Appearance: Oily substance.

REFERENCE EXAMPLE 29

Preparation of Boc-Gln-Glu(OcHex)-Leu-OBzl

By using 23.19 g of Boc-Glu(OcHex)-Leu-OBzl and 14.7 g of Boc-Gln-ONp, and the same procedure as in Reference Example 18 was repeated to obtain 22.42 g (yield: 84.8% calculated from Reference Example 28).

Melting point: 128°–131° C.

REFERENCE EXAMPLE 30

Preparation of Boc-Gln-Glu(OcHex)-Leu-OH 21.0 Grams of Boc-Gln-Glu(OcHex)-Leu-OBzl was dissolved in 200 ml of THF, and the solution was subjected to catalytic reduction in the presence of 2.00 g of 5%-palladium-carbon as the catalyst. After the reduction was finished, the catalyst was removed by filtration, and the filtrate was concentrated under reduced pressure. To the residue thus obtained was added diethyl ether-n-hexane to crystallize to obtaine 17.86 g (yield: 98.5%) of the above-mentioned objective product.

Melting point: 111°–114° C.

REFERENCE EXAMPLE 31

Preparation of Boc-Ser(Bzl)-Gln-Glu(OcHex)-Leu-OH 12.00 Grams of Boc-Gln-Glu(OcHex)-Leu-OH was dissolved in 30 ml of TFA under ice-cooling condition, and the solution was stirred at room temperature for 30 minutes. The reaction mixture was concentrated under reduced pressure, the residue thus obtained was treated by adding diethyl ether and isopropyl ether, and the precipitate formed was collected by filtration and dried over sodium hydroxide under reduced pressure.

This product was dissolved in THF-DMF (200 ml-30 ml) and neutralized with triethylamine under ice-cooling condition. Then 10.2 g of Boc-Ser(Bzl)-OSu was added thereto, and was adjusted to pH 7–8, and the mixture was stirred overnight. The reaction mixture was concentrated under reduced pressure, and the pH was adjusted to pH 2 by adding 1N-hydrochloric acid, then extracted with ethyl acetate (100 ml×3 times), and the ethyl acetate layer was washed with a saturated sodium chloride aqueous solution (100 ml×3 times), then was dried over anhydrous magnesium sulfate and concentrated under reduced pressure. The residue thus obtained was crystallized by adding diethyl ether and recrystallized from ethyl acetate-diethyl ether in four times to obtain 6.97 g (yield: 44.3%) of the above-mentioned objective product.

Melting point: 149°–153° C.

REFERENCE EXAMPLE 32

Preparation of
Boc-Ser(Bzl)-Gln-Glu(OcHex)-Leu-His(Tos)-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 500 mg of Boc-His(Tos)-Lys-(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ and 162 mg of Boc-Ser(Bzl)-Gln-Glu(OcHex)-Leu-OH as well as 39 mg of HONB in place of HOBT, and the same procedue as in Reference Example 15 was repeated to obtain 543 mg (yield: 89.3%) of the above-mentioned objective product.

Melting point: 216°–221° C.

REFERENCE EXAMPLE 33

Preparation of
Boc-Lys(Cl-Z)-Leu-Ser(Bzl)-Gln-Glu(OcHex)-Leu-His(Tos)-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 500 mg of Boc-Ser(Bzl)-Gln-Glu(OcHex)-Leu-His(Tos)-Lys(Cl-Z)-Leu-Gln-Thr(Bzl)-Tyr(Cl2-Bzl)-Pro -Arg(Tos)-Thr(Bzl)-Asn-Thr(Bzl)-Gly-Ser(Bzl)-Gly-Thr(Bzl)-Pro-NH$_2$ and 96 mg of Boc-Lys(Cl-Z)-Leu-OH as well as 33 mg of HONB in place of HOBT, and the same procedure as in Reference Example 15 was repeated to obtain 489 mg (yield: 88.0%) of the above-mentioned objective product.

Melting point: 204°–213° C.

REFERENCE EXAMPLE 34

Preparation of
Boc-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 2.00 g of Boc-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl) -Pro-NH$_2$ and 594 mg of Boc-Lys(Cl-Z)-OSu, and the same procedure as in Reference Example 18 was repeated to obtain 2.20 g (yield: 97.1%) of the above-mentioned objective product.

Melting point: 125°–127° C.

REFERENCE EXAMPLE 35

Preparation of
Boc-His(Tos)-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 2.00 g of Boc-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl) -Gly-Thr(Bzl)-Pro-NH$_2$ and 419 mg of Boc-His(Tos)-OH as well as 183 mg of HONB in place of HOBT, and the same procedure as in Reference Example 15 was repeated to obtain 2.11 g (yield: 94.6%) of the above-mentioned objective product.

Melting point: 123°–128° C.

REFERENCE EXAMPLE 36

Preparation of
Boc-Ser(Bzl)-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ By using 700 mg of Boc-His(Tos)-Lys(Cl-Z)-Gln-Thr(Bzl)-Tyr(Cl$_2$-Bzl)-Pro-Arg(Tos)-Thr(Bzl)-Asn-Thr(Bzl) -Gly-Ser(Bzl)-Gly-Thr(Bzl)-Pro-NH$_2$ and 235 mg of Boc-Ser(Bzl) -Gln-Glu(OcHex)-Leu-OH as well as 58 mg of HONB in place of HOBT, and the same procedure as in the Reference Example 15 was repeated to obtain 800 mg (yield: 93.5%) of the above-mentioned objective product.

Melting point: 210°–213° C.

REFERENCE EXAMPLE 37

Preparation of
Boc-Lys(Cl-Z)-Leu-Ser(Bzl)-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl)-GLy-Thr(Bzl)-Pro-NH$_2$ By using 700 mg of Boc-Ser(Bzl)-Gln-Glu(OcHex)-Leu-His(Tos)-Lys(Cl-Z)-Gln-Thr(Bzl)-Tyr(Cl$_2$-Bzl)-Pro -Arg(Tos)-Thr(Bzl)-Asn-Thr(Bzl)-Gly-Ser(Bzl)-Gly-Thr(Bzl)-Pro-NH$_2$ and 139 mg of Boc-Lys(Cl-Z)-Leu-OH, as well as 47 mg of HONB in place of HOBT, and the same procedure as in Reference Example 15 was repeated to obtain 701 mg (yield: 90.0%) of the above-mentioned objective product.

Melting point: 197°–204° C.

REFERENCE EXAMPLE 38

Preparation of Boc-Thr(Bzl)-Pro-OBzl

By using 8.66 g of Boc-Thr(Bzl)-OH and 7.42 g of HCl.H-Pro-OBzl, and the same procedure as in Reference Example 15 was repeated to obtain 13.25 g (yield: 95.3%) of the above mentioned objective product.

Appearance: Oily substance.

REFERENCE EXAMPLE 39

Preparation of Boc-Thr(Bzl)-Pro-OH

By using 13.25 g of Boc-Thr(Bzl)-Pro-OBzl, and the same procedure as in Reference Example 12 was repeated to obtain 9.72 g (yield: 89.6%) of the above-mentioned objective product.

Appearance: Powdery substance.

REFERENCE EXAMPLE 40

Preparation of
Boc-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 2.50 g of Boc-Arg(Tos)-Thr(Bzl)-Asn-Thr(Bzl)-Gly-Ser(Bzl)-Gly-Thr(Bzl)-Pro-NH$_2$ and 811 mg of Boc-Thr(Bzl)-Pro-OH, and the same procedure as in Reference Example 15 was repeated to obtain 2.42 g (yield: 81.4%) of the above-mentioned objective product.

Melting point: 164°–170° C.

REFERENCE EXAMPLE 41

Preparation of
Boc-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 2.30 g of Boc-Thr(Bzl)-Pro-Arg(Tos)-Thr(Bzl)-Asn-Thr(Bzl)-Gly-Ser(Bzl)-Gly-Thr(Bzl)-Pro-NH$_2$ and 564 mg of Boc-Gln-ONp, and the same procedure as in Reference Example 18 was repeated to obtain 2.14 g (yield: 87.1%) of the above-mentioned objective product.

Melting point: 128°–142° C.
Amino acid analysis:
  Asp: 1.04 (1)
  Thr: 3.93 (4)
  Ser: 0.94 (1)
  Glu: 1.00 (1)
  Gly: 2.14 (2)
  Arg: 1.00 (1)
  Pro: 1 97 (2)

REFERENCE EXAMPLE 42

Preparation of
Boc-Lys(Cl-Z)-Leu-Gln-Thr(Bzl)-Pro-Arg(Tos)-
Thr(Bzl)-Asn-Thr(Bzl)-Gly-Ser(Bzl)-Gly-Thr(Bzl)-
Pro-NH$_2$ By using 1.00 g of Boc-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ and 358 mg of Boc-Lys(Cl-Z)-Leu-OH, and the same procedure as in Reference Example 15 was repeated to obtain 1.17 g (yield: 96.4%) of the above-mentioned objective product.

Melting point: 114°–124° C.
Amino acid analysis:
 Asp: 1.04 (1)
 Thr: 3.95 (4)
 Ser: 0.97 (1)
 Glu: 1.02 (1)
 Gly: 2.07 (2)
 Leu: 1.09 (1)
 Lys: 1.07 (1)
 Arg: 0.96 (1)
 Pro: 1.99 (2)

REFERENCE EXAMPLE 43

Preparation of
Boc-His(Tos)-Lys(Cl-Z)-Leu-Gln-Thr(Bzl)-Pro-
Arg(Tos)-Thr(Bzl)-Asn-Thr(Bzl)-Gly-Ser(Bzl)
-Gly-Thr(Bzl)-Pro-NH$_2$ By using 1.00 g of Boc-Lys(Cl-Z)-Leu-Gln-Thr(Bzl)-Pro-Arg(Tos)-Thr(Bzl)-Asn-Thr(Bzl)-Gly-Ser(Bzl)-Gly -Thr(Bzl)-Pro-NH$_2$ and 228 mg of Boc-His(Tos)-OH as well as 100 mg of HONB in place of HOBT, and the same procedure as in Reference Example 15 was repeated to obtain 1.03 g (yield: 91.4%) of the above-mentioned objective product.

Melting point: 125°–131° C.

REFERENCE EXAMPLE 44

Preparation of
Boc-Gln-Glu(OcHex)-Leu-His(Tos)-Lys(Cl-Z)-Leu-
Gln-Thr(Bzl)-Pro-Arg(Tos)-Thr(Bzl)-Asn
-Thr(Bzl)-Gly-Ser(Bzl)-Gly-Thr(Bzl)-Pro-NH$_2$ By using 850 mg of Boc-His(Tos)-Lys(Cl-Z)-Leu-Gln-Thr(Bzl)-Pro-Arg(Tos)-Thr(Bzl)-Asn-Thr(Bzl)-Gly -Ser(Bzl)-Gly-Thr(Bzl)-Pro-NH$_2$ and 234 mg of Boc-Gln-Glu(OcHex)-Leu-OH as well as 75 mg of HONB in place of HOBT and the same procedure as in Reference Example 15 was repeated to obtain 780 mg (yield: 78.3%) of the above-mentioned objective product.

Melting point: 140°–158° C.
Amino acid analysis:
 Asp: 1.03 (1)
 Thr: 3.98 (4)
 Ser: 0.96 (1)
 Glu: 3.00 (3)
 Gly: 2.01 (2)
 Leu: 2.02 (2)
 Lys: 1.01 (1)
 His: 1.03 (1)
 Arg: 0.98 (1)
 Pro: 1.94 (2)

REFERENCE EXAMPLE 45

Preparation of Boc-Lys(Cl-Z)-Leu-Ser(Bzl)-OH

By using 4,61 g of Boc-Leu-Ser(Bzl)-OH Japanese Patent Kokai (Laid-open) No. 61-112099 (1986) and 5.61 g of Boc-Lys(Cl-Z)-OSu, and the same procedure as in Reference Example 31 was repeated to obtain 4.92 g (yield: 64.0%) of the above-mentioned objective product.

Melting point: 88°–92° C.

REFERENCE EXAMPLE 46

Preparation of
Boc-Lys(Cl-Z)-Leu-Ser(Bzl)-Gln-Glu(OcHex)-Leu-
His(Tos)-Lys(Cl-Z)-Leu-Gln-Thr(Bzl)-Pro
-Arg(Tos)-Thr(Bzl)-Asn-Thr(Bzl)-Gly-Ser(Bzl)-Gly-
Thr(Bzl)-Pro-NH$_2$ By using 700 mg of Boc-Gln-Glu(OcHex)-Leu-His(-Tos)-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH$_2$ and 209 mg of Boc-Lys(Cl-Z)-Leu-Ser(Bzl)-OH as well as 78 mg of HONB in place of HOBT, and the same procedure as in Reference Example 15 was repeated to obtain 751 mg (yield: 90.0%) of the above-mentioned objective product.

Melting point: 171°–195° C. (decomposed)
Amino acid analysis:
 Asp: 1.03 (1)
 Thr: 3.95 (4)
 Ser: 1.75 (2)
 Glu: 3.03 (3)
 Gly: 2.01 (2)
 Leu: 2.99 (3)
 Lys: 2.06 (2)
 His: 1.00 (1)
 Arg: 0.96 (1)
 Pro: 1.98 (2)

REFERENCE EXAMPLE 47

Preparation of Boc-Asn-Lys(Cl-Z)-Leu-OH

By using 2.00 g of Boc-Lys(Cl-Z)-Leu-OH and 1.48 g of Boc-Asn-ONp, and the same procedure as in Reference Example 31 was repeated to obtain 1.76 g (yield: 72.3%) of the above-mentioned objective product.

Melting point: 160°–163° C.

REFERENCE EXAMPLE 48

Preparation of
Boc-Asn-Lys(Cl-Z)-Leu-Gln-Thr(Bzl)-Pro-Arg(Tos)-
Thr(Bzl)-Asn-Thr(Bzl)-Gly-Ser(Bzl)
-Gly-Thr(Bzl)-Pro-NH$_2$ By using 500 mg of Boc-Gln-Thr(Bzl)-Pro-Arg(Tos)-Thr(Bzl)-Asn-Thr(Bzl)-Gly-Ser(Bzl)-Gly-Thr(Bzl) -Pro-NH$_2$ and 200 mg of Boc-Asn-Lys(Cl-Z)-Leu-OH, and the same procedure as in Reference Example 15 was repeated to obtain 582 mg (yield: 91.6%) of the above-mentioned objective product.

Melting point: 117°–122° C.

REFERENCE EXAMPLE 49

Preparation of
Boc-Ser(Bzl)-Gln-Glu(OcHex)-Leu-Asn-Lys(Cl-Z)-
Leu-Gln-Thr(Bzl)-Pro-Arg(Tos)-Thr(Bzl)-Asn
-Thr(Bzl)-Gly-Ser(Bzl)-Gly-Thr(Bzl)-Pro-NH$_2$ By using 500 mg of Boc-Asn-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH$_2$ and 195 mg of Boc-Ser(Bzl)-Gln-Glu (OcHex)-Leu-OH, and the same procedure as in Reference Example 15 was repeated to obtain 561 mg (yield: 89.1%) of the above-mentioned objective product.

Melting point: 206°–227° C. (decomposed)
Amino acid analysis:
  Asp 2 00 (2)
  Thr: 3.90 (4)
  Ser: 1.90 (2)
  Glu: 3.16 (3)
  Gly: 1.97 (2)
  Leu: 2.07 (2)
  Lys: 0.98 (1)
  Arg: 0.91 (1)
  Pro: 1.92 (2)

REFERENCE EXAMPLE 50

Preparation of
Boc-Lys(Cl-Z)-Leu-Ser(Bzl)-Gln-Glu(OcHex)-Leu-
Asn-Lys(Cl-Z)-Leu-Gln-Thr(Bzl)-Pro-Arg(Tos)
-Thr(Bzl)-Asn-Thr(Bzl)-Gly-Ser(Bzl)-Gly-Thr(Bzl)-
Pro-NH$_2$ By using 520 mg of Boc-Ser(Bzl)-Gln-Glu(OcHex)-Leu-Asn-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH$_2$ and 117 mg of Boc-Lys(Cl-Z)-Leu-OH , and the same procedure as in Reference Example 15 was repeated to obtain 553 mg (yield: 93.5%) of the objective product.

Melting point: 198°–217° C.(decomposed)
Amino acid analysis:
  Asp: 1.95 (2)
  Thr: 3.72 (4)
  Ser: 1.85 (2)
  Glu: 3.11 (3)
  Gly: 1.93 (2)
  Leu: 3.11 (3)
  Lys: 1.99 (2)
  Arg: 0.91 (1)
  Pro: 1.85 (2)

REFERENCE EXAMPLE 51

Preparation of Boc-Thr(Bzl)-Asp-OEt

To a suspension consisting of 2.3 g of H-Asp-OEt, 5.8 g of Boc-Thr(Bzl)-OSu, 20 ml of THF and 20 ml of DMF was added 2 ml of triethylamine under ice-cooling condition, and the mixture was stirred for 1 hour, then the pH of the reaction mixture was controlling to about pH 7, and the reaction was continued for 36 hours at room temperature. The reaction mixture was concentrated under reduced pressure, and the thus obtained residue was acidified by adding 1N-hydrochloric acid, then was extracted with ethyl acetate (80 ml×3 times). The organic layer was washed with water, then with a saturated sodium chloride aqueous solution, and dried over anhydrous magnesium sulfate, then concentrated under reduced pressure. Crystallized and recrystallized from diethyl ether-petroleum ether to obtain 5.59 g (yield: 86.6%) of the above-mentioned objective product.

Melting point: 93°–95° C.

REFERENCE EXAMPLE 52

Preparation of Boc-Ser(Bzl)-Thr(Bzl)-Asp-OEt

To 4.52 g of Boc-Thr(Bzl)-Asp-OEt was added 20 ml of TFA to dissolve the formed, under an ice-cooling condition. then the solution was stirred at room temperature for 30 minutes. The reaction mixture was concentrated under reduced pressure, and the thus obtained residue was dried over sodium hydroxide under reduced pressure. The thus obtained product was dissolved in 20 ml of THF, and the pH of said solution was adjusted to pH 7 by adding triethylamine, under an ice-cooling condition. The, 3.29 g of Boc-Ser(Bzl)-OSu was added thereto and the mixture was stirred for 20 hours. After the reaction mixture was concentrated under reduced pressure, the thus obtained residue residue was dissolved by adding 150 ml of ethyl acetate, then said solution was washed with 1N-hydrochloric acid (50 ml×2 times), a saturated sodium hydrogen carbonate aqueous solution (50 ml×2 times), and a saturated sodium chloride aqueous solution (50 ml×2 times), respectively, dried over anhydrous magnesium sulfate, then ethyl acetate was removed by evaporation under reduced pressure. To the residue thus obtained was crystallized by adding diethyl ether and petroleum ether, and recrystallized from ethyl acetate-petroleum ether to obtain 3.61 g (yield: 57.3%) of the above-mentioned objective product.

Melting point: 90°–92° C.

REFERENCE EXAMPLE 53

Preparation Boc-Acp-Asn-Leu-OEt

By using 4.00 g of Boc-Asn-Leu-OEt and 3.40 g of Boc-Acp-OSu, and the same procedure as in Example Reference Example 18 was repeated to obtain 4.98 g (yield: 95.5%) of the above-mentioned objective product.

Melting Point: 145°–146° C.

REFERENCE EXAMPLE 54

Preparation of Boc-Acp-Asn-Leu-NH-NH$_2$

By using 4.90 g of Boc-Acp-Asn-Leu-OEt, and the same procedure as in Reference Example 6 was repeated to obtain 4.26 g (yield: 86.2%) of the above-mentioned objective product.

Melting point: 200°–202° C.

REFERENCE EXAMPLE 55

Preparation of
Boc-Acp-Asn-Leu-Ser(Bzl)-Thr(Bzl)-Asp-OEt

By using 2.66 g of Boc-Ser(Bzl)-Thr(Bzl)-Asp-OEt and 2.20 g of Boc-Acp-Asn-Leu-NHNH$_2$, and the same procedure as in Reference Example 7 was repeated to obtain 3.22 g (yield: 78.5%) of the above-mentioned objective product.

Melting point: 200°–203° C.

REFERENCE EXAMPLE 56

Preparation of

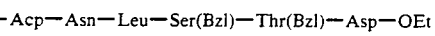
Acp—Asn—Leu—Ser(Bzl)—Thr(Bzl)—Asp—OEt

By using 3.00 g of Boc-Acp-Asn-Leu-Ser(Bzl)-Thr(Bzl)-Asp-OEt, and the same procedure as in Reference Example 8 was repeated to obtain 700 mg (yield: 26.6%) of the above-mentioned objected product.
Melting point: 228°–231° C.

REFERENCE EXAMPLE 57

Preparation of

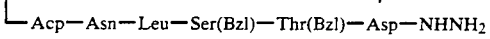
Acp—Asn—Leu—Ser(Bzl)—Thr(Bzl)—Asp—NHNH$_2$

By using 650 mg of Acp-Asn-Leu-Ser(Bzl)-Thr(Bzl)-Asp-OEt, and the same procedure as in Reference Example 9 was repeated to obtain 400 mg (yield: 62.6%) of the above-mentioned objective product.
Melting point: 212°–218° C.

REFERENCE EXAMPLE 58

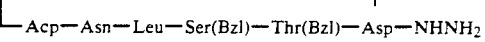
Preparation of Acp—Asn—Leu—Ser(Bzl)—Thr(Bzl)—Asp—Val—Leu—Gly—OH

By using 350 mg of

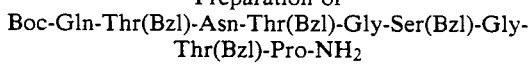
Acp—Asn—Leu—Ser(Bzl)—Thr(Bzl)—Asp—NHNH$_2$ and 324 mg of Boc-Val-Leu-Gly-OH, and the same procedure as in Reference Example 13 was repeated to obtain 320 mg (yield: 70.0%) of the above-mentioned objective product.
Melting point: 235°–240° C. (decomposed).

REFERENCE EXAMPLE 59

Preparation of
Boc-Gln-Thr(Bzl)-Asn-Thr(Bzl)-Gly-Ser(Bzl)-Gly-Thr(Bzl)-Pro-NH$_2$ By using 2.50 g of Boc-Thr(Bzl)-Asn-Thr(Bzl)-Gly-Ser(Bzl)-Gly-Thr(Bzl)-Pro-NH$_2$ and 921 mg of Boc-Gln-ONp, and the same procedure as in Reference Example 18 was repeated to obtain 2.59 g (yield: 94.1%) of the above-mentioned objective product.
Melting point: 200°–204° C.

REFERENCE EXAMPLE 60

Preparation of
Boc-Thr(Bzl)-Pro-Gln-Thr(Bzl)-Asn-Thr(Bzl)-Gly-Ser(Bzl)-Gly-Thr(Bzl)-Pro-NH$_2$ By using 2.48 g of Boc-Gln-Thr(Bzl)-Asn-Thr(Bzl)-Gly-Ser(Bzl)-Gly-Thr(Bzl)-Pro-NH$_2$ and 1.14 g of Boc-Thr(Bzl)- e Pro-OH, and the same procedure as in Reference Example 15 was repeated to obtain 2.72 g (yield: 90.4%) of the above-mentioned objective product.
Melting point: 185°–190° C.

REFERENCE EXAMPLE 61

Preparation of
Boc-Gln-Thr(Bzl)-Pro-Gln-Thr(Bzl)-Asn-Thr(Bzl)-Gly-Ser(Bzl)-Gly-Thr(Bzl)-Pro-NH$_2$ By using 2.65 g of Boc-Thr(Bzl)-Pro-Gln-Thr(Bzl)-Asn-Thr(Bzl)-Gly-Ser(Bzl)-Gly-Thr(Bzl)-Pro-NH$_2$ and 907 mg of Boc-Gln-ONp, and the same procedure as in Reference Example 18 was repeated to obtain 2.74 g (yield: 95.5%) of the above-mentioned objective product.
Melting point: 195°–200° C.

REFERENCE EXAMPLE 62

Preparation of
Boc-Lys(Cl-Z)-Leu-Gln-Thr(Bzl)-Pro-Gln-Thr(Bzl)-Asn-Thr(Bzl)-Gly-Ser(Bzl)-Gly-Thr(Bzl) -Pro-NH$_2$ By using 706 mg of Boc-Gln-Thr(Bzl)-Pro-Gln-Thr(Bzl)-Asn-Thr(Bzl)-Gly-Ser(Bzl)-Gly-Thr(Bzl)-Pro-NH$_2$ and 320 mg of Boc-Lys(Cl-Z)-Leu-OH, and the same procedure as in Reference Example 15 was repeated to obtain 730 mg (yield: 84.0%) of the above-mentioned objective product.
Melting point: 216°–220° C. (decomposed).

REFERENCE EXAMPLE 63

Preparation of
Boc-His(Tos)-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro-NH$_2$ By using 712 mg of Boc-Lys(Cl-Z)-Leu-Gln-Thr(Bzl)-Pro-Gln-Thr(Bzl)-Asn-Thr(Bzl)-Gly-Ser(Bzl)-Gly-Thr(Bzl) -Pro-NH$_2$ and 204 mg of Boc-His(Tos)-OH and 57 mg of HOSu in place of HOBT, and the same procedure as in Reference Example 15 was repeated to obtain 759 mg (yield: 94.0%) of the above-mentioned objective product.
Melting point: 200°–216° C. (decomposed).
Amino acid analysis:
  Asp: 1.02 (1)
  Thr: 3.87 (4)
  Ser: 0.92 (1)
  Glu: 2.06 (2)
  Gly: 2.04 (2)
  Leu: 1.01 (1)
  Lys: 0.99 (1)
  His: 1.05 (1)
  Pro: 2.05 (2)

REFERENCE EXAMPLE 64

Preparation of
Boc-Gln-Glu(OcHex)-Leu-His(Tos)-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro-NH$_2$ By using 715 mg of Boc-His(Tos)-Lys(Cl-Z)-Leu-Gln-Thr(Bzl)-Pro-Gln-Thr(Bzl)-Asn-Thr(Bzl)-Gly-Ser(Bzl) -Gly-Thr(Bzl)-Pro-NH$_2$ and 244 mg of Boc-Gln-Glu(OcHex) -Leu-OH and 51 mg of HOSu in place of HOBT , and the same procedure as in Reference Example 15 was repeated to obtain 720 mg (yield: 85.0%) of the above-mentioned objective product.
Melting point: 190°–205° C. (decomposed).
Amino acid analysis:
Asp: 1.03 (1)
Thr: 3.95 (4)
Ser: 0.94 (1)
Glu: 3.93 (4)
Gly: 2.05 (2)
Leu: 1.96 (2)
Lys: 1.01 (1)
His: 1.00 (1)
Pro: 2.06 (2)

REFERENCE EXAMPLE 65

Preparation of
Boc-Lys(Cl-Z)-Leu-Ser(Bzl)-Gln-Glu(OcHex)-Leu-His(Tos)-Lys(Cl-Z)-Leu-Gln-Thr(Bzl)-Pro
-Gln-Thr(Bzl)-Asn-Thr(Bzl)-Gly-Ser(Bzl)-Gly-Thr(Bzl)-Pro-NH$_2$ By using 684 mg of Boc-Gln-Glu(OcHex)-Leu-His(-Tos)-Lys(Cl-Z)-Leu-Gln-Thr(Bzl)-Pro-Gln-Thr(Bzl)-Asn -Thr(Bzl)-Gly-Ser(Bzl)-Gly-Thr(Bzl)-Pro-NH$_2$ and 251 mg of Boc-Lys(Cl-Z)-Leu-Ser(Bzl)-OH as well as 41 mg of HOSu in place of HOBT, and the same procedure as in Reference Example 15 was repeated to obtain 617 mg (yield: 74.9%) of the above-mentioned objective product.
Melting point: 220°–228° C. (decomposed).

REFERENCE EXAMPLE 66

Preparation of
Boc-Asn-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro-NH$_2$ By using 1.41 g of Boc-Gln-Thr(Bzl)-Pro-Gln-Thr(Bzl)-Asn-Thr(Bzl)-Gly-Ser(Bzl)-Gly-Thr(Bzl)-Pro-NH$_2$ and 781 mg of Boc-Asn-Lys(Cl-Z)-Leu-OH, and the same procedure as in Reference Example 15 was repeated to obtain 1.79 g (yield: 98.0%) of the above-mentioned objective product.
Melting point: 212°–220° C.

REFERENCE EXAMPLE 67

Preparation of
Boc-Gln-Glu(OcHex)-Leu-Asn-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro-NH$_2$ By using 1.81 g of Boc-Asn-Lys(Cl-Z)-Leu-Gln-Thr(Bzl)-Pro-Gln-Thr(Bzl)-Asn-Thr(Bzl)-Gly-Ser(Bzl)-Gly -Thr(Bzl)-Pro-NH$_2$ and 666 mg of Boc-Gln-Glu(OcHex)-Leu-OH, and the same procedure as in Reference Example 15 was repeated to obtain 1.96 g (yield: 90.5%) of the above-mentioned objective product.
Melting point: 219°–227° C.

REFERENCE EXAMPLE 68

Preparation of
Boc-Lys(Cl-Z)-Leu-Ser(Bzl)-Gln-Glu(OcHex)-Leu-Asn-Lys(Cl-Z)-Leu-Gln-Thr(Bzl)-Pro-Gln
-Thr(Bzl)-Asn-Thr(Bzl)-Gly-Ser(Bzl)-Gly-Thr(Bzl)-Pro-NH$_2$ By using 869 mg of Boc-Gln-Glu(OcHex)-Leu-Asn-Lys(Cl-Z)-Leu-Gln-Thr(Bzl)-Pro-Gln-Thr(Bzl)-Asn-Thr(Bzl) -Gly-Ser(Bzl)-Gly-Thr(Bzl)-Pro-NH$_2$ and 339 mg of Boc-Lys(Cl-Z)-Leu-Ser(Bzl)-OH, and the same procedure as in Reference Example 15 was repeated to obtain 967 mg (yield: 91.5%) of the above-mentioned objective product.
Melting point: 241°–245° C. (decomposed).

REFERENCE EXAMPLE 69

Preparation of
Boc-Gly-Lys(Cl-Z)-Leu-Gln-Thr(Bzl)-Pro-Arg(Tos)Thr(Bzl)-Asn-Thr(Bzl)-Gly-Ser(Bzl)-Gly
-Thr(Bzl)-Pro-NH$_2$ At first, by using 2.00 g of Boc-Lys(Cl-Z)-Leu-OH and 1.10 g of Boc-Gly-OSu, and the same procedure as in Reference Example 31 was repeated to obtain 1.69 g (yield: 76.0%) of Boc-Gly-Lys(Cl-Z)-Leu-OH.
Appearance: Powdery substance
Amino acid analysis:
Gly: 0.94 (1)
Leu: 1.04 (1)
Lys: 1.03 (1).
Then, 500 mg of Boc-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ and 198 mg of the above-mentioned Boc-Gly-Lys(Cl-Z)-Leu-OH were used, and the same procedure as in Reference Example 15 was repeated to obtain 575 mg (yield: 92.6%) of the above-mentioned objective product.
Melting point: 127°–131° C.

REFERENCE EXAMPLE 70

Preparation of
Boc-Ser(Bzl)-Gln-Glu(OcHex)-Leu-Gly-Lys(Cl-Z)-Leu-Gln-Thr(Bzl)-Pro-Arg(Tos)-Thr(Bzl)-Asn
-Thr(Bzl)-Gly-Ser(Bzl)-Gly-Thr(Bzl)-Pro-NH$_2$ By using 520 mg of Boc-Gly-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH$_2$ and 212 mg of Boc-Ser(Bzl)-Gln-Glu(OcHex)-Leu-OH, and the same procedure as in Reference Example 15 was repeated to obtain 652 mg (yield: 99.0%) of the above-mentioned objective product.
Melting point: 183°–217° C. (decomposed).
Amino acid analysis:
Asp: 1.01 (1)
Thr: 3.86 (4)
Ser: 1.87 (2)
Glu: 3.07 (3)
Gly: 3.05 (3)
Leu: 2.04 (2)
Lys: 1.00 (1)
Arg: 0.92 (1)
Pro: 1.96 (2)

REFERENCE EXAMPLE 71

Preparation of
Boc-Lys(Cl-Z)-Leu-Ser(Bzl)-Gln-Glu(OcHex)-Leu-Gly-Lys(Cl-Z)-Leu-Gln-Thr(Bzl)-Pro-Arg(Tos)
-Thr(Bzl)-Asn-Thr(Bzl)-Gly-Ser(Bzl)-Gly-Thr(Bzl)-Pro-NH$_2$ By using 620 mg of Boc-Ser(Bzl)-Gln-Glu(OcHex)-Leu-Gly-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH$_2$ and 141 mg of Boc-Lys(Cl-Z)-Leu-OH, and the same procedure as in Reference Example 15 was repeated to obtain 680 mg (yield: 96.3%) of the above-mentioned objective product.

Melting point: 198°-208° C.
Amino acid analysis:
  Asp: 1.00 (1)
  Thr: 3.83 (4)
  Ser: 1.85 (2)
  Glu: 3.11 (3)
  Gly: 3.08 (3)
  Leu: 3.07 (3)
  Lys: 1.99 (2)
  Arg: 0.91 (1)
  Pro: 1.91 (2)

REFERENCE EXAMPLE 72

Preparation of Boc-Thr(Bzl)-Asp-OEt

To a suspension consisting of 2.3 g of H-Asp-OEt, 5.8 g of Boc-Thr(Bzl)-OSu in 20 ml of THF and 20 ml of DMF, was added 2 ml of triethylamine under an ice-cooling condition and the mixture was stirred for 1 hour so as to the pH of the reaction mixture was adjusting to about pH 7, and the reaction was continued for 36 hours. The reaction mixture was concentrated under reduced pressure and the residue thus obtained was acidified by adding 1N-hydrochloric acid, and extracted with ethyl acetate (80 ml×3 times). The organic layer was washed with water, then with a saturated sodium chloride aqueous solution and dried over anhydrous magnesium sulfate, The ethyl acetate extract was concentrated under reduced pressure and the residue thus obtained was crystallized and recrystallized from diethyl ether-petroleum ether. 5.59 Grams (yield: 86.6%) of the above-mentioned objective product was obtained.

Melting point: 93°-95° C.

REFERENCE EXAMPLE 73

Preparation of Boc-Ser(Bzl)-Thr(Bzl)-Asp-OEt

Under ice-cooling condition, 4.52 g of Boc-Thr(Bzl)-Asp-OEt was dissolved by adding 20 ml of TFA, and stirred at room temperature for 30 minutes. The reaction mixture was concentrated under reduced pressure, and the residue thus obtained was dried over sodium hydroxide under reduced pressure. The above-mentioned product was dissolved in 20 ml of THF, and the pH thereof was adjusted with triethylamine under ice-cooling. Then 3.29 g of Boc-Ser(Bzl)-OSu was added thereto and stirred for 20 hours. The reaction mixture was concentrated under reduced pressure, and the residue thus obtained was dissolved by adding 150 ml of ethyl acetate, then this solution was washed with 1N-hydrochloric acid (50 ml×2 times), a saturated sodium hydrogen carbonate solution (50 ml×2 times), and a saturated sodium chloride aqueous solution (50 ml×2 times) respectively, dried over anhydrous magnesium sulfate. The ethyl acetate extract was concentrated under reduced pressure and the residue thus obtained was crystallized by adding diethyl ether and petroleum ether, then recrystallized from ethyl acetate-petroleum ether. 3.61 Grams (yield: 57.3%) of the above-mentioned objective product was obtained.

Melting point: 90°-92° C.

REFERENCE EXAMPLE 74

Preparation of Boc-$\beta$-Ala-Ser(Bzl)-Asn-Leu-OEt

Under ice-cooling condition, 4.41 g of Boc-Ser(Bzl)-Asn-Leu-OEt was dissolved by adding 20 ml of TFA, and stirred at room temperature for 30 minutes. The reaction mixture was concentrated under reduced pressure, and to the residue thus obtained was added diethyl ether, and product being precipitated was collected by filtration, then dried over sodium hydroxide under reduced pressure. The above-mentioned product was dissolved in a mixture of 100 ml of THF and 20 ml of DMF, then under ice-cooling condition, the pH of the mixture was adjusted of about pH 7 by adding triethylamine. Then 2.75 g of Boc-$\beta$-Ala-OSu was added thereto and the whole mixture was stirred at room temperature overnight. The reaction mixture was concentrated under reduced pressure, to thus obtained residue was added 200 ml of water, the precipitate formed was collected by filtration, and recrystallized twice from ethanol. By the above-mentioned procedure, 3.41 g (yield: 68.6%) of the above-mentioned objective product was obtained.

Melting point: 190°-192° C.

REFERENCE EXAMPLE 75

Preparation of Boc-$\beta$-Ala-Ser(Bzl)-Asn-Leu-NHNH$_2$

3 Grams of Boc-$\beta$-Ala-Ser(Bzl)-Asn-Leu-OEt was dissolved in 20 ml of methanol, then to this solution was added 2.4 ml of NH$_2$NH$_2$.H$_2$O and the mixture was stirred overnight, further 20 ml of DMF was added to the reaction mixture and the precipitate formed was dissolved, and was stirred overnight. The reaction mixture was concentrated under reduced pressure, to the residue thus obtained was added 15 ml of water, and the precipitate formed was collected by filtration and recrystallized twice from ethanol. 1.72 Grams (yield: 58.7%) of the above-mentioned objective product was obtained.

Melting point: 241°-245° C.

REFERENCE EXAMPLE 76

Preparation of
Boc-$\beta$-Ala-Ser(Bzl)-Asn-Leu-Ser(Bzl)-Thr(Bzl)-Asp-OEt

Under ice-cooling condition, 6.6 g of Boc-Ser(Bzl)-Thr(Bzl)-Asp-OEt was dissolved by adding 30 ml of TFA, and the solution was stirred at room temperature for 30 minutes. The reaction mixture was concentrated under reduced pressure, and the residue obtained was treated adding petroleum ether and the precipitate formed was collected by filtration, then dried over sodium hydroxide under reduced pressure.

On the other hand, 7.0 g of Boc-$\beta$-Ala-Ser(Bzl)-Asn-Leu-NHNH$_2$ was dissolved in 30 ml of DMF, then under cooling at $-15°$ C. to $-20°$ C. with stirring condition, 7.2 ml of 4N-hydrochloric acid/dioxane, next 2 ml of isoamyl nitrite were added thereto to form azide compound thereof, and was neutralized by adding triethylamine.

The above-mentioned product being treated with TFA was dissolved in 20 ml of DMF and was neutralized with 20 ml of DMF under ice-cooling condition. Then the above-mentioned azide compound thereof was added thereto, and by keeping the pH of this mixture was keeping at pH 7 to 8, the mixture was stirred at 4° C. for 20 hours. The reaction mixture was concentrated under reduced pressure, to the residue thus obtained was added 30 ml of 0.5N-hydrochloric acid, and the precipitate formed was collected by filtration, recrystallized twice from methanol. 10.46 Grams (yield: 90.4%) of the above-mentioned objective product was obtained.

Melting point: 236°-245° C. (decomposed).

REFERENCE EXAMPLE 77

Preparation of ⌊β-Ala—Ser(Bzl)—Asn—Leu—Ser(Bzl)—
              ⌉
Thr(Bzl)—Asp—OEt 4.3 Grams of Boc-β-Ala-Ser(Bzl)-Asn-Leu-Ser(Bzl)-Thr(Bzl)-Asp-OEt was dissolved in 45 ml of dried pyridine, to this solution was added 3.66 g of TFA-ONp and the mixture was allowed to stand at 40° C. for 4 hours. The reaction mixture was concentrated under reduced pressure, to the residue obtained was added diethyl ether and the precipitate formed was collected by filtration, next the precipitate was dissolved by adding 50 ml of TFA under ice-cooling condition, further stirred at room temperature for 45 minutes. The reaction mixture was concentrated under reduced pressure, to the residue thus obtained was added ethyl acetate, and the crystals formed were collected by filtration and dried over sodium hydroxide.

The above-mentioned product being treated with TFA was dissolved in 50 ml of DMF, then to this solution was added dropwise 800 ml of dried pyridine being warmed at 50° C. by taking 6 hours, under stirring condition. After finished the dropwise addition, the reaction mixture was stirred at room temperature overnight, then concentrated under reduced pressure. To the residue thus obtained was added 100 ml of water and the precipitate thus formed was collected by filtration, dissolved in ethanol by heating, then the solution was allowed to stand to cool at room temperature, and the precipitate formed in the solution was removed by filtration. Ethyl acetate was added to the filtrate and the precipitate formed was collected by filtration. 1.9 Grams (yield: 49.5%) of the above-mentioned objective product was obtained.

Melting point: 230°-233° C.

REFERENCE EXAMPLE 78

Preparation of ⌊β-Ala—Ser(Bzl)—Asn—Leu—Ser(Bzl)—
              ⌉
Thr(Bzl)—Asp—NHNH$_2$.H$_2$O 1.89 Grams of ⌊β-Ala—Ser(Bzl)—Asn—Leu—Ser(Bzl)—
⌉
Thr(Bzl)—Asp—OEt was dissolved in a mixture of 50 ml of methanol and 15 ml of DMF, then to this solution was added 1.7 ml of NH$_2$NH$_2$.H$_2$O and the mixture was stirred at room temperature overnight. To this reaction mixture was added 200 ml of water, and the precipitate formed was collected by filtration. This precipitate was thoroughly dried and suspended in methanol-ethyl acetate, then concentrated under reduced pressure and precipitate formed was collected by filtration. 620 Milligrams (yield: 34.4%) was obtained.

Melting point: 235°-238° C.

REFERENCE EXAMPLE 79

Preparation of ⌊β-Ala—Ser(Bzl)—Asn—Leu—Ser(Bzl)—
              ⌉
Thr(Bzl)—Asp—Val—Leu—Gly—OH Under ice-cooling condition, 440 mg of Boc-Val-Leu-Gly-OH was dissolved by adding 5 ml of TFA, and the solution was stirred at room temperature for 30 minutes. The reaction mixture was concentrated under reduced pressure, and the residue thus obtained was treated by adding diethyl ether, the precipitate thus formed was collected by filtration and dried over sodium hydroxide under reduced pressure.

On the other hand, 550 mg of

⌊β-Ala—Ser(Bzl)—Asn—Leu—Ser(Bzl)—
⌉
Thr(Bzl)—Asp—NHNH$_2$.H$_2$O was dissolved in 20 ml o of DMF, then under cooling at −15° C. to −20° C. with stirring condition, 0.43 ml of 4N-hydrochloric acid/dioxane, next 0.11 ml of isoamyl nitrite were added thereto to form azide compound thereof, and was neutralized by adding triethylamine.

The above-mentioned product being treated with TFA was dissolved in 10 ml of DMF and was neutralized with triethylamine under ice-cooling condition. Then the above-mentioned azide compound thereof was added thereto, and by keeping the pH of this mixture was keeping at pH 7 to 8, the mixture was stirred at 4° C. for 4 hours. The reaction mixture was concentrated under reduced pressure, to the residue thus obtained was added 30 ml of 0.5 N-hydrochloric acid, and the precipitate formed was collected by filtration, washed with ethanol, next with ethyl acetate to obtain 580 mg (yield: 83.8%).

Melting point: 228°-248° C. (decomposed).
Amino acid analysis:
  Asp: 2.07 (2)
  β-Ala 0.85 (1)
  Thr: 1.06 (1)
  Ser: 2.02 (2)
  Gly: 1.07 (1)
  Val: 0.92 (1)
  Leu: 2.00 (2)

REFERENCE EXAMPLE 80

Preparation of HCl.H-Cpc(OBu$^t$)-OCH$_3$

Under ice-cooling condition, to 30 ml of DMF solution containing 7.42 g of HCl.H-Cys-OCH$_3$ and 11.58 g of BrCH$_2$(CH$_2$)$_2$COOBu$^5$ was added 12.1 ml of triethylamine, and the mixture was stirred at room temperature for 2 days. The reaction mixture was poured into 100 ml of ice-water, then extracted with ethyl acetate (50 ml×3 times), the organic layers were combined and washed with 50 ml of water and 50 ml of saturated sodium chloride aqueous solution (twice), respectively, then was dried over anhydrous magnesium sulfate and concentrated under reduced pressure. To the residue thus obtained was added 20 ml of 4N-hydrochloric acid/dioxane under ice-cooling condition, the mixture was concentrated under reduced pressure and the residue obtained was crystallized by adding diethyl ether and recrystallized from ethyl acetate-diethyl ether. 9.30 Grams (yield: 68.5%) of the above-mentioned objective product was obtained.

Melting point: 90°–93° C.

REFERENCE EXAMPLE 81

Preparation of Boc-Thr(Bzl)-Cpc(OBu$^t$)-OCH$_3$

By using 1.30 g of HCl.H-Cpc(OBu$^t$)-OCH$_3$ and 1.85 g of Boc-Thr(Bzl)-OSu as well as 550 mg of HOBT, and the same procedure as in Reference Example 18 was repeated to obtain 1.92 g (yield: 81.5%) of the above-mentioned objective product.

Melting point: 53°–55° C.

REFERENCE EXAMPLE 82

Preparation of Boc-Ser(Bzl)-Thr(Bzl)-Cpc-OCH$_3$

By using 1.85 g of Boc-Thr(Bzl)-Cpc(OBu$^t$)-OCH$_3$ and 1.30 g of Boc-Ser(Bzl)-OSu and the same procedure as in Reference Example 18 was repeated to obtain 1.46 g (yield: 60.2%) of the above-mentioned objective product.

Appearance: Oily substance.

REFERENCE EXAMPLE 83

Preparation of Boc-Ser(Bzl)-Asn-Leu-Ser(Bzl)-Thr(Bzl)-Cpc-OCH$_3$

By using 1.46 g of Boc-Ser(Bzl)-Thr(Bzl)-Cpc-CH$_3$ and 1.36 g of Boc-Ser(Bzl)-Asn-Leu-NHNH$_2$ and the same procedure as in Reference Example 7 was repeated to obtain 1.66 g (yield: 73.6%) of the above-mentioned objective product.

Melting point: 183°–186° C.

REFERENCE EXAMPLE 84

Preparation of ⌐Ser(Bzl)—Asn—Leu—Ser(Bzl)—
     Thr(Bzl)—Cpc—OCH$_3$

By using 950 mg of Boc-Ser(Bzl)-Asn-Leu-Ser(Bzl)-Thr(Bzl)-Cpc-OCH$_3$ and the same procedure as in Reference Example 8 was repeated to obtain 450 mg (yield: 55.9%) of the above-mentioned objective product.

Melting point: 158°–161° C.

REFERENCE EXAMPLE 85

Preparation of ⌐Ser(Bzl)—Asn—Leu—Ser(Bzl)—
     Thr(Bzl)—Cpc—NHNH$_2$

By using 430 mg of

⌐Ser(Bzl)—Asn—Leu—Ser(Bzl)—
Thr(Bzl)—Cpc—OCH$_3$ and the same procedure as in Reference Example 9 was repeated to obtain 424 mg (yield: 98.5%) of the above-mentioned objective product.

Melting point: 208°–213° C.

REFERENCE EXAMPLE 86

Preparation of ⌐Ser(Bzl)—Asn—Leu—Ser(Bzl)—
     Thr(Bzl)—Cpc—Val—Leu—Gly—OH

By using 380 mg of

⌐Ser(Bzl)—Asn—Leu—Ser(Bzl)—
Thr(Bzl)—Cpc—NHNH$_2$ and 301 mg of Boc-Val-Leu-Gly-OH and the same procedure as in Reference Example 13 was repeated to obtain 371 mg (yield: 77.5%) of the above-mentioned objective product.

Melting point: 246°–256° C.

Amino acid analysis:
Asp: 1.03 (1)
Thr: 1.01 (1)
Ser: 1.92 (2)
Gly: 1.00 (1)
Val: 0.96 (1)
Leu: 2.07 (2)
Cpc: 1.00 (1)

REFERENCE EXAMPLE 87

Preparation of HCl.H-Cec(OBu$^t$)-OCH$_3$ 8.58 Grams of HCl.H-Cys-OCH$_3$ and 11.7 g of Br-CH$_2$CH$_2$-COOBu$^t$ were dissolved in 30 ml of DMF, to this solution was added, under ice-cooling condition, 14.7 ml of triethylamine, and the reaction mixture was stirred at room temperature for 48 hours. To the reaction mixture was added 100 ml of ice-water and extracted with ethyl acetate (50 ml×3 times). The ethyl acetate layers were combined together and washed with water (50 ml×once) and with a saturated sodium chloride aqueous solution (50 ml×twice), respectively, then dried over anhydrous magnesium sulfate and concentrated under reduced pressure. To the residue thus obtained was added 20 ml of 4N-hydrochloric acid/dioxane under ice-cooling condition, then the mixture was concentrated under reduced pressure, the residue thus obtained was crystallized by adding diethyl ether, and recrystallized from ethyl acetate-diethyl ether to obtain 11.4 g (yield: 76.0%) of the above-mentioned objective product.

Melting point: 65°–67° C.

REFERENCE EXAMPLE 88

Preparation of Boc-Thr(Bzl)-Cec(OBu$^t$)-OCH$_3$

By using 7.22 g of Boc-Thr(Bzl)-OSu and 7.70 g of [HCl.H-Cec(OBu$^t$)-OCH and the same procedure as in Reference Example 18 was repeated to obtain 9.31 g (yield: 71.9%) of the above-mentioned objective product.

Appearance: Oily substance.

REFERENCE EXAMPLE 89

Preparation of Boc-Ser(Bzl)-Thr(Bzl)-Cec-OCH$_3$

By using 9.05 g of Boc-Thr(Bzl)-Cec(OBu$^t$)-OCH$_3$ and 6.28 g of Boc-Ser(Bzl)-OSu and the same procedure as in Reference Example 18 was repeated to obtain 10.2 g (yield: 92.5%) of the above-mentioned objective product.

Appearance: Oily substance

REFERENCE EXAMPLE 90

Preparation of Boc-Abu-Asn-Leu-OEt

By using 6.50 g of Boc-Asn-Leu-OEt and 5.48 g of Boc-Abu-Osu and the same procedure as in Reference Example 18 was repeated to obtain 7.20 g (yield: 90.2%) of the above-mentioned objective product.

Melting point: 152°–155° C.

REFERENCE EXAMPLE 91

Preparation of Boc-Abu-Asn-Leu-NHNH$_2$

By using 6.23 g of Boc-Abu-Asn-Leu-OEt and the same procedure as in Reference Example 6 was repeated to obtain 4.47 g (yield: 74.0%) of the above-mentioned objective product.

Melting point: 205°–208° C.

REFERENCE EXAMPLE 92

Preparation of Boc-Abu-Asn-Leu-Ser(Bzl)-Thr(Bzl)-Cec-OCH$_3$

By using 2.63 g of Boc-Ser(bzl)-Thr(Bzl)-Cec-OCH$_3$ and 2.00 g of Boc-Abu-Asn-Leu-NHNH$_2$ and the same procedure as in Reference Example 7 was repeated to obtain 2.75 g (yield: 67.9%) of the above-mentioned objective product.

Melting point: 194°–198° C.

REFERENCE EXAMPLE 93

Preparation of

⌐Abu—Asn—Leu—Ser(Bzl)—Thr(Bzl)—Cec—OCH$_3$

By using 2.50 g of Boc-Abu-Asn-Leu-Ser(Bzl)-Thr(Bzl)-Cec-OCH$_3$ and the same procedure as in Reference Example 8 was repeated to obtain 1.04 g (yield: 47.1%) of the above-mentioned objective product.

Melting point: 222°–226° C.

REFERENCE EXAMPLE 94

Preparation of

⌐Abu—Asn—Leu—Ser(Bzl)—Thr(Bzl)—Cec—NHNH$_2$

By using 950 mg of

⌐Abu—Asn—Leu—Ser(Bzl)—Thr(Bzl)—Cec—OCH$_3$ and the same procedure as in Reference Example 9 was repeated to obtain 641 mg (yield: 66.8%) of the above-mentioned objective product.

Melting point: 205°–220° C.

Amino acid analysis:

| Amino acid analysis: | |
|---|---|
| Asp: 1.02 (1) | Thr: 1.00 (1) |
| Ser: 0.94 (1) | Leu: 1.06 (1) |
| Abu: 1.21 (1) | Cec: 0.98 (1) |

REFERENCE EXAMPLE 95

Preparation of ⌐Abu—Asn—Leu—Ser(Bzl)—Thr(Bzl)—Cec—Val—Leu—Gly—OH

Bu using 508 mg of Boc-Val-Leu-Gly-OH and 550 mg of

⌐Abu—Asn—Leu—Ser(Bzl)—Thr(Bzl)—Cec—NHNH$_2$ and the same procedure as in Reference Example 13 was repeated to obtain 504 mg (yield: 70.2%) of the above-mentioned objective product. Melting point: 242°–249° C. (decomposed).

REFERENCE EXAMPLE 96

Preparation of Z-Tyr(CH$_2$COOBzl)-OCH$_3$

Under ice-cooling condition, to 25 ml of DMF solution containing 5.70 g of Z-Tyr-OCH$_3$ was added 692 mg of sodium hydride (containing 60%) and the mixture was stirred for 30 minutes, then 3.96 g of benzyl bromoacetate was added thereto and the whole mixture was stirred at 50° C. for 1 hour. The reaction mixture was concentrated under reduced pressure and the residue thus obtained was extracted with 100 ml of ethyl acetate. The ethyl acetate layer was washed with water and a saturated sodium chloride aqueous solution twice, respectively, then dried over anhydrous sodium sulfate and concentrated under reduced pressure. The residue thus obtained was added to a silica gel column and eluted with petroleum ether-chloroform (1:4) to obtain 6.00 g (yield: 72.6%) of the above-mentioned objective product.

Appearance: Oily substance.

NMR(CDCl$_3$) δ:

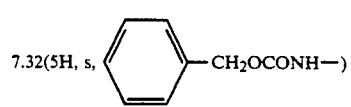

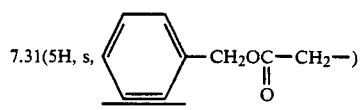

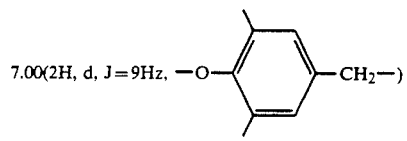

-continued 6.77(2H, d, J=9Hz, 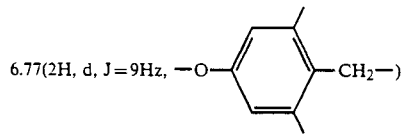

5.21(2H, s, 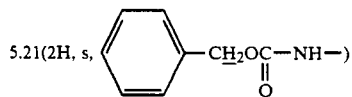

5.07(2H, s, 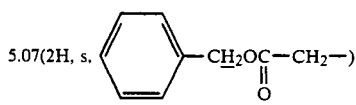

4.70–4.55(3H, m, 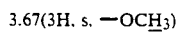 NH—CH—CO, —OC$\underline{H}_2$—COO—)

3.67(3H, s, —OC$\underline{H}_3$)

3.02(2H, d, J=6Hz, 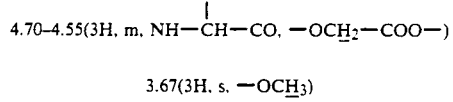

REFERENCE EXAMPLE 97

Preparation of Boc-Thr(Bzl)-Tyr(CH$_2$COOH)-OCH$_3$

To 50 ml of THF solution containing 5.80 g of Z-Tyr(CH$_2$COOBzl)-OCH$_3$ were added 12 ml of 1N-hydrochloric acid and 300 mg of 10%-palladium-carbon, and the mixture was subjected to catalytic reduction in hydrogen gas stream. After the reaction was finished, the 10%-palladium carbon was removed by filtration, and the filtrate was concentrated under reduced pressure to dryness.

By using the residue thus obtained and 4.92 g of Boc-Thr(Bzl)-OSu and the same procedure as in Reference Example 72 was repeated to obtain 5.00 g (yield: 75.7%) of the above-mentioned objective product.

Melting point: 101°–106° C.

REFERENCE EXAMPLE 98

Preparation of Boc-Ser(Bzl)-Thr(Bzl)-Tyr(CH$_2$-COOH)-OCH$_3$

By using 4.90 g of Boc-Thr(Bzl)-Tyr(CH$_2$COOH)-OCH$_3$ and 4.23 g of Boc-Ser(Bzl)-OSu and the same procedure as in Reference Example 18 was repeated to obtain 4.51 g (yield: (yield: 69.5%) of the above-mentioned objective product.

Appearance: Oily substance

REFERENCE EXAMPLE 99

Preparation of Boc-Ser(Bzl)-Asn-Leu-Ser(Bzl)-Thr(Bzl)-Tyr(CH$_2$COOH)-OCH$_3$

By using 2.50 g of Boc-Ser(Bzl)-Thr(Bzl)-Tyr(CH$_2$COOH)-OCH$_3$ and 2.23 g of Boc-Ser(Bzl)-Asn-Leu-NHNH$_2$ and the same procedure as in Reference Example 7 was repeated to obtain 2.49 g (yield: 63.8%) of the above-mentioned objective product.

Melting point: 186°–190° C.

REFERENCE EXAMPLE 100

Preparation of 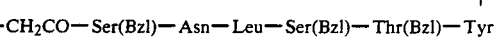
—CH$_2$CO—Ser(Bzl)—Asn—Leu—Ser(Bzl)—Thr(Bzl)—Tyr—NHNH$_2$ By using 2.43 g of Boc-Ser(Bzl)-Asn-Leu-Ser(Bzl)-Thr(Bzl)-Tyr(CH$_2$COOH)-OCH$_3$ and the same procedures as in Reference Example 8 and in Reference Example 9 were repeated to obtain 950 mg (yield: 43.8%) of the above-mentioned objective product.

Melting point: 202°–208° C.

REFERENCE EXAMPLE 101

Preparation of 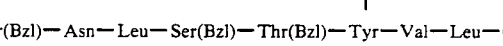
—CH$_2$CO—Ser(Bzl)—Asn—Leu—Ser(Bzl)—Thr(Bzl)—Tyr—Val—Leu—Gly—OH By using 450 mg of

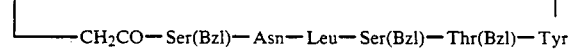
—CH$_2$CO—Ser(Bzl)—Asn—Leu—Ser(Bzl)—Thr(Bzl)—Tyr—NHNH$_2$ anf 349 mg of Boc-Val-Leu-Gly-OH, and the same procedure as in Reference Example 13 was repeated to obtain 430 mg (yield: 75.6%) of the above-mentioned product.

Melting point: 229°–232° C. (decomposed)

REFERENCE EXAMPLE 102

Preparation of Z-Lys(COCH$_2$CH$_2$COOH)-OCH$_3$ 5.00 Grams of Z-Lys(Boc)-OCH$_3$ was dissolved by adding 15 ml of TFA, and the solution was stirred at room temperature for 30 minutes. The reaction mixture was concentrated under reduced pressure, to the residue thus obtained was added petroleum ether, and the oily product formed was separated by decantation and dried over sodium hydroxide under reduced pressure.

The above-mentioned product was dissolved in 40 ml of pyridine under ice-cooling condition, to this solution was added 3.08 g of succinic anhydride, then the whole mixture was stirred at room temperature for 18 hours. The reaction mixture was concentrated under reduced pressure, and the residue thus obtained was extracted with 100 ml of ethyl acetate, then the ethyl acetate layer was washed with 1N-hydrochloric acid, next with a saturated sodium chloride aqueous solution three times and was dried over anhydrous sodium sulfate, and concentrated under reduced pressure. The residue thus obtained was dissolved in chloroform, then this solution was added to a silica gel column and eluted with 200 ml of chloroform, next with 400 ml of 3%-methanol/-chloroform to purify and obtained 3.63 g (yield: 71.9%) of the above-mentioned objective product as an oily substance.

NMR (CDCl$_3$) δ:
7.27–7.33 (6H, m, CH$_2$C$_6$H$_5$, OCONH or CONH);
6.34–6.07 (1H, bs, OCONH or CONH);
5.10 (2H, s, CH$_2$C$_6$H$_5$);
4,41–4,15 (1H, m, NHCHCO);
3.71 (3H, s, OCH$_3$);
3.25–3.13 (2H, m, NHCH$_2$-);
2.76–2.34 (4H, m, COCH$_2$CH$_2$CO);
1.89–1.15 (6H, m, NHCH$_2$(CH$_2$)$_3$)

REFERENCE EXAMPLE 103

Preparation of
Boc-Thr(Bzl)-Lys(COCH$_2$CH$_2$COOH)-OCH$_3$ 3.60 Grams of Z-Lys(COCH$_2$CH$_2$COOH)-OCH$_3$ was dissolved in 30 ml of methanol, to this solution was added 100 mg of 5%-palladium-carbon and 9.13 ml of 1N-hydrochloric acid, and the mixture was subjected to a catalytic reduction in a hydrogen gas stream. After finishing the reaction, the catalyst was removed by filtration, and the filtrate was concentrated under reduced pressure, the residue thus obtained was dried over sodium hydroxide under reduced pressure. Then the residue thus obtained was dissolved in a mixture of 30 ml of THF and 5 ml of water, and under ice-cooling condition, the pH of this mixture was adjusted to pH 6–7 by adding triethylamine. To this mixture was added 4.08 g of Boc-Thr(Bzl)-OSu, then the pH of this mixture was adjusted to pH 7–8 by adding N-methylmorpholine, and stirred under ice-cooling condition for 1 hour, next at room temperature for 18 hours. The reaction mixture was concentrated under reduced pressure, and the residue thus obtained was extracted with 50 ml of ethyl acetate. The ethyl acetate layer was washed with 1N-hydrochloric acid, next with a saturated sodium chloride aqueous solution three times, then was dried over anhydrous sodium sulfate, and was concentrated under reduced pressure. The residue thus obtained was dissolved in chloroform and was added to a silica gel column, eluted with 200 ml of chloroform, next with 500 ml of 2%-methanol/chloroform to obtain the fraction containing the objective product, then concentrated under reduced pressure, and the residue thus obtained was solidified by adding diethyl ether. 960 Milligrams (yield: 19.1%) of the above-mentioned objective product was obtained.

Melting point: 60°–63° C.

REFERENCE EXAMPLE 104

Preparation of
Boc-Ser(Bzl)-Thr(Bzl)-Lys(COCH$_2$-CH$_2$COOH)-OCH$_3$.1/2H$_2$O

900 Milligrams of Boc-Thr(Bzl)-Lys(COCH$_2$CH$_2$COOH)-OCH$_3$ was dissolved by adding 2 ml of TFA, and this solution stirred at room temperature for 30 minutes. The reaction mixture was concentrated under reduced pressure, the residue thus obtained was dried over sodium hydroxide under reduced pressure. To this residue was added 30 ml of THF, under ice-cooling condition, the pH of this solution was adjusted by adding pH 6-7. To this solution was added 768 mg of Boc-Ser(Bzl)-OSu, and the pH of this mixture was adjusted by adding N-methylmorpholine to pH 7–8, then was stirred for 1 hour under ice-cooling condition, next stirred at room temperature for 40 hours. The reaction mixture was concentrated under reduced pressure, and the residue thus obtained was extracted with 30 ml of ethyl acetate, and the ethyl acetate layer was washed with 1N-hydrochloric acid, a saturated sodium chloride aqueous solution, a saturated sodium hydrogen carbonate aqueous solution twice, and with water three times, respectively, then concentrated under reduced pressure. To the residue thus obtained was added ethanol and again concentrated under reduced pressure, the residue thus obtained was solidified by adding diethyl ether, and re-precipitated from methanol-diethyl ether. 810 Milligrams (yield: 67.4%) of the above-mentioned objective product was obtained.

Melting point: 81°–83° C.

REFERENCE EXAMPLE 105

Preparation of Boc-Asn-Leu-NHNH$_2$

By using 3.00 g of Boc-Asn-Leu-OEt, and the same procedure as in Reference Example 6 was repeated to obtain 2.45 g (yield: 81.7%) of the above-mentioned objective product.

Melting point: 219°–221° C.

REFERENCE EXAMPLE 106

Preparation of
Boc-Asn-Leu-Ser(Bzl)-Thr(Bzl)-Lys(COCH$_2$CH$_2$COOH)-OCH$_3$

By using 3.60 g of Boc-Ser(Bzl)-Thr(Bzl)-Lys(COCH$_2$CH$_2$COOH)-OCH$_3$ and 2.21 g of Boc-Asn-Leu-NHNH$_2$, and the same procedure as in Reference Example 7 was repeated to obtain 3.37 g (yield: 71.4%) of the above-mentioned objective product.

Melting point: 206°–209° C.

REFERENCE EXAMPLE 107

Preparation of ⌐COCH$_2$CH$_2$CO—Asn—Leu—Ser(Bzl)—Thr(Bzl)—Lys—OCH$_3$⌐

By using 3.27 g of Boc-Asn-Leu-Ser(Bzl)-Thr(Bzl)-Lys(COCH$_2$CH$_2$-COOH)-OCH$_3$, and the same procedure as in Reference Example 8 was repeated to obtain 1.00 g (yield: 34.9%) of the above-mentioned product.

Melting point: 115°–117° C.

REFERENCE EXAMPLE 108

Preparation of ⌐COCH$_2$CH$_2$CO—Asn—Leu—Ser(Bzl)—Thr(Bzl)—Lys—NHNH$_2$⌐

By using 850 mg of

By using 850 mg of ⌐COCH₂CH₂CO—Asn—Leu—Ser(Bzl)—Thr(Bzl)—Lys—OCH₃, and the same procedure as in Reference Example 9 was repeated to obtain 630 mg (yield: 73.8%) of the above-mentioned objective product.
Melting point: 170°–183° C.
Amino acid analysis:
Asp: 1.01 (1)
Thr: 0.99 (1)
Ser: 0.93 (1)
Leu: 1.07 (1)
Lys: 0.85 (1)

REFERENCE EXAMPLE 109

Preparation of ⌐COCH₂CH₂CO—Asn—Leu—Ser(Bzl)—Thr(Bzl)—Lys—Val—Leu—Gly—OH

By using 580 mg of

⌐COCH₂CH₂CO—Asn—Leu—Ser(Bzl)—Thr(Bzl)—Lys—NHNH₂ and 535 mg of Boc-Val-Leu-Gly-OH, and the same procedure as in Reference Example 13 was repeated to obtain 540 mg (yield: 71.7%) of the above-mentioned product. Melting point: 245°–249° C. (decomposed).

REFERENCE EXAMPLE 110

Preparation of Boc-Leu-Gly-OH 2.63 Grams of H-Gly-OH and 3.50 g of sodium hydrogen carbonate were suspended in 50 ml of water, to this supension was added, under ice-cooling condition, 50 ml of dioxane solution containing 10.0 g of Boc-Leu-OSu, and stirred for 30 minutes, then this mixture was further stirred at room temperature for 15 hours. The reaction mixture was concentrated under reduced pressure, and the residue thus obtained was extracted with ethyl acetate (70 ml). The ethyl acetate layer was washed with 1N-hydrochloric acid, and with a saturated sodium chloride aqueous solution, then was dried over anhydrous magnesium sulfate, and concentrated under reduced pressure. The residue thus obtained was recrystalled from ethyl acetate-n-hexane to obtain 6.65 g (yield: 75.7%) of the above-mentioned objective product.
Melting point: 115°–123° C.

REFERENCE EXAMPLE 111

Preparation of Boc-Gly-Leu-Gly-OH

By using 6.41 g of Boc-Leu-Gly-OH and 6.04 g of Boc-Gly-OSu, and the same procedure as in Reference Example 31 was repaeted to obtain 4.67 g (yield: 61.4%) of the above-mentioned objective product.
Melting point: 67°–70° C.

REFERENCE EXAMPLE 112

Preparation of ⌐Gly—Ser(Bzl)—Asn—Leu—Ser(Bzl)—Thr(Bzl)—Glu—Gly—Leu—Gly—OH

By using 550 mg of

⌐Gly—Ser(Bzl)—Asn—Leu—Ser(Bzl)—Thr(Bzl)—Glu—NHNH₂ and 280 mg of H-Gly-Leu-Gly-OH, and the same procedure as in Reference Example 13 was repeated to obtain 310 mg (yield: 46.2%) of the above-mentioned objective product.
Melting point: 208°–211° C.

REFERENCE EXAMPLE 113

Preparation of Boc-Ile-Leu-Gly-OEt

By using 2.00 g of Boc-Leu-Gly-OEt and 1.67 g of Boc-Ile-OH.1/2H₂O and the same procedure as in Reference Example 15 was repeated to obtain 1.99 g (yield: 73.3%) of the above-mentioned objective product.
Melting point: 123°–124° C.

REFERENCE EXAMPLE 114

Preparation of Boc-Ile-Leu-Gly-OH

By using 1.89 g Boc-Ile-Leu-Gly-OEt and the same procedure as in Reference Example 12 was repeated to obtain 1.53 g (yield: 86.6%) of the above-mentioned objective product.
Appearance: Oily substance
Amino acid analysis:
Gly: 1.07 (1)
Ile: 0.96 (1)
Leu: 0.97 (1)

REFERENCE EXAMPLE 115

Preparation of ⌐Gly—Ser(Bzl)—Asn—Leu—Ser(Bzl)—Thr(Bzl)—Glu—Ile—Leu—Gly—OH

By using 600 mg of Boc-Ile-Leu-Gly-OH and 500 mg of

⌐Gly—Ser(Bzl)—Asn—Leu—Ser(Bzl)—Thr(Bzl)—Glu—NHNH₂ and the same procedure as in Reference Example 13 was repeated to obtain 580 mg (yield: 90.9%) of the above-mentioned objective product.
Melting point: 243°–247° C.

REFERENCE EXAMPLE 116

Preparation of
Boc-Ala-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 700 mg of Boc-Lys(Cl-Z)-Leu-Gln-Thr(Bzl)-Pro-Arg(Tos)-Thr(Bzl)-Asn-Thr(Bzl)-GLy-Ser(Bzl)-Gly -Thr(Bzl)-Pro-NH₂ and 83 mg of Boc-Ala-OH, and the same procedure as in Reference Example 15 was repeated to obtain 664 mg (yield: 91.4%) of the above-mentioned objective product.
Melting point: 135°–140° C.

REFERENCE EXAMPLE 117

Preparation of
Boc-Ser(Bzl)-Gln-Glu(OcHex)-Leu-Ala-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 650 mg of Boc-Ala-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH₂ and 310 mg of Boc-Ser(Bzl)-Gln-Glu(OcHex)-Leu-OH, and the same procedure as in Reference Example 15 was repeated to obtain 842 mg (yield: 98.5%) of the above-mentioned objective product.
Melting point: 212°–226° C. (decomposed).
Amino acid analysis:
  Asp: 1.03 (1)
  Thr: 3.87 (4)
  Ser: 2.05 (2)
  Glu: 3.59 (3)
  Gly: 2.04 (2)
  Ala: 1.00 (1)
  Leu: 2.20 (2)
  Lys: 1.00 (1)
  Arg: 1.01 (1)
  Pro: 2.00 (2)

REFERENCE EXAMPLE 118

Preparation of
Boc-Lys(Cl-Z)-Leu-Ser(Bzl)-Gln-Glu(OcHex)-Leu-Ala-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 800 mg of Boc-Ser(Bzl)-Gln-Glu(OcHex)-Leu-Ala-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH₂ and 210 mg of Boc-Lys(Cl-Z)-Leu-OH, and the same procedure as in Reference Example 15 was repeated to obtain 839 mg (yield: 90.8%) of the above-mentioned objective product.
Melting point: 215°–217° C. (decomposed).

REFERENCE EXAMPLE 119

Preparation of
Boc-Ser(Bzl)-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 700 mg of Boc-Lys(Cl-Z)-Leu-Gln-Thr(Bzl)-Pro-Arg(Tos)-Thr(Bzl)-Asn-Thr(Bzl)-Gly-Ser(Bzl)-Gly -Thr(Bzl)-Pro-NH₂ and 215 mg of Boc-Ser(Bzl)-OSu, and the same procedure as in Reference Example 18 was repeated to obtain 722 mg (yield: 94.3%) of the above-mentioned objective product.
Melting point: 168°–177° C.

REFERENCE EXAMPLE 120

Preparation of
Boc-Ser(Bzl)-Gln-Glu(OcHex)-Leu-Ser(Bzl)-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 700 mg of Boc-Ser(Bzl)-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH₂ and 318 mg of Boc-Ser(Bzl)-Gln-Glu(OcHex)-Leu-OH, and the same procedure as in Reference Example 15 was repeated to obtain 902 mg (yield: 99.1%) of the above-mentioned objective product.
Melting point: 214°–224° C. (decomposed).
Amino acid analysis:
  Asp: 1.01 (1)
  Thr: 3.79 (4)
  Ser: 2.73 (3)
  Glu: 3.21 (3)
  Gly: 2.00 (2)
  Leu: 2.04 (2)
  Lys: 0.99 (1)
  Arg: 1.00 (1)
  Pro: 1.95 (2)

REFERENCE EXAMPLE 121

Preparation of
Boc-Lys(Cl-Z)-Leu-Ser(Bzl)-Gln-Glu(OcHex)-Leu-Ser(Bzl)-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH₂

By using 850 mg of Boc-Ser(Bzl)-Gln-Glu(OcHex)-Leu-Ser(Bzl)-Lys(Cl-Z)-Leu-Gln-Thr(Bzl)-Pro-Arg(Tos) -Thr(Bzl)-Asn-Thr(Bzl)-Gly-Ser(Bzl)-Gly-Thr(Bzl)-Pro-NH₂ and 214 mg of Boc-Lys(Cl-Z)-Leu-OH, and the same procedure as in Reference Example 15 was repeated to obtain 862 mg (yield: 88.2%) of the above-mentioned objective product.
Melting point: 222°–225° C. (decomposed).

REFERENCE EXAMPLE 122

Preparation of
Boc-Leu-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 700 mg of Boc-Lys(Cl-Z)-Leu-Gln-Thr(Bzl)-Pro-Arg(Tos)-Thr(Bzl)-Asn-Thr(Bzl)-Gly-Ser(Bzl)-Gly -Thr(Bzl)-Pro-NH$_2$ and 180 mg of Boc-Leu-OSu, and the same procedure as in Reference Example 18 was repeated to obtain 714 mg (yield: 96.2%) of the above-mentioned objective product.

Melting point: 178°–184° C.

REFERENCE EXAMPLE 123

Preparation of
Boc-Ser(Bzl)-Gln-Glu(OcHex)-Leu-Leu-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 670 mg of Boc-Leu-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH$_2$ and 314 mg of Boc-Ser(Bzl)-Gln-Glu(OcHex)-Leu-OH and the same procedure as in Reference Example 15 was repeated to obtain 811 mg (yield: 92.3%) of Melting point: 223°–236° C. (decomposed).
Amino acid analysis:
  Asp: 1.02 (1)
  Thr: 3.84 (4)
  Ser: 1.89 (2)
  Glu: 3.33 (3)
  Gly: 2.04 (2)
  Leu: 3.16 (3)
  Lys: 1.00 (1)
  Arg: 1.03 (1)
  Pro: 2.00 (2)

REFERENCE EXAMPLE 124

Preparation of
Boc-Lys(Cl-Z)-Leu-Ser(Bzl)-Gln-Glu(OcHex)-Leu-Leu-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 750 mg of Boc-Ser(Bzl)-Gln-Glu(OcHex)-Leu-Leu-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH$_2$ and 193 mg of Boc-Lys(Cl-Z)-Leu-OH, and the same procedure as in Reference Example 15 was repeated to obtain 763 mg (yield: 88.0%) of the above-mentioned objective product.

Melting point: 220°–234° C. (decomposed).
Amino acid analysis:
  Asp: 1.02 (1)
  Thr: 3.74 (4)
  Ser: 1.76 (2)
  Glu: 3.23 (3)
  Gly: 2.02 (2)
  Leu: 4.02 (4)
  Lys: 1.95 (2)
  Arg: 1.01 (1)
  Pro: 1.98 (2)

REFERENCE EXAMPLE 125

Preparation of
Boc-Gln-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 700 mg of Boc-Lys(Cl-Z)-Leu-Gln-Thr(Bzl)-Pro-Arg(Tos)-Thr(Bzl)-Asn-Thr(Bzl)-Gly-Ser(Bzl)-Gly -Thr(Bzl)-Pro-NH$_2$ and 161 mg of Boc-Gln-ONp, and the same procedure as in Reference Example 18 was repeated to obtain 697 mg (yield: 93.2%) of the above-mentioned objective product.

Melting point: 128°–133° C.

REFERENCE EXAMPLE 126

Preparation of
Boc-Ser(Bzl)-Gln-Glu(OcHex)-Leu-Gln-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 650 mg of Boc-Gln-Lys(Cl-Z)-Leu-Gln-Thr(Bzl)-Pro-Arg(Tos)-Thr(Bzl)-Asn-Thr(Bzl)-Gly-Ser(Bzl) -Gly-Thr(Bzl)-Pro-NH$_2$ and 302 mg of Boc-Ser(Bzl)-Gln-Glu(OcHex)-Leu-OH, and the same procedure as in Reference Example 15 was repeated to obtain 786 mg (yield: 92.6%) of the above-mentioned objective product.

Melting point: 210°–219° C. (decomposed).

REFERENCE EXAMPLE 127

Preparation of
Boc-Lys(Cl-Z)-Leu-Ser(Bzl)-Gln-Glu(OcHex)-Leu-Gln-Lys(Cl-Z)-Leu-Gln-Thr(Bzl)-Pro-Arg(Tos)-Thr(Bzl)-Asn-Thr(Bzl)-Gly-Ser(Bzl)-Gly-Thr(Bzl)-Pro-NH$_2$ By using 750 mg of Boc-Ser(Bzl)-Gln-Glu(OcHex)-Leu-Gln-Lys(Cl-Z)-Leu-Gln-Thr(Bzl)-Pro-Arg(Tos)-Thr(Bzl) -Asn-Thr(Bzl)-Gly-Ser(Bzl)-Gly-Thr(Bzl)-Pro-NH$_2$ and 192 mg of Boc-Lys(Cl-Z)-Leu-OH, and the same procedure as in Reference Example 15 was repeated to obtain 783 mg (yield: 90.6%) of the above-mentioned objective product.

Melting point: 217°–228° C. (decomposed).
Amino acid analysis:
  Asp: 1.01 (1)
  Thr: 3.73 (4)
  Ser: 1.93 (2)
  Glu: 4.62 (4)
  Gly: 2.01 (2)
  Leu: 3.28 (3)
  Lys: 2.05 (2)
  Arg: 1.01 (1)
  Pro: 1.99 (2)

REFERENCE EXAMPLE 128

Preparation of
Boc-Ala-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro-NH$_2$ By using 650 mg of Boc-Lys(Cl-Z)-Leu-Gln-Thr(Bzl)-Pro-Gln-Thr(Bzl)-Asn-Thr(Bzl)-Gly-Ser(Bzl)-Gly-Thr(Bzl)-Pro -NH$_2$ and 74 mg of Boc-Ala-OH, and the same procedure as in Reference Example 15 was repeated to obtain 616 mg (yield: 91.6%) of the above-mentioned objective product.

Melting point: 217°–223° C.

REFERENCE EXAMPLE 129

Preparation of
Boc-Ser(Bzl)-Gln-Glu(OcHex)-Leu-Ala-Lys(Cl-Z)-
Leu-Gln-Thr(Bzl)-Pro-Gln-Thr(Bzl)-Asn
-Thr(Bzl)-Gly-Ser(Bzl)-Gly-Thr(Bzl)-Pro-NH$_2$ By using 580 mg of Boc-Ala-Lys(Cl-Z)-Leu-Gln-Thr(Bzl)-Pro-Gln-Thr(Bzl)-Asn-Thr(Bzl)-Gly-Ser(Bzl)-Gly -Thr(Bzl)-Pro-NH$_2$ and 229 mg of Boc-Ser(Bzl)-Gln-Glu(OcHex)-Leu-OH, and the same procedure as in Reference Example 15 was repeated to obtain 754 mg (yield: 101%) of the above-mentioned objective product.

Melting point: 237°–241° C. (decomposed).

REFERENCE EXAMPLE 130

Preparation of
Boc-Lys(Cl-Z)-Leu-Ser(Bzl)-Gln-Glu(OcHex)-Leu-
Ala-Lys(Cl-Z)-Leu-Gln-Thr(Bzl)-Pro-Gln
-Thr(Bzl)-Asn-Thr(Bzl)-Gly-Ser(Bzl)-Gly-Thr(Bzl)-
Pro-NH$_2$ By using 720 mg of Boc-Ser(Bzl)-Gln-Glu(OcHex)-Leu-Ala-Lys(Cl-Z)-Leu-Gln-Thr(Bzl)-Pro-Gln-Thr(Bzl)-Asn -Thr(Bzl)-Gly-Ser(Bzl)-Gly-Thr(Bzl)- Pro-NH$_2$ and 174 mg of Boc-Lys(Cl-Z)-Leu-OH, and the same procedure as in Reference Example 15 was repeated to obtain 619 mg (yield: 75.1%) of the above-mentioned objective product.

Melting point: 207°–238° C. (decomposed).
Amino acid analysis:
  Asp: 1.04 (1)
  Thr: 3.94 (4)
  Ser: 1.72 (2)
  Glu: 4.23 (4)
  Gly: 2.03 (2)
  Ala: 0.95 (1)
  Leu: 2.72 (3)
  Lys: 1.66 (2)
  Pro: 2.04 (2)

REFERENCE EXAMPLE 131

Preparation of
Boc-Ser(Bzl)-Lys(Cl-Z)-Leu-Gln-Thr(Bzl)-Pro-Gln-
Thr(Bzl)-Asn-Thr(Bzl)-Gly-Ser(Bzl)-Gly
-Thr(Bzl)-Pro-NH$_2$ By using 650 mg of Boc-Lys(Cl-Z)-Leu-Gln-Thr(Bzl)-Pro-Gln-Thr(Bzl)-Asn-Thr(Bzl)-Gly-Ser(Bzl)-Gly-Thr(Bzl) -Pro-NH$_2$ and 154 mg of Boc-Ser(Bzl)-OSu, and the same procedure as in Reference Example 18 was repeated to obtain 648 mg (yield: 92.0%) of the above-mentioned objective product.

Melting point: 214°–220° C.

REFERENCE EXAMPLE 132

Preparation of
Boc-Ser(Bzl)-Gln-Glu(OcHex)-Leu-Ser(Bzl)-Lys(Cl-
Z)-Leu-Gln-Thr(Bzl)-Pro-Gln-Thr(Bzl)-Asn
-Thr(Bzl)-Gly-Ser(Bzl)-Gly-Thr(Bzl)-Pro-NH$_2$ By using 600 mg of Boc-Ser(Bzl)-Lys(Cl-Z)-Leu-Gln-Thr(Bzl)-Pro-Gln-Thr(Bzl)-Asn-Thr(Bzl)-Gly-Ser(Bzl) -Gly-Thr(Bzl)-Pro-NH$_2$ and 209 mg of Boc-Ser(Bzl)-Gln-Glu(OcHex)-Leu-OH, and the same procedure as in Reference Example 15 was repeated to obtain 759 mg (yield: 99.5%) of the above-mentioned objective product.

Melting point: 228°–236° C.

REFERENCE EXAMPLE 133

Preparation of
Boc-Lys(Cl-Z)-Leu-Ser(Bzl)-Gln-Glu(OcHex)-Leu-
Ser(Bzl)-Lys(Cl-Z)-Leu-Gln-Thr(Bzl)-Pro-Gln
-Thr(Bzl)-Asn-Thr(Bzl)-Gly-Ser(Bzl)-Gly-Thr(Bzl)-
Pro-NH$_2$ By using 720 mg of Boc-Ser(Bzl)-Gln-Glu(OcHex)-Leu-Ser(Bzl)-Lys(Cl-Z)-Leu-Gln-Thr(Bzl)-Pro-Gln-Thr(Bzl) -Asn-Thr(Bzl)-Gly-Ser(Bzl)-Gly-Thr(Bzl)-Pro-NH$_2$ and 155 mg of Boc-Lys(Cl-Z)-Leu-OH, and the same procedure as in Reference Example 15 was repeated to obtain 762 mg (yield; 92.8%) of the above-mentioned objective product.

Melting point: 211°–232° C. (decomposed). Amino acid analysis:
  Asp: 1.01 (1)
  Thr: 3.81 (4)
  Ser: 2.84 (3)
  Glu: 4.25 (4)
  Gly: 1.97 (2)
  Leu: 3.13 (3)
  Lys: 1.99 (2)
  Pro: 2.01 (2)

REFERENCE EXAMPLE 134

Preparation of
Boc-Asp(OcHex)-Val-Gly-Ala-Gly-Thr(Bzl)-Pro-NH$_2$

Under ice-cooling condition, 10.35 g of Boc-Val-Gly-Thr(Bzl)-Pro-NH$_2$ was dissolved by adding 30 ml of TFA, and the solution was stirred at room temperature for 30 minutes. The reaction mixture was concentrated under reduced pressure, and the residue thus obtained was treated by adding diethyl ether, and the product thus precipitated was collected by filtration and dried over sodium hydroxide under reduced pressure. This product was dissolved by adding 100 ml of THF, under ice cooling condition, this solution was neutralized with triethylamine. Then, to this solution was added 5.36 g of Boc-Asp(OcHex)-OH, 2.30 g of HOBT and 3.10 ml of WSC , then the mixture was stirred under ice-cooling condition for 2 hours, next stirred at room temperature overnight. The reaction mixture was concentrated under reduced pressure, then the residue thus obtained was extracted with 300 ml of chloroform. The chloroform layer was washed with 1N-hydrochloric acid (100 ml×2 times), a saturated sodium hydrogen carbonate aqueous solution (100 ml×2 times) and a saturated sodium chloride aqueous solution (100 ml×2 times) in this order, then was dried over anhydrous magnesium sulfate and concentrated under reduced pressure. The residue thus obtained was crystallized by adding diethyl ether, and the crystals formed were collected by filtration to obtain 11.05 g (yield: 83.0%) of the above-mentioned objective product.

Melting point: 228°–230° C.
Amino acid analysis:
  Asp: 0.99 (1)
  Thr: 0.99 (1)
  Gly: 2.01 (2)
  Ala: 1.00 (1)
  Val: 1.00 (1)
  Pro: 1.01 (1)

REFERENCE EXAMPLE 135

Preparation of
Boc-Thr(Bzl)-Asp(OcHex)-Val-Gly-ALa-Gly-Thr(Bzl)-Pro-NH$_2$

By using 10.00 g of Boc-Asp(OcHex)-Val-Gly-Ala-Gly-Thr(Bzl)-Pro-NH$_2$ and 5.50 g of Boc-Thr(Bzl)-OH, and the same procedure as in Reference Example 15 was repeated to obtain 10.29 g (yield: 84.5%) of the above-mentioned objective product.

Melting point: 168°–171° C.
Amino acid analysis:
Asp: 0.99 (1)
Thr: 1.95 (2)
Gly: 2.03 (2)
Ala: 1.00 (1)
Val: 1.01 (1)
Pro: 1.02 (1)

REFERENCE EXAMPLE 136

Preparation of
Boc-Arg(Tos)-Thr(Bzl)-Asp(OcHex)-Val-Gly-Ala-Gly-Thr(Bzl)-Pro-NH$_2$ By using 10.00 g of Boc-Thr(Bzl)-Asp(OcHex)-Val-Gly-Ala-Gly-Thr(Bzl)-Pro-NH$_2$ and 5.79 g of Boc-Arg(Tos)-OH. CH$_3$COOC$_2$H$_5$.1/5H$_2$O, and the same procedure as in Reference Example 15 was repeated to obtain 11.5 g (yield: 89.7%) of the above-mentioned objective product.

Melting point: 221°–226° C.
Amino acid analysis:
Asp: 0.99 (1)
Thr: 1.96 (2)
Gly: 1.99 (2)
Ala: 0.98 (1)
Val: 1.04 (1)
Arg: 1.01 (1)
Pro: 1.03 (1)

REFERENCE EXAMPLE 137

Preparation of
Boc-Thr(Bzl)-Pro-Arg(Tos)-Thr(Bzl)-Asp(OcHex)-Val-Gly-Ala-Gly-Thr(Bzl)-Pro-NH$_2$ By using 2.00 g of Boc-Arg(Tos)-Thr(Bzl)-Asp(OcHex)-Val-Gly-Ala-Gly-Thr(Bzl)-Pro-NH$_2$ and 878 mg of Boc-Thr(Bzl)-Pro-OH, and the same procedure as in Reference Example was repeated to obtain 2.00 g (yield: 82.8%) of the above-mentioned objective product.

Melting point: 199°–201° C.
Amino acid analysis:
Asp: 1.00 (1)
Thr: 2.96 (3)
Gly: 2.00 (2)
Ala: 0.99 (1)
Val: 1.00 (1)
Arg: 1.01 (1)
Pro: 2.04 (2)

REFERENCE EXAMPLE 138

Preparation of
Boc-Gln-Thr(Bzl)-Pro-Arg(Tos)-Thr(Bzl)-Asp(OcHex)-Val-Gly-Ala-Gly-Thr(Bzl)-Pro-NH$_2$ 1.95 Grams of Boc-Thr(Bzl)-Pro-Arg(Tos)-Thr(Bzl)-Asp(OcHex)-Val-Gly-Ala-Gly-Thr(Bzl)-Pro-NH$_2$ was dissolved by adding 6 ml of TFA, and the solution was stirred at room temperature for 30 minutes. The reaction mixture was concentrated under reduced pressure, and the residue thus obtained was treated by adding diethyl ether. The product thus precipitated was collected by filtration and was dried over sodium hydroxide under reduced pressure. The above-mentioned product was dissolved by adding 10 ml of DMF, then was neutralized with triethylamine under ice-cooling condition, then 639 mg of Boc-Gln-ONp ans 235 mg of HOBT were added thereto, and the pH of the mixture was keeping with N-methylmorpholine and stirred at room temperature for 18 hours. The reaction mixture was treated by adding 60 ml of water, and the precipitate thus formed was collected by filtration and dried, then washed with hot-ethyl acetate to obtain 2.02 g (yield: 96.5%) of the above-mentioned objective product.

Melting point: 185°–189° C.
Amino acid analysis:
Asp: 1.00 (1)
Thr: 2.91 (3)
Glu: 1.03 (1)
Gly: 2.01 (2)
Ala: 1.00 (1)
Val: 1.00 (1)
Arg: 1.01 (1)
Pro: 2.03 (2)

REFERENCE EXAMPLE 139

Preparation of
Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 1.97 g of Boc-Gln-Thr(Bzl)-Pro-Arg(Tos)-Thr(Bzl)-Asp(OcHex)-Val-Gly-Ala-Gly-Thr(Bzl)-Pro-NH$_2$ and 863 mg of Boc-Lys(Cl-Z)-Leu-OH, and the same procedure as in Reference Example 15 was repeated to obtain 2.31 g (yield: 95.7%) of the above-mentioned objective product.

Melting point: 177°–182° C.
Amino acid analysis:
Asp: 1.00 (1)
Thr: 2.96 (3)
Glu: 1.03 (1)
Gly: 2.03 (2)
Ala: 1.02 (1)
Val: 1.01 (1)
Leu: 0.99 (1)
Lys: 0.97 (1)
Arg: 0.98 (1)
Pro: 2.01 (2)

REFERENCE EXAMPLE 140

Preparation of
Boc-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 2.26 g of Boc-Lys(Cl-Z)-Leu-Gln-Thr(Bzl)-Pro-Arg(Tos)-Thr(Bzl)-Asp(OcHex)-Val-Gly-Ala-Gly-Thr(Bzl) -Pro-NH$_2$, 626 mg of Boc-His(Tos)-OH and HOSu in place of HOBT and the same procedure as in Reference Example 15 was repeated to obtain 2.55 g (yield: 99.7%) of the above-mentioned objective product.

Melting point: 168°–175° C.
Amino acid analysis:

Asp: 1.02 (1)
Thr: 2.93 (3)
Glu: 1.03 (1)
Gly: 2.00 (2)
Ala: 1.04 (1)
Val: 1.02 (1)
Leu: 0.98 (1)
Lys: 0.93 (1)
His: 1.02 (1)
Arg: 1.01 (1)
Pro: 2.02 (2)

REFERENCE EXAMPLE 141

Preparation of
Boc-Leu-His(Tos)-Lys(Cl-Z)-Leu-Glu-Thr(Bzl)-Pro-Arg(Tos)-Thr(Bzl)-Asp(OcHex)-Val-Gly-Ala-Gly-Thr(Bzl)-Pro-NH$_2$ By using 2.50 g of Boc-His(Tos)-Lys(Cl-Z)-Leu-Gln-Thr(Bzl)-Pro-Arg(Tos)-Thr(Bzl)-Asp(OcHex)-Val-Gly-Ala -Gly-Thr(Bzl)-Pro-NH$_2$ and 493 mg of Boc-Leu-OSu, and the same procedure as in Reference Example 18 was repeated to obtain 2.31 g (yield: 88.2%) of the above-mentioned objective product.

Melting point: 176°–178° C.
Amino acid analysis:
Asp: 1.04 (1)
Thr: 3.04 (3)
Glu: 1.07 (1)
Gly: 2.07 (2)
Ala: 1.02 (1)
Val: 1.04 (1)
Leu: 1.78 (2)
Lys: 0.95 (1)
His: 0.87 (1)
Arg: 1.05 (1)
Pro: 2.08 (2)

REFERENCE EXAMPLE 142

Preparation of
Boc-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 2.26 g of Boc-Leu-His(Tos)-Lys(Cl-Z)-Leu-Gln-Thr(Bzl)-Pro-Arg(Tos)-Thr(Bzl)-Asp(OcHex)-Val-Gly-Ala -Gly-Thr(Bzl)-Pro-NH$_2$ and 424 mg of Boc-Glu(OcHex)-OH, and the same procedure as in Reference Example 15 was repeated to obtain 2.33 g (yield: 95.7%) of the above-mentioned objective product.

Melting point: 174°–177° C.
Amino acid analysis:
Asp: 1.07 (1)
Tht: 3.11 (3)
Glu: 1.86 (2)
Gly: 2.08 (2)
Ala: 1.04 (1)
Val: 1.06 (1)
Leu: 1.81 (2)
Lys: 0.96 (1)
His: 0.87 (1)
Arg: 1.06 (1)
Pro: 2.07 (2)

REFERENCE EXAMPLE 143

Preparation of
Boc-Gln-Glu(OcHex)-Leu-His(Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 2.28 g of Boc-Glu(OcHex)-Leu-His(Tos)-Lys(Cl-Z)-Leu-Gln-Thr(Bzl)-Pro-Arg(Tos)-Thr(Bzl)-Asp(OcHex) -Val-Gly-Ala-Gly-Thr(Bzl)-Pro-NH$_2$ and 446 mg of Boc-Gln-ONp, and the same procedure as in Reference Example 18 was repeate repeated to obtain 2.19 g (yield: 91.4%) of the above-mentioned objective product.

Melting point: 178°–180° C.
Amino acid analysis:
Asp: 1.08 (1)
Thr: 3.14 (3)
Glu: 2.70 (3)
Gly: 2.10 (2)
Ala: 1.06 (1)
Val: 1.07 (1)
Leu: 1.83 (2)
Lys: 0.97 (1)
His: 0.87 (1)
Arg: 1.08 (1)
Pro: 2.09 (2)

REFERENCE EXAMPLE 144

Preparation of
Boc-Lys(Z)-Leu-Ser(Bzl)-Gln-Glu(OcHex)-Leu-His(-Tos)-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 1.14 g of Boc-Gln-Glu(OcHex)-Leu-His(-Tos)-Lys(Cl-Z)-Leu-Gln-Thr(Bzl)-Pro-Arg(Tos)-Thr(Bzl) -Asp(OcHex)-Val-Gly-Ala-Gly-Thr(Bzl)-Pro-NH$_2$ and 393 mg of Boc-Lys(Z)-Leu-Ser(Bzl)-OH, and the same procedure as in Reference Example 15 was repeated to obtain 1.30 g (yield: 95.0%) of the above-mentioned objective product.

Melting point: 189°–193° C.
Amino acid analysis:
Asp: 1.07 (1)
Thr: 3.09 (3)
Ser: 0.75 (1)
Glu: 2.73 (3)
Gly: 2.13 (2)
Ala: 1.10 (1)
Val: 1.05 (1)
Leu: 2.79 (3)
Lys: 1.92 (2)
His: 0.79 (1)
Arg: 1.03 (1)
Pro: 2.08 (2)

REFERENCE EXAMPLE 145

Preparation of
Boc-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH$_2$ By using 1.00 g of Boc-Gln-Thr(Bzl)-Pro-Arg(Tos)-Thr(Bzl)-Asp(OcHex)-Val-Gly-Ala-Gly-Thr(Bzl)-Pro-NH$_2$ and 427 mg of Boc-Asn-Lys(Cl-Z)-Leu-OH, and the same procedure as in Reference Example 15 to obtain 1.22 g (yield: 94.3%) of the above-mentioned objective product.

Melting point: 168°-173° C.

REFERENCE EXAMPLE 146

Preparation of
Boc-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH₂

By using 800 mg of Boc-Asn-Lys(Cl-Z)-Leu-Gln-Thr(Bzl)-Pro-Arg(Tos)-Thr(Bzl)-Asp(OcHex)-Val-Gly-Ala-Gly -Thr(Bzl)-Pro-NH₂ and 301 mg of Boc-Ser(Bzl)-Gln-Glu(OcHex)-Leu-OH, and the same procedure as in the Reference Example 15 was repeated to obtain 965 mg (yield: 95.0%) of the above-mentioned objective product.

Melting point: 236°-243° C. (decomposed).

REFERENCE EXAMPLE 147

Preparation of
Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos)-Thr(Bzl)-Asp(OcHex)-Val-Gly-Ala-Gly-Thr(Bzl)-Pro-NH₂

By using 850 mg of Boc-Ser(Bzl)-Gln-Glu(OcHex)-Leu-Asn-Lys(Cl-Z)-Leu-Gln-Thr(Bzl)-Pro-Arg(Tos)-Thr(Bzl) -Asp(OcHex)-Val-Gly-Ala-Gly-Thr(Bzl)-Pro-NH₂ and 197 mg of Boc-Lys(Cl-Z)-Leu-OH, and the same procedure as in Reference Example was repeated to obtain 871 mg (yield: 90.0%) of of the above-mentioned objective product.

Melting Point: 230°-245° C. (decomposed).
Amino acid analysis:
  Asp: 1.99 (2)
  Thr: 2.90 (3)
  Ser: 0.94 (1)
  Glu: 3.10 (3)
  Gly: 1.97 (2)
  Ala: 1.00 (1)
  Val: 1.00 (1)
  Leu: 3.10 (3)
  Lys: 2.03 (2)
  Arg: 0.96 (1)
  Pro: 2.02 (2)

REFERENCE EXAMPLE 148

Preparation of
Boc-Gln-Thr(Bzl)-Asp(OBzl)-Val-Gly-Ala-Gly-Thr(Bzl)-Pro-NH₂

By using 3.51 g of Boc-Thr(Bzl)-Asp(OBzl)-Val-Gly-Ala-Gly-Thr(Bzl)-Pro-NH₂ and 1.66 g of Boc-Gln-ONp, and the same procedure as in Reference Example 18 was repeated to obtain 3.41 g (yield: 87.9%) of the above-mentioned objective product.

Melting point: 192°-195° C.

REFERENCE EXAMPLE 149

Preparation of
Boc-Thr(Bzl)-Pro-Gln-Thr(Bzl)-Asp(OBzl)-Val-Gly-Ala-Gly-Thr(Bzl)-Pro-NH₂

By using 3.08 g of Boc-Gln-Thr(Bzl)-Asp(OBzl)-Val-Gly-Ala-Gly-Thr(Bzl)-Pro-NH₂ and 1.52 g of Boc-Thr(Bzl)-Pro-OH, and the same procedure as in Reference Example 15 was repeated to obtain 3.21 g (yield: 85.4%) of the above-mentioned objective product.

Melting point: 190°-193° C.

REFERENCE EXAMPLE 150

Preparation of
Boc-Gln-Thr(Bzl)-Pro-Gln-Thr(Bzl)-Asp(OBzl)-Val-Gly-Ala-Gly-Thr(Bzl)-Pro-NH₂

By using 3.15 g of Boc-Thr(Bzl)-Pro-Gln-Thr(Bzl)-Asp(OBzl)-Val-Gly-Ala-Gly-Thr(Bzl)-Pro-NH₂ and 1.16 g of Boc-Gln-ONp, and the same procedure as in Reference Example 18 was repeated to obtain 3.07 g (yield: 89.8%) of the above-mentioned objective product.

Melting point: 173°-178° C.

REFERENCE EXAMPLE 151

Preparation of
Boc-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH₂

By using 2.02 g of Boc-Gln-Thr(Bzl)-Pro-Gln-Thr(Bzl)-Asp(OBzl)-Val-Gly-Ala-Gly-Thr(Bzl)-Pro-NH₂ and 982 mg of Boc-Lys(Cl-Z)-Leu-OH, and the same procedure as in Reference Example 15 was repeated to obtain 2.41 g (yield: 95.3%) of the above-mentioned objective product.

Melting point: 204°-209° C.

REFERENCE EXAMPLE 152

Preparation of
Boc-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH₂

By using 2.36 g of Boc-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH₂ and 639 mg of Boc-Leu-His-OH as well as HOSu in place of HOBT, and the same procedure as in Reference Example 15 was repeated to obtain 2.46 g (yield: 91.3%) of the above-mentioned objective product.

Melting point: 209°-215° C. (decomposed).

REFERENCE EXAMPLE 153

Preparation of
Boc-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH₂

By using 1.82 g of Boc-Leu-His-Lys(Cl-Z)-Leu-Gln-Thr(Bzl)-Pro-Gln-Thr(Bzl)-Asp(OBzl)-Val-Gly-Ala-Gly -Thr(Bzl)-Pro-NH₂ and 498 mg of Boc-Glu(OcHex)-OSu, and the same procedure as in Reference Example 18 was repeated to obtain 1.87 g (yield: 95.9%) of the above-mentioned objective product.

Melting point: 209°-217° C. (decomposed).

REFERENCE EXAMPLE 154

Preparation of
Boc-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH₂

By using 1.87 g of Boc-Glu(OcHex)-Leu-His-Lys(Cl-Z)-Leu-Gln-Thr(Bzl)-Pro-Gln-Thr(Bzl)-Asp(OBzl)-Val -Gly-Ala-Gly-Thr(Bzl)-Pro-NH₂ and 404 mg of Boc-Gln-ONp, and the same procedure as in Reference Example 18 was repeated to obtain 1.77 g (yield: 90.3%) of the above-mentioned objective product.

Melting point: 200°-217° C.
Amino acid analysis:

Asp: 1.03 (1)
Thr: 2.96 (3)
Glu: 3.87 (4)
Gly: 2.02 (2)
Ala: 1.00 (1)
Val: 1.01 (1)
Leu: 2.06 (2)
Lys: 1.03 (1)
His: 0.94 (1)
Pro: 2.08 (2)

REFERENCE EXAMPLE 155

Preparation of
Boc-Lys(Cl-Z)-Leu-Ser(Bzl)-Gln-Glu(OcHex)-Leu-His-Lys(Cl-Z)-Leu-Gln-Thr(Bzl)-Pro-Gln-Thr(Bzl)-Asp(OBzl)-Val-Gly-Ala-Gly-Thr(Bzl)-Pro-NH$_2$ By using 501 mg of Boc-Gln-Glu(OcHex)-Leu-His-Lys(Cl-Z)-Leu-Gln-Thr(Bzl)-Pro-Gln-Thr(Bzl)-Asp(OBzl)-Val -Gly-Ala-Gly-Thr(Bzl)-Pro-NH$_2$ and 198 mg of Boc-Lys(Cl-Z)-Leu-Ser(Bzl)-OH, and the same procedure as in Reference Example 15 was repeated to obtain 554 mg (yield: 92.0%) of the above-mentioned objective product.

Melting point: 230°–241° C. (decomposed).
Amino acid analysis:
Asp: 1.02 (1)
Thr; 2.93 (3)
Ser: 0.78 (1)
Glu: 3.86 (4)
Gly: 2.01 (2)
Ala: 1.01 (1)
Val: 1.01 (1)
Leu: 3.08 (3)
Lys: 2.12 (2)
His: 0.89 (1)
Pro: 2.07 (2)

REFERENCE EXAMPLE 156

Boc-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro-NH$_2$

By using 2.55 g of Boc-Gln-Thr(Bzl)-Pro-Gln-Thr(Bzl)-Asp(OcHex)-Val-Gly-Ala-Gly-Thr(Bzl)-Pro-NH$_2$ and 1.21 g of Boc-Asn-Lys(Cl-Z)-Leu-OH, and the same procedure as in Reference Example 15 was repeated to obtain 2.75 g (yield: 81.5%) of the above-mentioned objective product.

Melting point: 207°–214° C.

REFERENCE EXAMPLE 157

Preparation of
Boc-Gln-Glu(OcHex)-Leu-Asn-Lys(Cl-Z)-Leu-Gln-Thr(Bzl)-Pro-Gln-Thr(Bzl)-Asp(OcHex) -Val-Gly-Ala-Gly-Thr(Bzl)-Pro-NH$_2$ By using 2.65 g of Boc-Asn-Lys(Cl-Z)-Leu-Gln-Thr(Bzl)-Pro-Gln-Thr(Bzl)-Asp(OcHex)-Val-Gly-Ala-Gly -Thr(Bzl)-Pro-NH$_2$ and 887 mg of Boc-Gln-Glu(OcHex)-Leu-OH, and the same procedure as in Reference Example 15 was repeated to obtain 3.09 g (yield: 96.6%) of the above-mentioned objective product.

Melting point: 224°–241° C. (decomposed).
Amino acid analysis:
Asp: 1.99 (2)
Thr: 2.90 (3)
Glu: 4.06 (4)
Gly: 1.99 (2)
Ala: 1.01 (1)
Val: 1.00 (1)
Leu: 2.04 (2)
Lys: 1.03 (1)
Pro: 1.98 (2)

REFERENCE EXAMPLE 158

Preparation of
Boc-Lys(Z)-Leu-Ser(Bzl)-Gln-Glu(OcHex)-Leu-Asn-Lys(Cl-Z)-Leu-Gln-Thr(Bzl)-Pro-Gln-Thr(Bzl)-Asp(OcHex)-Val-Gly-Ala-Gly-Thr(Bzl)-Pro-NH$_2$ By using 1.00 g of Boc-Gln-Glu(OcHex)-Leu-Asn-Lys(Cl-Z)-Leu-Gln-Thr(Bzl)-Pro-Gln-Thr(Bzl)-Asp(OcHex) -Val-Gly-Ala-Gly-Thr(Bzl)-Pro-NH$_2$ and 336 mg of Boc-Lys(Z)-Leu-Ser(Bzl)-OH, and the same procedure as in Reference Example 15 was repeated to obtain 1.08 g (yield: 88.0%) of the above-mentioned objective product.

Melting point: 235°–249° C. (decomposed).
Amino acid analysis:
Asp: 2.01 (2)
Thr: 2.93 (3)
Ser: 0.84 (1)
Glu: 4.08 (4)
Gly: 2.00 (2)
Ala: 1.00 (1)
Val: 1.01 (1)
Leu: 3.01 (3)
Lys: 2.03 (2)
Pro: 1.92 (2)

REFERENCE EXAMPLE 159

Preparation of
Boc-Thr(Bzl)-Tyr(Cl$_2$-Bzl)-Pro-Arg(Tos)-Thr(Bzl)-Asp(OcHex)-Val-Gly-Ala-Gly-Thr(Bzl) -Pro-NH$_2$ By using 9.00 g of Boc-Arg(Tos)-Thr(Bzl)-Asp(OcHex)-Val-Gly-Ala-Gly-Thr(Bzl)-Pro-NH$_2$ and 5.67 g of Boc-Thr(Bzl)-Tyr(Cl$_2$-Bzl)-Pro-OH, and the same procedure as in Reference Example 15 was repeated to obtain 12.28 g (yield: 94.7%) of the above-mentioned objective product.

Melting point: 195°–198° C.

REFERENCE EXAMPLE 160

Preparation of
Boc-Gln-Thr(Bzl)-Tyr(Cl$_2$-Bzl)-Pro-Arg(Tos)-Thr(Bzl)-Asp(OcHex)-val-Gly-Ala-Gly-Thr(Bzl)-Pro-NH$_2$ By using 12.00 g of Boc-Thr(Bzl)-Tyr(Cl$_2$-Bzl)-Pro-Arg(Tos)-Thr(Bzl)-Asp(OcHex)-Val-Gly-Ala-Gly-Thr(Bzl) -Pro-NH$_2$ and 2.65 g of Boc-Gln-ONp, and the same procedure as in Reference Example 18 was repeated to obtain 12.4 8 g (yield: 97.7%) of the above-mentioned objective product.

Melting point: 185°–187° C.

REFERENCE EXAMPLE 161

Preparation of
Boc-Lys(Cl-Z)-Gln-Thr(Bzl)-Tyr(Cl$_2$-Bzl)-Pro-Arg(Tos)-Thr(Bzl)-Asp(OcHex)-Val-Gly-Ala-Gly -Thr(Bzl)-Pro-NH$_2$ By using 12.25 g of Boc-Gln-Thr(Bzl)-Tyr(Cl$_2$-Bzl)-Pro-Arg(Tos)-Thr(Bzl)-Asp(OcHex)-Val-Gly-Ala-Gly -Thr(Bzl)-Pro-NH₂ and 3.54 g of Boc-Lys-OSu and the same procedure as in Reference Example 18 was repeated to obtain 13.01 g (yield: 93.2%) of the above-mentioned objective product.

Melting point: 179°–182° C.

REFERENCE EXAMPLE 162

Preparation of
Boc-His(Tos)-Lys(Cl-Z)-Gln-Thr(Bzl)-Tyr(Cl₂-Bzl)-Pro-Arg(Tos)-Thr(Bzl)-Asp(OcHex)-Val-Gly-Ala-Gly-Thr(Bzl)-Pro-NH₂

By using 12.80 g of Boc-Lys(Cl-Z)-Gln-Thr(Bzl)-Tyr(Cl₂-Bzl)-Pro-Arg(Tos)-Thr(Bzl)-Asp(OcHex)-Val-Gly-Ala-Gly-Thr(Bzl)-Pro-NH₂ and 3.24 g of Boc-His(Tos)-OH, as well as 910 mg of HOSu in place of HOBT, and the same procedure as in Reference Example 15 was repeated to obtain 13.05 g (yield: 91.0%) of the above-mentioned objective product.

Melting point: 171°–176° C.

REFERENCE EXAMPLE 163

Preparation of
Boc-Gln-Glu(OcHex)-Leu-His(Tos)-Lys(Cl-Z)-Gln-Thr(Bzl)-Tyr(Cl₂-Bzl)-Pro-Arg(Tos)-Thr(Bzl)-Asp(OcHex)-Val-Gly-ALa-Gly-Thr(Bzl)-Pro-NH₂

By using 12.85 g of Boc-His(Tos)-Lys(Cl-Z)-Gln-Thr(Bzl)-Tyr(Cl₂-Bzl)-Pro-Arg(Tos)-Thr(Bzl)-Asp(OcHex)-Val -Gly-Ala-Gly-Thr(Bzl)-Pro-NH₂ and 4.05 g of Boc-Gln-Glu (OcHex)-Leu-OH as well as 816 mg of HOSu in place of HOBT, and the same procedure as in Reference Example 15 was repeated to obtain 13.85 g (yield: 92.4%) of the above-mentioned objective product.

Melting point: 177°–180° C.

REFERENCE EXAMPLE 164

Preparation of
Boc-Lys(Cl-Z)-Leu-Ser(Bzl)-Gln-Glu(OcHex)-Leu-His(Tos)-Lys(Cl-Z)-Gln-Thr(Bzl)-Tyr(Cl₂-Bzl)-Pro-Arg(Tos)-Thr(Bzl)-Asp(OcHex)-Val-Gly-Ala-Gly-Thr(Bzl)-Pro-NH₂

By using 13.60 g of Boc-Gln-Glu(OcHex)-Leu-His(Tos)-Lys(Cl-Z)-Gln-Thr(Bzl)-Tyr(Cl₂-Bzl)-Pro-Arg(Tos) -Thr(Bzl)-Asp(OcHex)-Val-Gly-Ala-Gly-Thr(Bzl)-Pro-NH₂ and 3.63 g of Boc-Lys(Cl-Z)-Leu-Ser(Bzl)-OH as well as 592 mg of HOSu in place of HOBT, and the same procedure as in Reference Example 15 was repeated to obtain 14.87 g (yield: 92.3%) of the above-mentioned objective product.

Melting point: 190°–195° C.

REFERENCE EXAMPLE 165

Preparation of Boc-Ser(Bzl)-Leu-OEt

By using 7.37 g of Boc-Ser(Bzl)-OH and 5.00 g of H-Leu-OEt, and the same procedure as in Reference Example 15 was repeated to obtain 7.53 g (yield: 69.1%) of the above-mentioned objective product.

Appearance: Oily substance.

REFERENCE EXAMPLE 166

Preparation of Boc-Ala-Ser(Bzl)-Leu-OEt

By using 7.53 g of Boc-Ser(Bzl)-Leu-OEt and 3.50 g of Boc-Ala-OH, and the same procedure as in Reference Example 15 was repeated to obtain 7.26 g (yield: 82.9%) of the above-mentioned objective product.

Melting point: 97°–97.5° C.

REFERENCE EXAMPLE 167

Preparation of Boc-Gly-Ala-Ser(Bzl)-Leu-OEt

By using 3.50 g of Boc-Ala-Ser(Bzl)-Leu-OEt and 1.30 g of Boc-Gly-OH, and the same procedure as in Reference Example 15 was repeated to obtain 3.03 g (yield: 77.8%) of the above-mentioned objective product.

Melting point: 134°–135° C.

REFERENCE EXAMPLE 168

Preparation of Boc-Gly-Ala-Ser(Bzl)-Leu-NHNH₂

By using 3.00 g of Boc-Gly-Ala-Ser(Bzl)-Leu-OEt, and the same procedure as in Reference Example 6 was repeated to obtain 2.61 g (yield: 89.2%) of the above-mentioned objective product.

Melting point: 195°–197° C.

REFERENCE EXAMPLE 169

Preparation of
Boc-Gly-Ala-Ser(Bzl)-Leu-Ser(Bzl)-Thr(Bzl)-Glu-OBzl

By using 2.56 g of Boc-Ser(Bzl)-Thr(Bzl)-Glu-OBzl and 2.00 g of Boc-Gly-Ala-Ser(Bzl)-Leu-NHNH₂, and the same procedure as in Reference Example 7 was repeated to obtain 3.13 g (yield: 76.8%) of the above-mentioned objective product.

Melting point: 209°–212° C.

REFERENCE EXAMPLE 170

Preparation of ⌐Gly—Ala—Ser(Bzl)—Leu—Ser(Bzl)—Thr(Bzl)—Glu—OBzl⌐

By using 3.10 g of Boc-Gly-Ala-Ser(Bzl)-Leu-Ser(Bzl)-Thr(Bzl)-Glu-OBzl and the same procedure as in Reference Example 8 was repeated to obtain 2.17 g (yield: 78.2%) of the above-mentioned objective product.

Melting point: 150°–154° C.

REFERENCE EXAMPLE 171

Preparation of ⌐Gly—Ala—Ser(Bzl)—Leu—Ser(Bzl)—Thr(Bzl)—Glu—NHNH₂⌐

By using 2.10 g of

⌐Gly—Ala—Ser(Bzl)—Leu—Ser(Bzl)—Thr(Bzl)—Glu—OBzl, and the same procedure as in Reference Example 9 was repeated to obtain 1.90 g (yield: 97.9%) of the above-mentioned objective product.

Melting point: 124°–130° C.

REFERENCE EXAMPLE 172

Preparation of ⌐Gly—Ala—Ser(Bzl)—Leu—Ser(Bzl)—Thr(Bzl)—Glu—Val—Leu—Gly—OH

By using 1.80 g of

⌐Gly—Ala—Ser(Bzl)—Leu—Ser(Bzl)—Thr(Bzl)—Glu—NHNH$_2$ and 1.20 g of Boc-Val-Leu-Gly-OH and the same procedure as in Reference Example 13 was repeated to obtain 1.90 g (yield: 84.0%) of the above-mentioned objective product.

Melting point: 217°–220° C.

EXAMPLE 1

Preparation of ⌐Gly—Ser—Asn—Leu—Ser—Thr—Glu—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—Pro—NH$_2$ 150 Milligrams of Boc-Lys(Cl-Z)-Leu-Ser(Bzl)-Gln-Glu(OcHex)-Leu-His(Tos)-Lys(Cl-Z)-Leu-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ was dissolved by adding 2 ml of TFA, then this solution was allowed to stand for 40 minutes at room temperature. This reaction mixture was concentrated under reduced pressure, to the residue thus obtained was added diethyl ether, and the precipitate formed was collected by filtration, and dried over sodium hydroxide under reduced pressure. The dried residue was dissolved in 2 ml of DMF and this solution was neutralized with triethylamine under ice-cooling condition. Next, to this mixture was added 56 mg of ⌐Gly—Ser(Bzl)—Asn—Leu—Ser(Bzl)—Thr(Bzl)—Glu—Val—Leu—Gly—OH, 6 mg of HOBT and 0.010 ml of WSC, then the pH of the mixture was adjusted to pH 7, the whole mixture was stirred under ice-cooling condition for 1 hour, further stirred at room temperature for 18 hours. 50 Milliliters of water was added to the reaction mixture, the precipitate formed was collected by filtration, dried, and washed with 20 ml of hot-ethyl acetate to obtain 180 mg of the protected peptide as a crude product.

150 Milligrams of this protected peptide crude product was stirred with a mixture of 15 ml of hydrogen fluoride and 1.5 ml of anisole under ice-cooling condition for 60 minutes. Then the hydrogen fluoride was removed by evaporation under reduced pressure under ice-cooling condition, the residue thus obtained was washed with diethyl ether, then dissolved in 10 ml of 1M-acetic acid, next lyophilized to obtain 86 mg of powdery substance.

Among this powdery substance, 50 mg thereof was purified and determined by means of a high-performance liquid chromatography under the following conditions, there was obtained 11.6 mg of the active powder of the objective product.

Column: ODS-120T (21.5 mm I.D. × 30 cm, manufactured by Tosoh Corp., Tokyo, Japan)

Method of elution: Linear-type concentration gradient elution (40 minutes)

Eluent: 0.1% TFA aqueous solution: 90% acetonitrile/0.1% TFA aqueous solution (80:20)→(30:70)

Velocity: 15 ml/minute

Detection: at UV 210 nm

Amino acid analysis:
 Asp: 2.00 (2)
 Thr: 4.76 (5)
 Ser: 3.62 (4)
 Glu: 4.10 (4)
 Gly: 3.98 (4)
 Val: 1.01 (1)
 Leu: 5.06 (5)
 Tyr: 0.98 (1)
 Lys: 1.99 (2)
 His: 1.02 (1)
 Arg: 1.02 (1)
 Pro: 2.07 (2)

EXAMPLE 2

Preparation of ⌐Gly—Ser—Asn—Leu—Ser—Thr—Glu—Val—Leu—Gly—Lys—Leu—Ser—Gln—Glu—Leu—His—Lys—Gln—Thr—Tyr—Pro—Arg—Thr—Asn—Thr—Gly—Ser—Gly—Thr—Pro—NH$_2$ By using 150 mg of Boc-Lys(Cl-Z)-Leu-Ser(Bzl)-Gln-Glu(OcHex)-Leu-His(Tos)-Lys(Cl-Z)-Gln-Thr(Bzl)-Tyr(Cl$_2$-Bzl)-Pro-Arg(Tos)-Thr(Bzl)-Asn-Thr(Bzl)-Gly-Ser(Bzl)-Gly-Thr(Bzl)-Pro-NH$_2$ and 57 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 170 mg of the protected peptide crude product. Among the crude product of protected peptide, 150 mg thereof was treated with hydrogen fluoride and anisole as in Example 1 to obtain 100 mg of powdery substance.

Among this powdery substance, 50 mg thereof was purified and determined by means of a high-performance liquid chromatography under the same condition as in Example 1, there was obtained 8.7 mg of the active powder of the above-mentioned objective product.

Amino acid analysis:
Asp: 2.00 (2)
Thr: 4.82 (5)
Ser: 3.67 (4)
Glu: 4.13 (4)
Gly: 3.98 (4)
Leu: 4.04 (4)
Tyr: 0.98 (1)
Lys: 1.98 (2)
His: 1.01 (1)
Arg: 1.01 (1)
Pro: 2.06 (2)
Val: 0.99 (1)

EXAMPLE 3

Preparation of ⌐Gly—Ser—Asn—Leu—Ser—Thr—Glu—Val—
Leu—Gly—Lys—Leu—Ser—Gln—Glu—Leu—His—Lys—Leu—Gln—Thr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 60 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 180 mg of the protected peptide as a crude product.

Among the protected peptide crude product, 150 mg thereof was treated with hydrogen fluoride and anisole as in Example 1 to obtain 110 mg of powdery substance.

Among this powdery substance, 50 mg thereof was purified and determined by means of a high-performance liquid chromatography under the same condition as in Example 1, there was obtained 25.5 mg of the active powder of the above-mentioned objective product.

Amino acid analysis:
Asp: 2.01 (2)
Thr: 4.77 (5)
Ser: 3.64 (4)
Glu: 4.07 (4)
Gly: 3.98 (4)
Val: 1.01 (1)
Leu: 5.09 (5)
Lys: 2.01 (2)
His: 0.99 (1)
Arg: 0.99 (1)
Pro: 2.09 (2)

EXAMPLE 4

Preparation of ⌐Gly—Ser—Asn—Leu—Ser—Thr—Glu—
Val—Leu—Gly—Lys—Leu—Ser—Gln—Glu—Leu—Asn—Lys—Leu—Gln—Thr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Asn-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 63 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 190 mg of the protected peptide as a crude product.

Among the protected peptide as a crude product, 150 mg thereof was treated with hydrogen fluoride and anisole as in Example 1 to obtain 102 mg of powdery substance.

Among this powdery substance, 50 mg thereof was purified and determined by means of a high-performance liquid chromatography under the same condition as in Example 1, there was obtained 17.7 mg of active powder of the objective product.

Amino acid analysis:
Asp: 2.97 (3)
Thr: 4.75 (5)
Ser: 3.68 (4)
Glu: 4.13 (4)
Gly: 4.04 (4)
Val: 0.99 (1)
Leu: 5.09 (5)
Lys: 1.99 (2)
Arg: 1.00 (1)
Pro: 2.04 (2)

EXAMPLE 5

Preparation of ⌐Acp—Asn—Leu—Ser—Thr—Asp—Val—
Leu—Gly—Lys—Leu—Ser—Gln—Glu—Leu—His—Lys—Leu—Gln—Thr—Tyr—
Pro—Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl) -Tyr(Cl₂-Bzl)-Pro-Arg(Tos)-Thr(Bzl)-Asn-Thr(Bzl)-Gly-Ser(Bzl)-Gly-Thr(Bzl)-Pro-NH₂ and 50 mg of

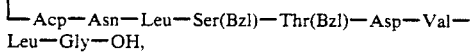
―Acp―Asn―Leu―Ser(Bzl)―Thr(Bzl)―Asp―Val―Leu―Gly―OH, and the same procedure as in Example 1 was repeated to obtain 170 mg of the protected peptide as a crude product.

Among this crude product of the protected peptide, 160 mg thereof was treated with hydrogen fluoride and anisole as in Example 1 to obtain 100 mg of powdery substance.

Among this powdery substance, 50 mg thereof was purified and determined by means of a high-performance liquid chromatography under the same condition as in Example 1 and obtained 8.5 mg of active powder of the above-mentioned objective product.

Amino acid analysis:
Asp: 2.83 (3)
Thr: 4.77 (5)
Ser: 2.81 (3)
Glu: 3.10 (3)
Gly: 3.02 (3)
Val: 0.98 (1)
Leu: 5.03 (5)
Tyr: 0.98 (1)
Lys: 1.99 (2)
His: 1.00 (1)
Arg: 0.99 (1)
Pro: 2.12 (2)
Acp: 0.88 (1)

EXAMPLE 6

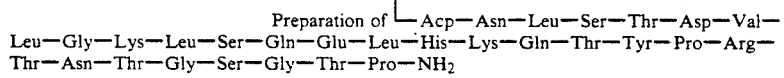
Preparation of ―Acp―Asn―Leu―Ser―Thr―Asp―Val―Leu―Gly―Lys―Leu―Ser―Gln―Glu―Leu―His―Lys―Gln―Thr―Tyr―Pro―Arg―Thr―Asn―Thr―Gly―Ser―Gly―Thr―Pro―NH₂

By using 150 mg of Boc-Lys(Cl-Z)-Leu-Ser(Bzl)-Gln-Glu(OcHex)-Leu-His(Tos)-Lys(Cl-Z)-Gln-Thr(Bzl)-Tyr(Cl₂-Bzl)-Pro-Arg(Tos)-Thr(Bzl)-Asn-Thr(Bzl)-Gly-Ser(Bzl)-Gly-Thr(Bzl)-Pro-NH₂ and 51 mg of

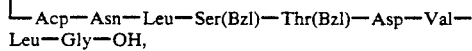
―Acp―Asn―Leu―Ser(Bzl)―Thr(Bzl)―Asp―Val―Leu―Gly―OH, and the same procedure as in Example 1 was repeated to obtain 170 mg of the protected peptide as a crude product.

Among this crude product of the protected peptide, 150 mg thereof was treated with hydrogen fluoride and anisole as in Example 1 to obtain 80 mg of powdery substance.

Among this powdery substance, 50 mg thereof was purified and determined by means of a high-performance liquid chromatography under the same condition as in Example 1 and obtained 7.7 mg of active powder of the above-mentioned objective product.

Amino acid analysis:
Asp: 2.78 (3)
Thr: 4.84 (5)
Ser: 2.81 (3)
Glu: 3.09 (3)
Gly: 3.00 (3)
Val: 0.97 (1)
Leu: 4.03 (4)
Tyr: 0.97 (1)
Lys: 1.98 (2)
His: 1.01 (1)
Arg: 1.01 (1)
Pro: 2.09 (2)
Acp: 0.81 (1)

EXAMPLE 7

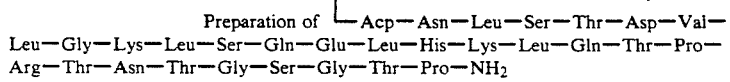
Preparation of ―Acp―Asn―Leu―Ser―Thr―Asp―Val―Leu―Gly―Lys―Leu―Ser―Gln―Glu―Leu―His―Lys―Leu―Gln―Thr―Pro―Arg―Thr―Asn―Thr―Gly―Ser―Gly―Thr―Pro―NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 54 mg of

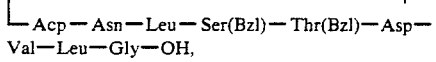
―Acp―Asn―Leu―Ser(Bzl)―Thr(Bzl)―Asp―Val―Leu―Gly―OH, and the same procedure as in Example 1 was repeated to obtain 160 mg of the protected peptide as a crude product.

160 Milligrams of this protected peptide crude product was treated with hydrogen fluoride and anisole as in Example 1 to obtain 104 mg of powdery substance.

Among this powdery substance, 50 mg thereof was purified and determined by means of a high-performance liquid chromatography under the same condition as in Example 1 and obtained 15.1 mg of active powder of the above-mentioned objective product.

Amino acid analysis:
Asp: 2.79 (3)
Thr: 4.84 (5)
Ser: 2.82 (3)
Glu: 3.03 (3)
Gly: 3.02 (3)
Val: 1.00 (1)
Leu: 5.15 (5)
Lys: 2.04 (2)
His: 0.98 (1)
Arg: 0.99 (1)
Pro: 1.94 (2)
Acp: 0.82 (1)

EXAMPLE 8

Preparation of ⌐Gly—Ser—Asn—Leu—Ser—Thr—Glu—Val—
Leu—Gly—Lys—Leu—Ser—Gln—Glu—Leu—His—Lys—Leu—Gln—Thr—Pro—Gln—
Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Gln-Thr(Bzl)-Asn-Thr(Bzl)-Gly-Ser(Bzl)-Gly-Thr(Bzl)-Pro-NH₂ and 63 mg of ⌐Gly—Ser(Bzl)—Asn—Leu—Ser(Bzl)—Thr(Bzl)—Glu—
Val—Leu—Gly—OH, and the same procedure as in Example 1 was repeated to obtain 180 mg of the protected peptide as a crude product.

150 Milligrams of this protected peptide crude product was treated with hydrogen fluoride and anisole as in Example 1 to obtain 100 mg of powdery substance.

Among the powdery substance, 50 mg thereof was purified and determined by means of a high-performance liquid chromatography under the same condition as in Example 1 and obtained 19.3 mg of active powder of the above-mentioned objective product.

Amino acid analysis:
Asp: 2.01 (2)
Thr: 4.89 (5)
Ser: 3.77 (4)
Glu: 5.14 (5)
Gly: 3.96 (4)
Val: 0.94 (1)
Leu: 5.03 (5)
Lys: 2.02 (2)
His: 0.99 (1)
Pro: 2.03 (2)

EXAMPLE 9

Preparation of ⌐Gly—Ser—Asn—Leu—Ser—Thr—Glu—Val—
Leu—Gly—Lys—Leu—Ser—Gln—Glu—Leu—Asn—Lys—Leu—Gln—Thr—Pro—
Gln—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Asn-Lys(Cl-Z)-Leu-Gln-Thr(Bzl)-Pro-Gln -Thr(Bzl)-Asn-Thr(Bzl)-Gly-Ser(Bzl)-Gly-Thr(Bzl)-Pro-NH₂ and 66 mg of ⌐Gly—Ser(Bzl)—Asn—Leu—Ser(Bzl)—Thr(Bzl)—Glu—
Val—Leu—Gly—OH, the same procedure as in Example 1 was repeated to obtain 190 mg of the protected peptide as a crude product.

150 Milligrams of this protected peptide crude product was treated with hydrogen fluoride and anisole as in Example 1 to obtain 104 mg of powdery substance.

Among this powdery substance, 50 mg thereof was purified and determined by means of a high-performance liquid chromatography under the same condition as in Example 1, and obtained 13.4 mg of active powder of the above- o mentioned objective product.

Amino acid analysis:
Asp: 3.03 (3)
Thr: 4.83 (5)
Ser: 3.72 (4)
Glu: 5.10 (5)
Gly: 3.93 (4)
Val: 0.95 (1)
Leu: 5.08 (5)
Lys: 2.06 (2)
Pro: 2.02 (2)

EXAMPLE 10

Preparation of ⌐Gly—Ser—Asn—Leu—Ser—Thr—Glu—Val—
Leu—Gly—Lys—Leu—Ser—Gln—Glu—Leu—Gly—Lys—Leu—Gln—Thr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Gly-Lys(Cl-Z)-Leu-Gln-Thr(Bzl)-Pro-Arg(Tos) -Thr(Bzl)-Asn-Thr(Bzl)-Gly-Ser(Bzl)-Gly-Thr(Bzl)-Pro-NH₂ and 65 mg of ⌐Gly—Ser(Bzl)—Asn—Leu—Ser(Bzl)—Thr(Bzl)—Glu—
Val—Leu—Gly—OH, the same procedure as in Example 1 was repeated to obtain 180 mg of the protected peptide as a crude product.

150 Milligrams of this protected peptide crude product was treated with hydrogen fluoride and anisole as in Example 1 to obtain 74 mg of powdery substance.

Among this powdery substance, 50 mg thereof was purified and determined by means of a high-performance liquid chromatography under the same condition as in Example 1, there was obtained 14.9 mg of active powder of the above-mentioned objective product.

Amino acid analysis:
Asp: 2.01 (2)
Thr: 4.86 (5)
Ser: 3.78 (4)
Glu: 4.12 (4)
Gly: 4.97 (5)
Val: 0.93 (1)

Leu: 5.10 (5)
Lys: 2.02 (2)
Arg: 0.98 (1)
Pro: 1.94 (2)

EXAMPLE 11

Preparation of ⌐β-Ala—Ser—Asn—Leu—Ser—Thr—Asp—Val—
Leu—Gly—Lys—Leu—Ser—Gln—Glu—Leu—His—Lys—Leu—Gln—Thr—Pro—Gln—
Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro-Gln -Thr(Bzl)-Asn-Thr,(Bzl)-Gly-Ser(Bzl)-Gly-Thr(Bzl)-Pro-NH₂ and 63.4 mg of ⌐β-Ala—Ser(Bzl)—Asn—Leu—Ser(Bzl)—Thr(Bzl)—Asp—
Val—Leu—Gly—OH, the same procedure as in Example was repeated to obtain 170 mg of the protected peptide as a crude product.

150 Milligrams of this protected peptide crude product was treated with hydrogen fluoride and anisole as in Example 1 to obtain 105 mg of powdery substance.

Among this powdery substance, 30 mg thereof was purified and determined by means of a high-performance liquid chromatography under the same condition as in Example 1, there was obtained 11.2 mg of active powder of the above-mentioned objective product.

Amino acid analysis:
Asp: 2.99 (3)
Thr: 4.86 (5)
Ser: 3.78 (4)
Glu: 4.11 (4)
Gly: 3.01 (3)
Val: 0.97 (1)
Leu: 4.99 (5)
Lys: 2.02 (2)
His: 1.00 (1)
Pro: 2.06 (2)
β-Ala: 1.00 (1)

EXAMPLE 12

Preparation of ⌐Ser—Asn—Leu—Ser—Thr—Cpc—Val—Leu—
Gly—Lys—Leu—Ser—Gln—Glu—Leu—His—Lys—Leu—Gln—Thr—Pro—Arg—
Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Arg(Tos)-Thr(Bzl)-Asn-Thr,(Bzl)-Gly-Ser(Bzl)-Gly-Thr(Bzl)-Pro-NH₂ and 60.6 mg of ⌐Ser(Bzl)—Asn—Leu—Ser(Bzl)—Thr(Bzl)—Cpc—
Val—Leu—Gly—OH, the same procedure as in Example 1 was repeated to obtain 170 mg of the protected peptide as a crude product.

150 Milligrams of this protected peptide crude product was treated with hydrogen fluoride and anisole as in Example 1, to obtain 98 mg of powdery substance.

Among this powdery substance, 30 mg thereof was purified and determined by means of a high-performance liquid chromatography under the same condition as in Example 1, there was obtained 9.6 mg of active powder of the above-mentioned objective product.

Amino acid analysis:
Asp: 2.04 (2)
Thr: 4.92 (5)
Ser: 3.85 (4)
Glu: 3.13 (3)
Gly: 3.04 (3)
Val: 0.97 (1)
Leu: 5.05 (5)
Lys: 1.97 (2)
His: 1.01 (1)
Arg: 1.01 (1)
Pro: 2.01 (2)
Cpc: 0.71 (1)

EXAMPLE 13

Preparation of ⌐Abu—Asn—Leu—Ser—Thr—Cec—Val—Leu—
Gly—Lys—Leu—Ser—Gln—Glu—Leu—His—Lys—Leu—Gln—Thr—Pro—Arg—
Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 55.4 mg of ⌐Abu—Asn—Leu—Ser(Bzl)—Thr(Bzl)—Cec—
Val—Leu—Gly—OH, the same procedure as in Example 1 was repeated to obtain 150 mg of the protected peptide as a crude product.

150 Milligrams of this protected peptide crude product was treated with hydrogen fluoride and anisole as in Example 1 to obtaine 100 mg of powdery substance.

Among this powdery substance, 30 mg thereof was purified and determined by means of a high-performance liquid chromatography under the same condition as in Example 1, there was obtained 10.5 mg of active powder of the above-mentioned objective product.

Amino acid analysis:
Asp: 2.02 (2)
Thr: 4.85 (5)
Ser: 2.78 (3)
Gly: 3.02 (3)
Val: 0.99 (1)
Leu: 5.05 (5)
Lys: 2.04 (2)
His: 1.00 (1)
Arg: 1.00 (1)
Pro: 2.04 (2)
Abu: 1.22 (1)

Cec and Glu could not determined, because the peaks being indicated thereby were overlapped.

EXAMPLE 14

Preparation of ⌐—CH₂CO—Ser—Asn—Leu—Ser—Thr—Tyr—Val—Leu—Gly—Lys—Leu—Ser—Gln—Glu—Leu—Asn—Lys—Leu—Gln—Thr—Pro—Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos) -Thr(Bzl)-Asn-Thr(Bzl)-Gly-Ser(Bzl)-Gly-Thr(Bzl)-Pro-NH₂ and 65.2 mg of ⌐—CH₂CO—Ser(Bzl)—Asn—Leu—Ser(Bzl)—Thr(Bzl)—Tyr—Val—Leu—Gyl—OH, and the same procedure as in Example 1 was repeated to obtain 170 mg of the protected peptide as a crude product.

150 Milligrams of this protected peptide crude product was treated with hydrogen fluoride and anisole as in Example 1 to obtain 94 mg of powdery substance.

Among this powdery substance, 30 mg thereof was purified and determined by means of a high-performance liquid chromatography under the same condition as in Example 1, there was obtained 8.1 mg of active powder of the above-mentioned objective product.

Amino acid analysis:
Asp: 3.02 (3)
Thr: 4.86 (5)
Ser: 3.83 (4)
Glu: 3.15 (3)
Gly: 3.03 (3)
Leu: 5.05 (5)
Lys: 2.05 (2)
Arg: 1.00 (1)
Pro: 2.00 (2)

Val and Tyr(CH2COOH) could not be determined, because the peaks being indicated thereby were overlapped.

EXAMPLE 15

Preparation of ⌐—COCH₂CH₂CO—Asn—Leu—Ser—Thr—Lys—Val—Leu—Gly—Lys—Leu—Ser—Gln—Glu—Leu—Asn—Lys—Leu—Gln—Thr—Pro—Gln—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Asn-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 59.0 mg of ⌐—COCH₂CH₂CO—Asn—Leu—Ser(Bzl)—Thr(Bzl)—Lys—Val—Leu—Gly—OH, and the same procedure as in Example 1 was repeated to obtain 160 mg of the protected peptide as a crude product.

150 Milligrams of this protected pepetide crude product was treated with hydrogen fluoride and anisole as in Example 1 to obtain 96 mg of powdery substance.

Among this powdery substance, 30 mg thereof was purified and determined by means of a high-performance liquid chromatography under the same condition as in Example 1, there was obtained 7.2 mg of active powder of the above-mentioned objective product.

Amino acid analysis:
Asp: 3.02 (3)
Thr: 4.83 (5)
Ser: 2.82 (3)
Glu: 4.13 (4)
Gly: 3.02 (3)
Val: 1.01 (1)
Leu: 5.07 (5)
Lys: 2.87 (3)
Pro: 2.06 (2)

EXAMPLE 16

Preparation of ⌐—Gly—Ser—Asn—Leu—Ser—Thr—Glu—Gly—Leu—Gly—Lys—Leu—Ser—Gln—Glu—Leu—Gly—Lys—Leu—Gln—Thr—Pro—Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Gly-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 62.6 mg of

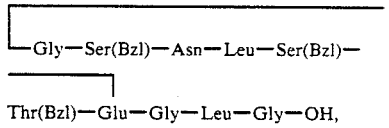
Thr(Bzl)—Glu—Gly—Leu—Gly—OH, and the same procedure as in Example 1 was repeated to obtain 160 mg of the protected peptide as a crude product.

150 Milligrams of this protected peptide crude product was treated with hydrogen fluoride and anisole as in Example 1 to obtain 81 mg of powdery substance.

Among this powdery substance, 30 mg thereof was purified and determined by means of a high-performance liquid chromatography under the same condition as in Example 1, there was obtained 4.7 mg of active powder of the above-mentioned objective product.

Amino acid analysis:
Asp: 2.01 (2)
Thr: 4.84 (5)
Ser: 3.77 (4)
Glu: 4.12 (4)
Gly: 5.96 (6)
Leu: 5.02 (5)
Lys: 2.04 (2)
Arg: 0.99 (1)
Pro: 2.02 (2)

EXAMPLE 17

Preparation of ⌐Gly—Ser—Asn—Leu—Ser—Thr—Glu—Ile—Leu—Gly—Lys—Leu—Ser—Gln—Glu—Leu—Gly—Lys—Leu—Gln—Thr—Pro—Arg—Thr—Asn—Thr—Gly—Ser—Gly—Thr—Pro—NH$_2$ By using 150 mg of Boc-Lys(Cl-Z)-Leu-Ser(Bzl)-Gln-Glu(OcHex)-Leu-Gly-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH$_2$ and 65.6 mg of

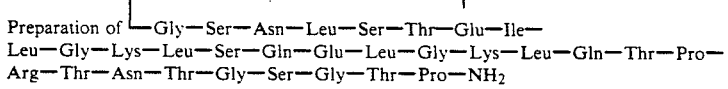
Thr(Bzl)—Glu—Ile—Leu—Gly—OH, the same procedure as in Example 1 was repeated to obtain 160 mg of the protected peptide as a crude product.

150 Milligrams of this protected peptide crude product was treated with hydrogen fluoride and anisole as in Example 1 to obtain 93 mg of powdery substance.

Among this powdery substance, 30 mg thereof was purified and determined by means of a high-performance liquid chromatography under the same condition as in Example 1, there was obtained 5.9 mg of active powder of the above-mentioned objective product.

Amino acid analysis:
Asp: 2.03 (2)
Thr: 4.80 (5)
Ser: 3.78 (4)
Glu: 4.13 (4)
Gly: 4.99 (5)
Ile: 1.00 (1)
Leu: 5.06 (5)
Lys: 2.03 (2)
Arg: 0.96 (1)
Pro: 1.99 (2)

EXAMPLE 18

Preparation of 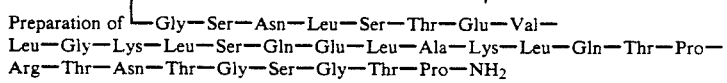
Leu—Gly—Lys—Leu—Ser—Gln—Glu—Leu—Ala—Lys—Leu—Gln—Thr—Pro—Arg—Thr—Asn—Thr—Gly—Ser—Gly—Thr—Pro—NH$_2$ By using 150 mg of Boc-Lys(Cl-Z)-Leu-Ser(Bzl)-Gln-Glu(OcHex)-Leu-Ala-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH$_2$ and 72.2 mg of

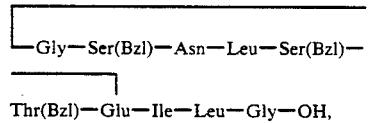
Thr(Bzl)—Glu—Val—Leu—Gly—OH, and the same procedure as in Example 1 was repeated to obtain 192 mg of the protected peptide as a crude product.

190 Milligrams of this protected peptide crude product was treated with hydrogen fluoride and anisole, as in Example 1 to obtain 138 mg of powdery product.

Among this powdery substance, 50 mg thereof was purified and determined by means of a high-performance liquid chromatography under the same condition as in Example 1, there was obtained 6.1 mg of active powder of the above-mentioned objective product.

Amino acid analysis:
Asp: 2.00 (2)
Thr: 4.71 (5)
Ser: 3.69 (4)
Glu: 4.12 (4)
Gly: 3.92 (4)
Ala: 0.99 (1)
Val: 1.00 (1)
Leu: 4.96 (5)
Lys: 2.04 (2)
Arg: 0.99 (1)
Pro: 1.97 (2)

EXAMPLE 19

Preparation of 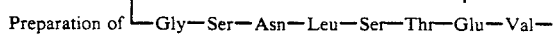

Leu—Gly—Lys—Leu—Ser—Gln—Glu—Leu—Ser—Lys—Leu—Gln—Thr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Ser(Bzl)-Lys(Cl-Z)-Leu-Gln-Thr(Bzl) -Pro-Arg(Tos)-Thr(Bzl)-Asn-Thr(Bzl)-Gly-Ser(Bzl)-Gly-Thr(Bzl)-Pro-NH₂ and 70.8 mg of

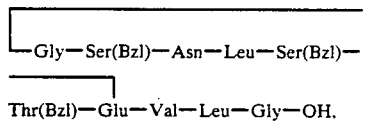

Thr(Bzl)—Glu—Val—Leu—Gly—OH.

the same procedure as in Example 1 was repeated to obtain 196 mg of the protected peptide as a crude product.

190 Milligrams of this protected peptide crude product was treated with hydrogen fluoride and anisole as in Example 1 to obtain 124 mg of powdery substance.

Among this powdery substance, 30 mg thereof was purified and determined by means of a high-performance liquid chromatography under the same condition as in Example 1, there was obtained 7.3 mg of active powder of the above-mentioned objective product.

Amino acid analysis:
Asp: 2.10 (2)
Thr: 4.82 (5)
Ser: 4.60 (5)
Glu: 4.11 (4)
Gly: 3.98 (4)
Val: 1.05 (1)
Leu: 4.93 (5)
Lys: 2.03 (2)
Arg: 1.02 (1)
Pro: 2.05 (2)

EXAMPLE 20

Preparation of ⌐Gly—Ser—Asn—Leu—Ser—Thr—Glu—Val—
Leu—Gly—Lys—Leu—Ser—Gln—Glu—Leu—Leu—Lys—Leu—Gln—Thr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Leu-Lys(Cl-Z)-Leu-Gln-Thr(Bzl)-Pro-Arg(Tos) -Thr(Bzl)-Asn-Thr(Bzl)-Gly-Ser(Bzl)-Gly-Thr(Bzl)-Pro-NH₂ and 72.2 mg of

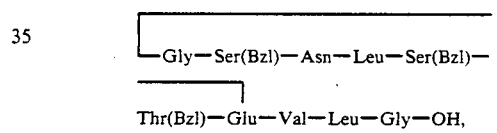

and the same procedure as in Example 1 was repeated to obtain 189 mg of the protected peptide as a crude product.

150 Milligrams of this protected peptide crude product was treated with hydrogen fluoride and anisole as in Example 1 to obtain 101 mg of powdery substance.

Among this powdery substance, 30 mg thereof was purified and determined by means of a high-performance liquid chromatography under the same condition as in Example 1, there was obtained 4.9 mg of active powder of the above-mentioned objective product.

Amino acid analysis:
Asp: 2.00 (2)
Thr: 4.84 (5)
Ser: 3,70 (4)
Glu: 4.13 (4)
Gly: 3.94 (4)
Val: 0.97 (1)
Leu: 6.00 (6)
Lys: 2.04 (2)
Arg: 1.03 (1)
Pro: 2.05 (2)

EXAMPLE 21

Preparation of 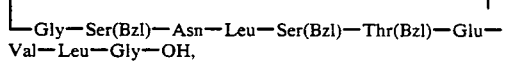—Gly—Ser—Asn—Leu—Ser—Thr—Glu—Val—
Leu—Gly—Lys—Leu—Ser—Gln—Glu—Leu—Gln—Lys—Leu—Gln—THr—Pro—
Arg—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Gln-Lys(Cl-Z)-Leu-Gln-Thr(Bzl)-Pro -Arg(Tos)-Thr(Bzl)-Asn-Thr(Bzl)-Gly-Ser(Bzl)-Gly-Thr(Bzl)-Pro-NH₂ and 72.2 mg of ⌐Gly—Ser(Bzl)—Asn—Leu—Ser(Bzl)—
Thr(Bzl)—Glu—Val—Leu—Gly—OH, the same procedure as in the Example 1 was repeated as in Example 1 to obtain 186 mg of the protected peptide as a crude product.

150 Milligrams of this protected peptide crude product was treated with hydrogen fluoride and anisole as in Example 1, to obtain 107 mg of powdery substance.

Among this powdery substance, 30 mg thereof was purified and determined under the same condition as in Example 1, there was obtained 8.8 mg of active powder of the above-mentioned objective product.

Amino acid analysis:
Asp: 2.01 (2)
Thr: 4.81 (5)
Ser: 3.66 (4)
Glu: 5.15 (5)
Gly: 3.95 (4)
Val: 0.99 (1)
Leu: 5.01 (5)
Lys: 2.05 (2)
Arg: 1.01 (1)
Pro: 2.02 (2)

EXAMPLE 22

Preparation of ⌐Gly—Ser—Asn—Leu—Ser—Thr—Glu—Val—
Leu—Gly—Lys—Leu—Ser—Gln—Glu—Leu—Ala—Lys—Leu—Gln—Thr—Pro—
Gln—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Ala-Lys(Cl-Z)-Leu-Gln-Thr(Bzl)-Pro-Gln -Thr(Bzl)-Asn-Thr(Bzl)-Gly-Ser(Bzl)-Gly-Thr(Bzl)-Pro-NH₂ and 67.8 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 160 mg of the protected peptide as a crude product.

150 Milligrams of this protected peptide crude product was treated with hydrogen fluoride and anisole as in Example 1, to obtain 106 mg of powdery substance.

Among this powdery substance, 30 mg thereof was purified and determined by means of a high-performance liquid chromatography under the same condition as in Example 1, there was obtained 5 2 mg of active powder of the above-mentioned objective product.

Amino acid analysis:
Asp: 2.01 (2)
Thr: 4.85 (5)
Ser: 3.76 (4)
Glu: 5.15 (5)
Gly: 3.95 (4)
Ala: 1.01 (1)
Val: 0.97 (1)
Leu: 4.99 (5)
Lys: 2.03 (2)
Pro: 2.04 (2)

EXAMPLE 23

Preparation of ⌐Gly—Ser—Asn—Leu—Ser—Thr—Glu—Val—
Leu—Gly—Lys—Leu—Ser—Gln—Glu—Leu—Ser—Lys—Leu—Gln—Thr—Pro—
Gln—Thr—Asn—Thr—Gly—Ser—Gly—Thr—Pro—NH₂

By using 150 mg of Boc-Lys(Cl-Z)-Leu-Ser(Bzl)-Gln-Glu(OcHex)-Leu-Ser(Bzl)-Lys(Cl-Z)-Leu-Gln-Thr(Bzl) -Pro-Gln-Thr(Bzl)-Asn-Thr(Bzl)-Gly-Ser(Bzl)-Gly-Thr(Bzl)-Pro-NH₂ and 66.3 mg of ⌐Gly—Ser(Bzl)—Asn—Leu—Ser(Bzl)—Thr(Bzl)—Glu—Val—Leu—Gly—OH, and the same procedure as in Example 1 was repeated to obtain 160 mg of the protected peptide as a crude product.

150 Milligrams of this protected peptide crude product was treated with hydrogen fluoride and anisole as in Example 1 to obtain 104 mg of powdery substance.

Among this powdery substance, 30 mg thereof was purified and determined by means of a high-performance liquid chromatography, there was obtained 8.1 mg of active powder of the above-mentioned objective product.

Amino acid analysis:
Asp: 2.01 (2)
Thr: 4.85 (5)
Ser: 4.74 (5)
Glu: 5.17 (5)
Gly: 4.00 (4)
Val: 0.96 (1)
Leu: 4.99 (5)
Lys: 2.02 (2)
Pro: 2.01 (2)

EXAMPLE 24

Preparation of ⌐Gly—Ala—Ser—Leu—Ser—Thr—Glu—Val—
Leu—Gly—Lys—Leu—Ser—Gln—Glu—Leu—Gly—Lys—Leu—Gln—Thr—Pro—
Arg—Thr—Asp—Val—Gly—Ala—Gly—Thr—Pro—NH₂

By using 50 mg of Boc-Lys(Z)-Leu-Ser(Bzl)-Gln-Glu(OcHex)-Leu-Gly-Lys(Cl-Z)-Leu-Gln-Thr(Bzl)-Pro-Arg(Tos) -Thr(Bzl)-Asn(OcHex)-Val-Gly-Ala-Gly-Thr(Bzl)-Pro-NH₂ and 21 mg of ⌐Gly—Ala—Ser(Bzl)—Leu—Ser(Bzl)—Thr(Bzl)—Glu—Val—Leu—Gly—OH, and the same procedure as in Example 1 was repeated to obtain 60 mg of the protected peptide as a crude product.

60 Milligrams of this protected peptide crude product was treated with hydrogen fluoride and anisole as in Example 1 to obtain 40 mg of powdery substance.

Among this powdery substance, 30 mg thereof was purified and determined by means of a high-performance liquid chromatography, there was obtained 5.8 mg of active powder of the above-mentioned objective product.

Amino acid analysis:
  Asp: 1.02 (1)
  Thr 3 92 (4)
  Ser: 2.87 (3)
  Glu: 4.10 (4)
  Gly: 5.00 (5)
  Ala: 2.04 (2)
  Val: 1.96 (2)
  Leu: 5.00 (5)
  Lys: 2.02 (2)
  Arg: 1.00 (1)
  Pro: 2.06 (2)
  Leu: 5.07 (5)
  Lys: 2.03 (2)
  Arg: 1.00 (1)
  Pro: 1.96 (2)

EXAMPLE 25

Preparation of ⌐Gly—Ala—Ser—Leu—Ser—Thr—Glu—Val—Leu—Gly—Lys—Leu—Ser—Gln—Glu—Leu—Asn—Lys—Leu—Gln—Thr—Pro—Arg—Thr—Asp—Val—Gly—Ala—Gly—Thr—Pro—NH₂

By using 50 mg of Boc-Lys(Cl-Z)-Leu-Ser(Bzl)-Gln-Glu(OcHex)-Leu-Asn-Lys(Cl-Z)-Leu-Gln-Thr(Bzl)-Pro-Arg(Tos)  -Thr(Bzl)-Asp(OcHex)-Val-Gly-ALa-Gly-Thr(Bzl)-Pro-NH₂ and 21 mg of ⌐Gly—Ala—Ser(Bzl)—Leu—Ser(Bzl)—Thr(Bzl)—Glu—Val—Leu—Gly—OH, and the same procedure as in Example 1 was repeated to obtain 50 mg of the protected peptide as a crude product.

50 Milligrams of this protected peptide crude product was treated with hydrogen fluoride and anisole to obtain 40 mg of powdery product.

Among this powdery product, 30 mg thereof was purified and determined by means of a high-performance liquid chromatography under the same condition as in Example 1, there was obtained 6.4 mg of active powder of the above-mentioned objective product.

Amino acid analysis:
  Asp: 1.98 (2)
  Thr: 3.89 (4)
  Ser: 2.87 (3)
  Glu: 4.15 (4)
  Gly: 4.03 (4)
  Ala: 2.03 (2)
  Val: 1.98 (2)

EXAMPLE 26

Preparation of ⌐Gly—Ala—Ser—Leu—Ser—Thr—Glu—Val—Leu—Gly—Lys—Leu—Ser—Gln—Glu—Leu—His—Lys—Leu—Gln—Thr—Pro—Gln—Thr—Asp—Val—Gly—Ala—Gly—Thr—Pro—NH₂

By using 50 mg of Boc-Lys(Cl-Z)-Leu-Ser(Bzl)-Gln-Glu(OcHex)-Leu-His-Lys(Cl-Z)-Leu-Gln-Thr(Bzl)-Pro-Gln   -Thr(Bzl)-Asp(OcHex)-Val-Gly-Ala-Gly-Thr(Bzl)-Pro-NH₂ and 22 mg of ⌐Gly—Ala—Ser(Bzl)—Leu—Ser(Bzl)—Thr(Bzl)—Glu—Val—Leu—Gly—OH, and the same procedure as in Example 1 was repeated to obtain 50 mg of the protected peptide as a crude product.

50 Milligrams of this protected peptide crude product was treated with hydrogen fluoride and anisole as in Example 1 to obtain 40 mg of powdery product.

Among this powdery product, 30 mg thereof was purified and determined by means of a high-performance liquid chromatography under the same condition as in Example 1, there was obtained 8.7 mg of active powder of the above-mentioned objective product.

Amino acid analysis:
  Asp: 0.99 (1)
  Thr: 3.86 (4)
  Ser: 2.83 (3)
  Glu: 5.06 (5)
  Gly: 4.00 (4)
  Ala: 2.02 (2)
  Val: 2.02 (2)
  Leu: 5.02 (5)
  Lys: 2.03 (2)
  His: 0.99 (1)
  Pro: 2.02 (2)

EXAMPLE 27

Preparation of ⌐Gly—Ala—Ser—Leu—Ser—Thr—Glu—Val—Leu—Gly—Lys—Leu—Ser—Gln—Glu—Leu—Asn—Lys—Leu—Gln—Thr—Pro—Gln—Thr—Asp—Val—Gly—Ala—Gly—Thr—Pro—NH₂

By using 50 mg of Boc-Lys(Z)-Leu-Ser(Bzl)-Gln-Glu(OcHex)-Leu-Asn-Lys(Cl-Z)-Leu-Gln-Thr(Bzl)-Pro-Gln   -Thr(Bzl)-Asp(OcHex)-Val-Gly-Ala-Gly-Thr(Bzl)-Pro-NH₂ and 22 mg of

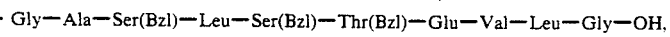
Gly—Ala—Ser(Bzl)—Leu—Ser(Bzl)—Thr(Bzl)—Glu—Val—Leu—Gly—OH, and the same procedure as in Example 1 was repeated to obtain 50 mg of the protected peptide as a crude product.

50 Milligrams of this protected peptide crude product was treated with hydrogen fluoride and anisole as in Example 1 to obtain 38 mg of powdery substance.

Among this powdery substance, 30 mg thereof was purified and determined by means of a high-performance liquid chromatography under the same condition as in Example 1, there was obtained 6.1 mg of the active powder of the above-mentioned objective product.

Amino acid analysis:
Asp: 1.99 (2)
Thr: 3.87 (4)
Ser: 2.85 (3)
Glu: 5.12 (5)
Gly: 4.03 (4)
ALa: 2.03 (2)
Val: 1.99 (2)
Leu: 5.04 (5)
Lys: 2.03 (2)
Pro 2.05 (2)

EXAMPLE 28

Preparation of
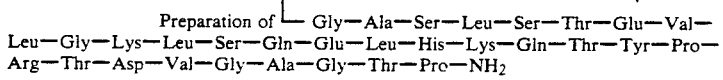
Gly—Ala—Ser—Leu—Ser—Thr—Glu—Val—Leu—Gly—Lys—Leu—Ser—Gln—Glu—Leu—His—Lys—Gln—Thr—Tyr—Pro—Arg—Thr—Asp—Val—Gly—Ala—Gly—Thr—Pro—NH$_2$ By using 50 mg of Boc-Lys(Cl-Z)-Leu-Ser(Bzl)-Gln-Glu(OcHex)-Leu-His(Tos)-Lys(Cl-Z)-Gln-Thr(Bzl)-Tyr(C12-Bzl) -Pro-Arg(Tos)-Thr(Bzl)-Asp(OcHex)-Val-Gly-Ala-Gly-Thr(Bzl)-Pro-NH$_2$ and 19 mg of

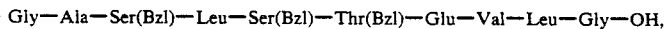
Gly—Ala—Ser(Bzl)—Leu—Ser(Bzl)—Thr(Bzl)—Glu—Val—Leu—Gly—OH, and the same procedure as in Example 1 was repeated to obtain 42 mg of the protected peptide as a crude product.

42 Milligrams of this protected peptide crude product was treated with hydrogen fluoride and anisole as in Example 1 to obtain 30 mg of powdery substance.

Among this powdery substance, 30 mg thereof was purified and determined by means of a high-performance liquid chromatography under the same condition as in Example 1, there was obtained 7.2 mg of active powder of the active powder of the above-mentioned objective product.

Amino acid analysis:
Asp: 1.01 (1)
Thr: 3.90 (4)
Ser: 2.85 (3)
Glu: 4.10 (4)
Gly: 4.01 (4)
Ala: 2.03 (2)
Val: 2.02 (2)
Leu: 4.00 (4)
Tyr: 1.00 (1)
Lys: 2.02 (2)
His: 1.00 (1)
Arg: 1.01 (1)
Pro: 2.04 (2)

EXAMPLE 29

Preparation of
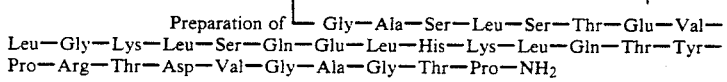
Gly—Ala—Ser—Leu—Ser—Thr—Glu—Val—Leu—Gly—Lys—Leu—Ser—Gln—Glu—Leu—His—Lys—Leu—Gln—Thr—Tyr—Pro—Arg—Thr—Asp—Val—Gly—Ala—Gly—Thr—Pro—NH$_2$ By using 100 mg of Boc-Lys(Z)-Leu-Ser(Bzl)-Gln-Glu(OBzl)-Leu-His-Lys(Cl-Z)-Leu-Gln-Thr(Bzl)-Tyr(Bzl)-Pro -Arg(Tos)-Thr(Bzl)-Asp(Obzl)-Val-Gly-Ala-Gly-Thr(Bzl)-Pro-NH$_2$ and 48 mg of

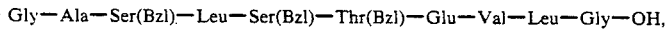
Gly—Ala—Ser(Bzl)—Leu—Ser(Bzl)—Thr(Bzl)—Glu—Val—Leu—Gly—OH, and the same procedure as in Example 1 was repeated to obtain 123 mg of the protected peptide as a crude product.

100 Milligrams of this protected peptide product was treated with hydrogen fluoride and anisole to obtain 71 mg of powdery substance.

Among this powdery substance, 40 mg thereof was purified and determined by means of a high-performance liquid chromatography under the same condition as in Example 1, there was obtained 5.9 mg of the active powder of the above-mentioned objective product.

Amino acid analysis:
Asp: 0.99 (1)
Thr: 3.87 (4)
Ser: 2.89 (3)
Glu: 4.09 (4)
Gly: 4.06 (4)
Ala: 2.05 (2)
Val: 2.00 (2)
Leu: 5.05 (5)

Tyr: 0.89 (1)
Lys: 2.01 (2)
His: 0.97 (1)
Arg: 0.99 (1)
Pro: 2.01 (2)

EXAMPLE 30

Preparation of Gly—Ala—Ser—Leu—Ser—Thr—Glu—Val—Leu—Gly—Lys—Leu—Ser—Gln—Glu—Leu—His—Lys—Leu—Gln—Thr—Pro—Arg—Thr—Asp—Val—Gly—Ala—Gly—Thr—Pro—NH$_2$ By using 100 mg of Boc-Lys(Cl-Z)-Leu-Ser(Bzl)-Gln-Glu(OcHex)-Leu-His(Tos)-Lys(Cl-Z)-Leu-Gln-Thr(Bzl)-Pro -Arg(Tos)-Thr(Bzl)-Asp(OcHex)-Val-Gly-Ala-Gly-Thr(Bzl)-Pro-NH$_2$ and 50 mg of Gly—Ala—Ser(Bzl)—Leu—Ser(Bzl)—Thr(Bzl)—Glu—Val—Leu—Gly—OH, and the same procedure as in Example 1 was repeated to obtain 139 mg of the protected peptide as a crude product.

100 Milligrams of this protecte peptide crude product was treated with hydrogen fluoride and anisole to obtain 78 mg of powdery substance.

Among this powdery substance, 40 mg thereof was purified and determined by means of a high-performance liquid chromatography under the same condition as in Example 1, there was obtained 8.5 mg of the active powder of the above-mentioned objective product.

Amino acid analysis:
Asp: 0.98 (1)
Thr: 3.88 (4)
Ser: 2.88 (3)
Glu: 4.10 (4)
Gly: 4.06 (4)
Ala: 2.04 (2)
Val: 2.01 (2)
Leu: 5.02 (5)
Lys: 2.03 (2)
His: 0.98 (1)
Arg: 1.00 (1)
Pro: 2.03 (2)

Biological Activity Test—I

Each of polypeptide derivatives obtained from the above-mentioned Examples was used as a test sample, and it was diluted to a suitable concentration by using a 1%-sodium acetate aqueous solution (in which 0.1% of bovine serum albumin is contained, and with pH 5.0), thus obtained solution was administered intravenously in an amount of 0.2 ml/100 g of body weight to a Wister strain male rat (having about 180 g of body weight). One hour after the administration, the rat was anesthetized with diethyl ether, and the serum sample was obtained from the blood which was sampled from abdominal vein.

The concentration of calcium in each of the serum samples was determined by means of a calorimetric procedure in accordance with OCPC (Orthocresolphthalein complexone) method [BUNSEKI-KAGAKU-SHIMPO-SOHSETSU (Review of Progress in Analytical Chemistry), Vol. 17, pp. 127–136, (1968) by Masayuki Saitoh; American Journal of Clinical Pathology, Vol. 45, pp. 290–296, (1966) by Connerty, H. V., and Briggs, A. R.; RINSHOH-BYOHRI (Clinical Pathology), Vol. 17, Supplemental Issue, pp. 85, (1969) by Etsuko Yoshida], by using a biochemical automatic analyzing equipment (COBAS BIO, manufactured by Hoffmann-La Roche & Co., A. G.).

As the result, as compared with the concentration of calcium in the serum samples obtained from the rats in control group to which a test polypeptide derivative sample of the present invention was not administered, the concentration of calcium in the serum samples obtained from the rats in test group to which a test polypeptide derivative sample of the present invention obtained from each of the Examples were shown gradually decreased depend on the lowering of the dosage of the test sample.

The concentrations of calcium in the serum samples (mg/dl) obtained from the test rats of test groups and control groups are shown in Table 1 as follows.

TABLE 1

| Example No. of polypeptide as test sample | Dosage of test sample (ng/kg) | | | |
|---|---|---|---|---|
| | Test groups | | | Control group |
| | 6.25 | 12.5 | 25.0 | 0 |
| | Concentration of calcium in the serum sample (mg/dl) | | | |
| Example 1  | 9.04 | 8.16 | 7.62 | 10.68 |
| Example 3  | 8.78 | 7.81 | 7.18 | 9.84 |
| Example 4  | 8.51 | 7.80 | 6.74 | 9.74 |
| Example 7  | 8.65 | 7.70 | 7.39 | 9.69 |
| Example 8  | 8.58 | 7.94 | 7.40 | 9.69 |
| Example 10 | 8.75 | 7.83 | 7.44 | 9.69 |
| Example 11 | 8.92 | 8.09 | 7.91 | 10.50 |
| Example 12 | 9.22 | 8.08 | 7.63 | 10.43 |
| Example 13 | 8.84 | 8.28 | 7.66 | 10.50 |
| Example 14 | 9.05 | 7.95 | 7.72 | 10.50 |
| Example 15 | 8.86 | 8.10 | 7.65 | 10.43 |
| Example 17 | 9.28 | 8.06 | 7.59 | 10.43 |
| Example 18 | 8.97 | 7.80 | 7.34 | 10.09 |
| Example 19 | 9.24 | 7.80 | 7.33 | 10.09 |
| Example 20 | 8.96 | 7.95 | 7.23 | 10.09 |
| Example 21 | 8.89 | 7.90 | 7.49 | 10.50 |
| Example 22 | 9.37 | 8.36 | 7.56 | 10.35 |
| Example 23 | 8.88 | 8.40 | 7.33 | 10.35 |
| Example 24 | 9.02 | 8.00 | 7.20 | 10.35 |
| Example 25 | 9.31 | 7.64 | 7.07 | 10.35 |
| Example 26 | 9.22 | 8.21 | 7.51 | 10.30 |
| Example 27 | 8.84 | 8.29 | 7.62 | 10.30 |
| Example 28 | 9.11 | 8.01 | 7.44 | 9.99 |
| Example 29 | 9.35 | 8.57 | 7.72 | 9.99 |
| Example 30 | 9.02 | 8.14 | 7.31 | 9.99 |

As can be seen from the results shown in Table 1, it is clearly understood that any one of these polypeptide derivatives of the present invention possess excellent activities for lowering the concentration of calcium in the serum sample.

Biological Activity Test—II

The intestinal absorpability of each of polypeptide derivatives obtained in Examples of the present invention and those of calcium metabolism improving agents according to the present invention were tested as follows.

Thus, 3 4 Wister strain male rats (average body weight: about 250 g, which were subjected to fasting) in one test group were used as test animals. Each one of rats was anesethized by intraperitoneal administration with pentobarbital in an amount of 40 mg/kg, then the rat was subjected to abdominal section and was intraduodenal administration of a test sample solution in an amount of 0.5 ml/100 g. One hour after the administration, the rat was anesthetized with diethyl ether and the serum sample was obtained from the blood which was sampled from abdominal vein.

The concentration of calcium (mg/dl) in each of serum samples was determined by means of a calorimetric procedure in accordance with OCPC (Orthocresolphthalein complexone) method [American Journal of Clinical Pathology, Vol. 45, pp. 290, (1966) by Connerty, H. V., and Briggs, A. R.] by using a biochemical automatic analyzing equipment (COBAS BIO, manufactured by Hoffmann-La Roche & Co., A.G.).

As to the test sample solution, a proteolytic enzyme inhibitor and citric acid as to the additives for the objective pharmaceutical composition for use in calcium metabolism improving agent, were dissolved or suspended in distilled water, and thus obtained solution or suspension was admixed with an aqueous solution of a polypeptide derivative being prepared in each of the Examples which was diluted to a suitable concentration with a 1%-sodium acetate aqueous solution (in which 0.1% of bovine serum albumin (BSA) is contained, having pH 5.0), the whole mixture thus obtained was used as test sample solution for intraduodenal administration.

As the result, an average value of calcium concentration (mg/dl) in the serum of each of test rats (3-4 rats in one test group) are shown in the following Table 2.

As can be seen from the data shown in Table 2, excellent lowering effect of calcium concentration in the serum can be achieved by intestinal administration with polypeptide derivative prepared in the Examples when said polypeptide derivative is used together with a proteolytic enzyme inhibitor and an acid.

TABLE 2

| Example No. of polypeptide as test sample (1,000 ng/kg) | Additive (Proteolytic enzyme inhibitor) | + | Citric acid (50 mg/kg) | Concentration of calcium in serum sample (mg/dl) |
| --- | --- | --- | --- | --- |
| Example 3 | SBTI (20 mg/kg) | + | Citric acid (50 mg/kg) | 8.40 |
| Example 8 | Aprotinin (20 mg/kg) | + | Citric acid (50 mg/kg) | 7.70 |
| Example 11 | Urinastatin (50,000 U/kg) | + | Citric acid (50 mg/kg) | 8.06 |
| Example 12 | Camostat mesylate (20 mg/kg) | + | Citric acid (50 mg/kg) | 7.21 |
| Example 13 | Gabexate mesylate (20 mg/kg) | + | Citric acid (50 mg/kg) | 7.48 |
| Example 15 | Camostat mesylate (20 mg/kg) | + | Citric acid (50 mg/kg) | 7.46 |
| Example 17 | Gabexate mesylate (20 mg/kg) | + | Citric acid (50 mg/kg) | 7.28 |
| Example 18 | Nafamostat mesylate (20 mg/kg) | + | Citric acid (50 mg/kg) | 7.37 |

TABLE 2-continued

| Example No. of polypeptide as test sample (1,000 ng/kg) | Additive (Proteolytic enzyme inhibitor) | + | Citric acid (50 mg/kg) | Concentration of calcium in serum sample (mg/dl) |
| --- | --- | --- | --- | --- |
| Example 21 | FK-448 (20 mg/kg) | + | Citric acid (50 mg/kg) | 7.47 |
| Example 23 | Chymostatin (20 mg/kg) | + | Citric acid (50 mg/kg) | 7.71 |
| Example 24 | Nafamostat mesylate (20 mg/kg) | + | Citric acid (50 mg/kg) | 7.42 |
| Example 28 | Leupeptin (20 mg/kg) | + | Citric acid (50 mg/kg) | 7.54 |
| Example 30 | FK-448 (20 mg/kg) | + | Citric acid (50 mg/kg) | 7.63 |
| Example 15 | (Not added) | + | (Not added) | 9.83 |

Example of Pharmaceutical Preparation—1

300 Units of the compound prepared in Example 1 was admixed with 150 mg of Leupeptin, to this mixture was added with a suitable amounts of crystalline cellulose, calcium carboxymethyl cellulose, hydroxypropyl cellulose and magnesium stearate, then the whole mixture was mixed thoroughly to make the mixture as uniform composition. Said mixture was shaped into tablets then they were subjected to enteric coating process to make them as tablets having enteric coating.

Example of Pharmaceutical Preparation—2

400 Units of the compound prepared in Example 24 was admixed with 300 mg of Chymostatin, to this mixture was added with a suitable amounts of crystalline cellulose, calcium carboxymethyl cellulose and talc, then the whole mixture was mixed thoroughly to make the mixture as uniform composition. Said mixture was filled in gelatin capsules. Thus obtained filled capsules were subjected to enteric coating process to make them as capsules having enteric coating.

Example of Pharmaceutical Preparation—3

50 Units of the compound prepared in Example 12 was admixed with 50 mg of Aprotinin, to this mixture was added a suitable amount of Witepsol H-15 (a trademark of a fatty acid glyceride, manufactured by Dynamit Nobel Co.) to make the mixture as suppositories.

Example of Pharmaceutical Preparation—4

350 Units of the compound prepared in Example 25 was dissolved in an aqueous solution of sodium citrate, then the pH of this solution was adjusted to pH=7.4 by adding 1N-hydrochloric acid, then purified water for injection was added to the above-mentioned solution to prepare injection preparation.

Example of Pharmaceutical Preparation—5

300 Units of the compound prepared in Example 20 and 200 mg of Camostat mesylate were dissolved in an aqueous solution of lactic acid, the pH of this solution was adjusted to pH=7.0 by using 1N-sodium hydroxide aqueous solution, then a suitable amount of water was added to the above-mentioned solution to prepare a liquid preparation which is suitable for using a nasal administration.

What is claimed is:

1. Polypeptide derivatives, acid-addition salts thereof and complexes thereof represented by the general formula (1)

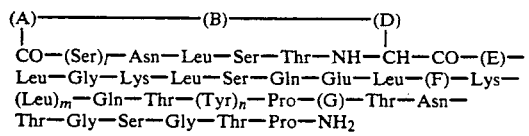
CO—(Ser)$_l$—Asn—Leu—Ser—Thr—NH—CH—CO—(E)—Leu—Gly—Lys—Leu—Ser—Gln—Glu—Leu—(F)—Lys—(Leu)$_m$—Gln—Thr—(Tyr)$_n$—Pro—(G)—Thr—Asn—Thr—Gly—Ser—Gly—Thr—Pro—NH$_2$ wherein (A) is a lower alkylene group; (B) is —NH—CO—, —S— or an oxyphenylene group; (D) is a lower alkylene group; (E) is a valine residue, a glycine residue or an isoleucine residue; (F) is a histidine residue, an asparagine residue, a glycine residue, an alanine residue, a serine residue, a leucine residue or a glutamine residue; and (G) is an arginine residue or a glutamine residue, respectively; l, m and n are each 0 or 1; provided that when l is 0 and (A) is a methylene group, then (D) is a methylene group or an ethylene group; or represented by the general formula (2)

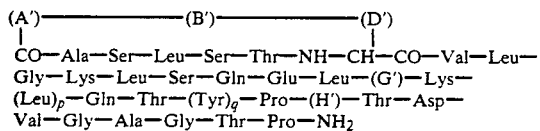
CO—Ala—Ser—Leu—Ser—Thr—NH—CH—CO—Val—Leu—Gly—Lys—Leu—Ser—Gln—Glu—Leu—(G')—Lys—(Leu)$_p$—Gln—Thr—(Tyr)$_q$—Pro—(H')—Thr—Asp—Val—Gly—Ala—Gly—Thr—Pro—NH$_2$ wherein (A') is a lower alkylene group; (B') is —NH—CO—; (D') is a lower alkylene group; (G') is a histidine residue, a asparagine residue or a glycine o residue; and (H') is an arginine residue or a glutamine residue, respectively; and p and q are each 0 or 1.

2. The polypeptide derivatives, acid-addition salts thereof and complexes thereof according to claim 1, wherein the polypeptide derivatives are represented by the general formula (1)

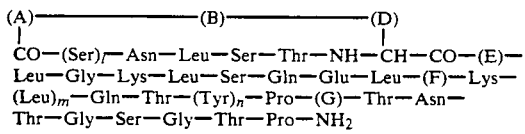
CO—(Ser)$_l$—Asn—Leu—Ser—Thr—NH—CH—CO—(E)—Leu—Gly—Lys—Leu—Ser—Gln—Glu—Leu—(F)—Lys—(Leu)$_m$—Gln—Thr—(Tyr)$_n$—Pro—(G)—Thr—Asn—Thr—Gly—Ser—Gly—Thr—Pro—NH$_2$ wherein (A), (B), (D), (E), (F), (G), l, m and n are the same as defined above.

3. The polypeptide derivatives, acid-addition salts thereof and complexes thereof according to claim 1, wherein the polypeptide derivatives are represented by the general formula (2)

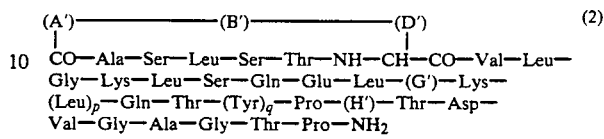
CO—Ala—Ser—Leu—Ser—Thr—NH—CH—CO—Val—Leu—Gly—Lys—Leu—Ser—Gln—Glu—Leu—(G')—Lys—(Leu)$_p$—Gln—Thr—(Tyr)$_q$—Pro—(H')—Thr—Asp—Val—Gly—Ala—Gly—Thr—Pro—NH$_2$ wherein (A'), (B'), (D'), (G'), (H'), p and q are the same as defined above.

4. The polypeptide derivatives, acid-addition salts thereof and complexes thereof according to claim 2, wherein the polypeptide derivatives are represented by the general formula (3)

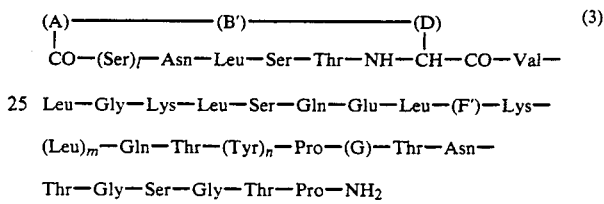
CO—(Ser)$_l$—Asn—Leu—Ser—Thr—NH—CH—CO—Val—Leu—Gly—Lys—Leu—Ser—Gln—Glu—Leu—(F')—Lys—(Leu)$_m$—Gln—Thr—(Tyr)$_n$—Pro—(G)—Thr—Asn—Thr—Gly—Ser—Gly—Thr—Pro—NH$_2$ wherein (A) is a lower alkylene group; (B') is —NH—CO—; (D) is a lower alkylene group; (F') is a histidine residue, an asparagine residue or a glycine residue; (G) is an arginine residue or a glutamine residue, respectively; and l, m and n are each 0 or 1.

5. The polypeptide derivative, acid-addition salt thereof and complex thereof according to claim 2, wherein the polypeptide is the formula of:

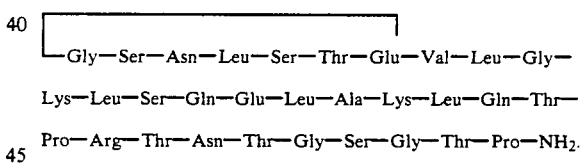
—Gly—Ser—Asn—Leu—Ser—Thr—Glu—Val—Leu—Gly—Lys—Leu—Ser—Gln—Glu—Leu—Ala—Lys—Leu—Gln—Thr—Pro—Arg—Thr—Asn—Thr—Gly—Ser—Gly—Thr—Pro—NH$_2$.

6. The polypeptide derivatives, acid-addition salts thereof and complexes thereof according to claim 2, wherein the polypeptide derivatives are formulas of:

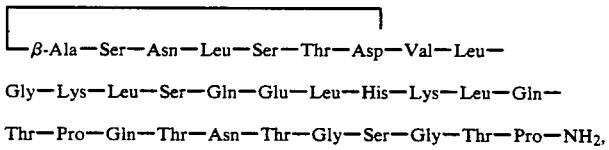
—β-Ala—Ser—Asn—Leu—Ser—Thr—Asp—Val—Leu—Gly—Lys—Leu—Ser—Gln—Glu—Leu—His—Lys—Leu—Gln—Thr—Pro—Gln—Thr—Asn—Thr—Gly—Ser—Gly—Thr—Pro—NH$_2$,

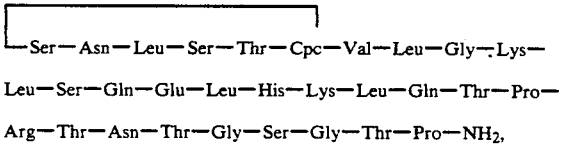
—Ser—Asn—Leu—Ser—Thr—Cpc—Val—Leu—Gly—Lys—Leu—Ser—Gln—Glu—Leu—His—Lys—Leu—Gln—Thr—Pro—Arg—Thr—Asn—Thr—Gly—Ser—Gly—Thr—Pro—NH$_2$,

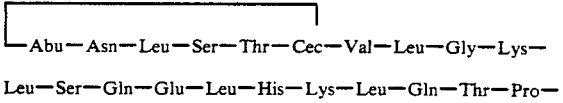
—Abu—Asn—Leu—Ser—Thr—Cec—Val—Leu—Gly—Lys—Leu—Ser—Gln—Glu—Leu—His—Lys—Leu—Gln—Thr—Pro—

-continued

Arg—Thr—Asn—Thr—Gly—Ser—Gly—Thr—Pro—NH$_2$,

⌐————————————————————⌐
└—CH$_2$CO—Ser—Asn—Leu—Ser—Thr—Tyr—Val—Leu—Gly—

Lys—Leu—Ser—Gln—Glu—Leu—Asn—Lys—Leu—Gln—Thr—

Pro—Arg—Thr—Asn—Thr—Gly—Ser—Gly—Thr—Pro—NH$_2$, and

⌐————————————————————⌐
└—COCH$_2$CH$_2$CO—Asn—Leu—Ser—Thr—Lys—Val—Leu—

Gly—Lys—Leu—Ser—Gln—Glu—Leu—Asn—Lys—Leu—Gln—

Thr—Pro—Gln—Thr—Asn—Thr—Gly—Ser—Gly—Thr—Pro—NH$_2$.

7. The polypeptide derivatives, acid-addition salts thereof and complexes thereof according to claim 2, wherein the polypeptide derivatives are formulas of:

⌐————————————————————⌐
└—Gly—Ser—Asn—Leu—Ser—Thr—Glu—Ile—Leu—Gly—

Lys—Leu—Ser—Gln—Glu—Leu—Gly—Lys—Leu—Gln—Thr—

Pro—Arg—Thr—Asn—Thr—Gly—Ser—Gly—Thr—Pro—NH$_2$,

⌐————————————————————⌐
└—Gly—Ser—Asn—Leu—Ser—Thr—Glu—Val—Leu—Gly—

Lys—Leu—Ser—Gln—Glu—Leu—Ser—Lys—Leu—Gln—Thr—

Pro—Arg—Thr—Asn—Thr—Gly—Ser—Gly—Thr—Pro—NH$_2$,

⌐————————————————————⌐
└—Gly—Ser—Asn—Leu—Ser—Thr—Glu—Val—Leu—Gly—

Lys—Leu—Ser—Gln—Glu—Leu—Leu—Lys—Leu—Gln—Thr—

Pro—Arg—thr—Asn—Thr—Gly—Ser—Gly—Thr—Pro—NH$_2$,

⌐————————————————————⌐
└—Gly—Ser—Asn—Leu—Ser—Thr—Glu—Val—Leu—Gly—

Lys—Leu—Ser—Gln—Glu—Leu—Gln—Lys—Leu—Gln—Thr—

Pro—Arg—Thr—Asn—Thr—Gly—Ser—Gly—Thr—Pro—NH$_2$,

⌐————————————————————⌐
└—Gly—Ser—Asn—Leu—Ser—Thr—Glu—Val—Leu—Gly—

Lys—Leu—Ser—Gln—Glu—Leu—Ala—Lys—Leu—Gln—Thr—

Pro—Gln—Thr—Asn—Thr—Gly—Ser—Gly—Thr—Pro—NH$_2$ and

⌐————————————————————⌐
└—Gly—Ser—Asn—Leu—Ser—Thr—Glu—Val—Leu—Gly—

Lys—Leu—Ser—Gln—Glu—Leu—Ser—Lys—Leu—Gln—Thr—

Pro—Gln—Thr—Asn—Thr—Gly—Ser—Gly—Thr—Pro—NH$_2$.

8. The polypeptide derivative, acid-addition salt thereof and complex thereof according to claim 2, wherein the polypeptide derivative is the formula of:

⌐————————————————————⌐
└—Gly—Ser—Asn—Leu—Ser—Thr—Glu—Val—Leu—Gly—

Lys—Leu—Ser—Gln—Glu—Leu—Asn—Lys—Leu—Gln—Thr—

Pro—Arg—Thr—Asn—Thr—Gly—Ser—Gly—Thr—Pro—NH$_2$.

9. The polypeptide derivative, acid-addition salt thereof and complex thereof according to claim 2, wherein the polypeptide derivative is the formula of:

⌐————————————————————⌐
└—Gly—Ser—Asn—Leu—Ser—Thr—Glu—Val—Leu—Gly—

Lys—Leu—Ser—Gln—Glu—Leu—His—Lys—Leu—Gln—Thr—

Pro—Gln—Thr—Asn—Thr—Gly—Ser—Gly—Thr—Pro—NH$_2$.

10. The polypeptide derivative, acid-addition salt thereof and complex thereof according to claim 2, wherein the polypeptide derivative is the formula of:

⌐————————————————————⌐
└—Gly—Ser—Asn—Leu—Ser—Thr—Glu—Val—Leu—Gly—
Lys—Leu—Ser—Gln—Glu—Leu—Gly—Lys—Leu—Gln—Thr—
Pro—Arg—Thr—Asn—Thr—Gly—Ser—Gly—Thr—Pro—NH$_2$

11. The polypeptide derivatives, acid-addition salts thereof and complexes thereof according to claim 2, wherein the polypeptide derivatives are the formulas of:

⌐————————————————————⌐
└—Gly—Ser—Asn—Leu—Ser—Thr—Glu—Val—Leu—Gly—
Lys—Leu—Ser—Gln—Glu—Leu—His—Lys—Leu—Gln—Thr—
Pro—Arg—Thr—Asn—Thr—Gly—Ser—Gly—Thr—Pro—NH$_2$,

⌐————————————————————⌐
└—Acp—Asn—Leu—Ser—Thr—Asp—Val—Leu—Gly—Lys—
Leu—Ser—Gln—Glu—Leu—His—Lys—Leu—Gln—Thr—Pro—
Arg—Thr—Asn—Thr—Gly—Ser—Gly—Thr—Pro—NH$_2$, and ⌐————————————————————⌐
└—Gly—Ser—Asn—Leu—Ser—Thr—Glu—Val—Leu—Gly—
Lys—Leu—Ser—Gln—Glu—Leu—Asn—Lys—Leu—Gln—Thr—
Pro—Gln—Thr—Asn—Thr—Gly—Ser—Gly—Thr—Pro—NH$_2$.

12. The polypeptide derivatives, acid-addition salts thereof and complexes thereof according to claim 3, wherein the polypeptide derivatives are the formulas of:

⌐Gly—Ala—Ser—Leu—Ser—Thr—Glu—Val—Leu—Gly—
Lys—Leu—Ser—Gln—Glu—Leu—Gly—Lys—Leu—Gln—Thr—
Pro—Arg—Thr—Asp—Val—Gly—Ala—Gly—Thr—Pro—NH₂,

⌐Gly—Ala—Ser—Leu—Ser—Thr—Glu—Val—Leu—Gly—
Lys—Leu—Ser—Gln—Glu—Leu—Asn—Lys—Leu—Gln—Thr—
Pro—Arg—Thr—Asp—Val—Gly—Ala—Gly—Thr—Pro—NH₂
and ⌐Gly—Ala—Ser—Leu—Ser—Thr—Glu—Val—Leu—Gly—
Lys—Leu—Ser—ln—lu—Leu—Asn—Lys—Leu—Gln—Thr—
Pro—Gln—Thr—Asp—Val—Gly—Ala—GTly—Thr—Pro—NH₂

13. Polypeptide derivatives, and their blocked derivatives of which the side chain functional group is protected, acid-addition salts thereof and complexes thereof represented by the general formula (3)

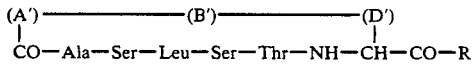

```
  (A')―――――――(B')―――――――(D')
   |                       |
  CO—Ala—Ser—Leu—Ser—Thr—NH—CH—CO—R
``` wherein (A') is a lower alkylene group; (B') is —NH-CO—; and (D') is a lower alkylene group, respectively; and R is an activated carboxyl group or hydroxyl group, or a group of the formula -Val-Leu-Gly-R', wherein R' is an activated carboxyl group or a hydroxyl group.

14. A pharmaceutical composition for lowering blood serum calcium which comprises a polypeptide derivative, acid-addition salt thereof or complex thereof as claimed in claim 1, together with a pharmaceutically acceptable carrier.

15. A pharmaceutical composition for lowering blood serum calcium wherein the active ingredients, at least one polypeptide derivative, acid-addition salt thereof or complex thereof represented by the general formula (1) or (2) as claimed in claim 1, together with a proteolytic enzyme inhibitor and/or a pharmaceutically acceptable acid.

16. A pharmaceutical composition for treating hypercalcemia by using polypeptide derivative, acid-addition salt thereof or complex thereof selected from the group consisting of:

⌐Gly—Ser—Asn—Leu—Ser—Thr—Glu—Val—Leu—Gly—
Lys—Leu—Ser—Gln—Glu—Leu—Asn—Lys—Leu—Gln—Thr—
Pro—Arg—Thr—Asn—Thr—Gly—Ser—Gly—Thr—Pro—NH₂,

⌐Gly—Ser—Asn—Leu—Ser—Thr—Glu—Val—Leu—Gly—
Lys—Leu—Ser—Gln—Glu—Leu—His—Lys—Leu—Gln—Thr—
Pro—Gln—Thr—Asn—Thr—Gly—Ser—Gly—Thr—Pro—NH₂,

⌐Gly—Ser—Asn—Leu—Ser—Thr—Glu—Val—Leu—Gly—
Lys—Leu—Ser—Gln—Glu—Leu—Gly—Lys—Leu—Gln—Thr—
Pro—Arg—Thr—Asn—Thr—Gly—Ser—Gly—Thr—Pro—NH₂
and ⌐Gly—Ser—Asn—Leu—Ser—Thr—Glu—Val—Leu—Gly—
Lys—Leu—Ser—Gln—Glu—Leu—Ala—Lys—Leu—Gln—Thr—
Pro—Arg—Thr—Asn—Thr—Gly—Ser—Gly—Thr—Pro—NH₂, together with a pharmaceutically acceptable carrier.

17. A method for lowering blood calcium serum, which comprises administering to a host an effective amount of a polypeptide derivative, acid-addition salt thereof or complex thereof represented by the general formula (1) or (2) as claimed in claim 1.

* * * * *

UNITED STATES PATENT AND TRADEMARK OFFICE
CERTIFICATE OF CORRECTION

PATENT NO. : 5,204,326
DATED : April 20, 1993
INVENTOR(S) : Setsuro Fujii et al.

It is certified that error appears in the above-indentified patent and that said Letters Patent is hereby corrected as shown below:

Claim 1, column 91, line 35, "a" (first occurrence) should read --an--; and line 35, after "glycine" delete "o";

Claim 7, column 93, line 41, "thr" should read --Thr--;

Claim 11, column 94, line 58, "Acp" should read --Asp--;

Claim 12, column 95, line 17, "Gtly" should read --Gly--;

Claim 17, column 96, line 34, "calcium serum" should read --serum calcium--; and In the Abstract, line 11, "composition" should read --compositions--.

Signed and Sealed this

Eighteenth Day of January, 1994

Attest:

BRUCE LEHMAN

Attesting Officer

Commissioner of Patents and Trademarks